United States Patent
Ohtani et al.

(10) Patent No.: US 6,472,389 B1
(45) Date of Patent: Oct. 29, 2002

(54) PYRROLO[1,2-B] PYRIDAZINE DERIVATIVES HAVING SPLA$_2$ INHIBITORY EFFECT

(75) Inventors: Mitsuaki Ohtani; Masahiro Fuji; Yoshikazu Fukui; Makoto Adachi, all of Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/673,413

(22) PCT Filed: May 20, 1999

(86) PCT No.: PCT/JP99/02630

§ 371 (c)(1),
(2), (4) Date: Oct. 18, 2000

(87) PCT Pub. No.: WO99/59999

PCT Pub. Date: Nov. 25, 1999

(30) Foreign Application Priority Data

May 21, 1998 (JP) .......................................... 10-139319
Aug. 31, 1998 (JP) .......................................... 10-244736

(51) Int. Cl.$^7$ .................... A61K 31/5025; C07D 487/04
(52) U.S. Cl. .................... 514/233.2; 514/248; 544/119; 544/235; 548/517; 548/527; 548/557
(58) Field of Search .................. 544/235, 119; 514/248, 233.2

(56) References Cited

FOREIGN PATENT DOCUMENTS

| | | |
|---|---|---|
| EP | 0 620 214 B1 | 10/1994 |
| EP | 0 620 215 B1 | 10/1994 |
| EP | 0 675 110 A1 | 10/1995 |
| WO | WO 96/03120 | 2/1996 |
| WO | WO 96/03376 | 2/1996 |
| WO | WO 96/03383 | 2/1996 |
| WO | WO 97/21664 | 6/1997 |
| WO | WO 97/21716 | 6/1997 |
| WO | WO 98/18464 | 5/1998 |
| WO | WO 98/24437 | 6/1998 |
| WO | WO 98/24756 | 6/1998 |
| WO | WO 98/24794 | 6/1998 |
| WO | WO 98/25609 | 6/1998 |
| WO | WO 99/00360 | 1/1999 |

OTHER PUBLICATIONS

Puri, International Journal of Biochemistry and Cell Biology, 30,p. 1107–1122, (1998).*
K. Terao et al., J. Chem. Soc. Perkin Trans. I, "Intramolecular Amidoseleniation of N–Alkenyl Imidates to N–Heterocycles," pp. 1837–1843 (1986) Royal Society of Chemistry, Thomas Graham House.
R. Bishop et al., Synthesis, "An Efficient Synthesis of 4, 4–Disubstituted 5, 6–Dihydro–3(4H)–pyridinone 1–Oxides by Thermal Cyclisation of Unsaturated 1, 2–Hydroxyiminoketones," pp. 997–999 (1988). Georg Thieme Verlag.
W. Flitsch et al., Chem. Ber., vol. 102, "Zur Chemie der 1–Amino–pyrrole," pp. 3268–3276 (1969) Wiley—V C H.
J.M. Ruxer et al., J. Heterocyclic Chem., vol. 31, "Synthesis of 1,4–Dihydro–4–oxopyrrolo[1,2–b]pyridazine–3–caboxylic Acids and 1,4–Dihydro–4–Oxoimidazo[1,5–b]pyridazine–3–carboxylic Acids as Potential Antibacterial Agents," pp. 409–417 (1994) HeteroCorporation.
S. Berge et al., Journal of Pharmaceutical Sciences, vol. 66, No. 1, "Pharmaceutical Salts," pp. 1–19 (1977) John Wiley & Sons, Inc.
E. Alexander et al., J. Am. Chem. Soc., vol. 66, "A simultaneous Condensation– Reduction Method for the Preparation of Ethyl Monoalkylcyanoacetates," pp. 886–888 (1944).
M. Cottin et al., Compt. Rend., vol. 253, Academie Des Sciences, "Chimie Organique—Preparation de nitriles ethyleniques," pp. 1808–1809 (1961) Elsevier Partis.
A. Phadke et al., Indian Journal of Chemistry, vol. 25B, No. 12, "Synthesis of Norphytene & Its Isomer 2,6,10, 14–Tetramethyl–pentadec–2–ene," pp. 1249–1250 (1986) India; Publications & Information Directorate; Scientific Publishers.
L. Reynolds et al., Analytical Biochemistry, vol. 204 "Analysis of Human Synovial Fluid Phospholipase A$_2$ on Short Chain Phosphatidylcholine–Mixed Micelles: Development of a Spectrophotometric Assay Suitable for a Microtiterplate Reader 1," pp. 190–197 (1992) Academic Press, Inc.
S. Hagishita et al., J. Med. Chem., vol. 39, No. 19, "Potent Inhibitors of Secretory Phospholipase A2: Synthesis and Inhibitory Activities of Indolizine and Indene Derivatives," pp. 3636–3658 (1996) American Chemical Society.
H. Bungard, Design of Prodrugs, pp. 7–9, 21–24 (1985) Elsevier, Amsterdam.

* cited by examiner

Primary Examiner—Emily Bernhardt
(74) Attorney, Agent, or Firm—Foley & Lardner

(57) ABSTRACT

The present invention provides a compound having sPLA$_2$ inhibiting activity.

The compound represented by the formula (I):

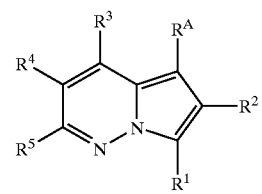

wherein $R^1$ is —(L$^1$)—R$^6$ wherein L$^1$ is a divalent linking group of 1 to 18 atoms or the like, and R$^6$ is a carbocyclic ring substituted by at least one non-interfering substituent or the like; R$^2$ is C1 to C3 alkyl or the like; R$^3$ is —(L$^2$)-(acidic group); R$^4$ and R$^5$ are hydrogen atoms, non-interfering substituents, carbocyclic groups or the like; X is independently oxygen atom of sulfur atom; and R$^A$ is —C(=X)—C(=X)—NH$_2$ or the like; the prodrugs thereof, their pharmaceutically acceptable salts, or their solvates, and a composition for inhibiting sPLA$_2$ containing them as effective ingredients.

7 Claims, No Drawings

PYRROLO[1,2-B] PYRIDAZINE DERIVATIVES HAVING SPLA₂ INHIBITORY EFFECT

TECHNICAL FIELD

The present invention relates to a pyrrolo[1,2-b] pyridazine derivative effective for inhibiting sPLA$_2$-mediated fatty acid release.

BACKGROUND ART sPLA$_2$ (secretory phospholipase A$_2$) is an enzyme that hydrolyzes membrane phospholipids and has been considered to be a rate-determining enzyme that governs the so-called arachidonate cascade where arachidonic acid, the hydrolysis product, is the starting material. Moreover, lysophospholipids that are produced as by-products in the hydrolysis of phospholipids have been known as important mediators in cardiovascular diseases. Accordingly, in order to normalize excess functions of the arachidonate cascade and the lysophospholipids, it is important to develop compounds which inhibit the liberation of sPLA$_2$-mediated fatty acids (for example, arachidonic acid), namely, compounds which inhibit the activity or production of sPLA$_2$. Such compounds are useful for general treatment of symptoms, which are induced and/or sustained by an excess formation of sPLA$_2$, such as septic shock, adult respiratory distress syndrome, pancreatitis, injury, bronchial asthma, allergic rhinitis, chronic rheumatism, arteriosclerosis, cerebral apoplexy, cerebral infarction, inflammatory colitis, psoriasis, cardiac insufficiency, cardiac infarction, and so on. The participation of sPLA$_2$ is considered to be extremely wide and, besides, its action is potent.

There are known, as examples of sPLA$_2$ inhibitor, indole derivatives in EP-620214 (JP Laid-Open No. 010838/95), EP-620215 (JP Laid-Open No. 025850/95), EP-675110 (JP Laid-Open No. 285933/95), WO 96/03376, and WO 99/00360; indene derivatives in WO 96/03120; indolizine derivatives in WO 96/03383; naphthalene derivatives in WO 97/21664 and WO 97/21716; tricyclic derivatives in WO 98/18464; pyrazole derivatives in WO 98/24437; phenylacetamide derivatives in WO 98/24756; phenyl glyoxamide derivatives in WO 98/24794; pyrrole derivatives in WO 98/25609.

DISCLOSURE OF INVENTION

The present invention provides pyrrolo[1,2-b]pyridazine derivatives having sPLA$_2$ inhibiting activity and being useful for treatment of septic shock, adult respiratory distress syndrome, pancreatitis, injury, bronchial asthma, allergic rhinitis, chronic rheumatism, arterial sclerosis, cerebral hemorrhage, cerebral infarction, inflammatory colitis, psoriasis, cardiac failure, and cardiac infarction.

The present invention relates to i) a compound represented by the formula (I):

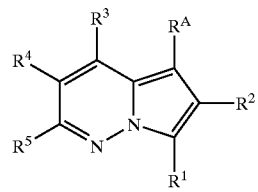

(I)

wherein R$^1$ is a group selected from (a) C6 to C20 alkyl, C6 to C20 alkenyl, C6 to C20 alkynyl, carbocyclic groups, and heterocyclic groups, (b) the groups represented by (a) each substituted independently with at least one group selected from non-interfering substituents, and (c) —(L$^1$)—R$^6$ wherein L$^1$ is a divalent linking group of 1 to 18 atom(s) selected from hydrogen atom(s), nitrogen atom(s), carbon atom(s), oxygen atom(s), and sulfur atom(s), and R$^6$ is a group selected from the groups (a) and (b);

R$^2$ is hydrogen atom or a group containing 1 to 4 non-hydrogen atoms;

R$^3$ is —(L$^2$)-(acidic group) wherein L$^2$ is an acid linker having an acid linker length of 1 to 5;

R$^4$ and R$^5$ are selected independently from hydrogen atom, non-interfering substituents, carbocyclic groups, carbocyclic groups substituted with a non-interfering substituent(s), heterocyclic groups, and heterocyclic groups substituted by a non-interfering substituent(s); and R$^A$ is a group represented by the formula:

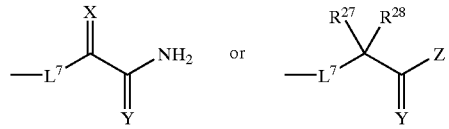

wherein L$^7$ is a divalent linker group selected from a bond or a divalent group selected from —CH$_2$—, —O—, —S—, —NH—, or —CO—, R$^{27}$ and R$^{28}$ are independently hydrogen atom, C1 to C3 alkyl or a halogen; X and Y are independently an oxygen atom or a sulfur atom; and Z is —NH$_2$ or —NHNH$_2$; the prodrugs thereof, or their pharmaceutically acceptable salts; or their solvates.

In more detail, the present invention relates to ii) a compound represented by the formula (II):

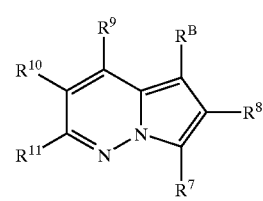

(II)

where R$^7$ is —(CH$_2$)m—R$^2$ wherein m is an integer from 1 to 6, and R$^{12}$ is (d) a group represented by the formula:

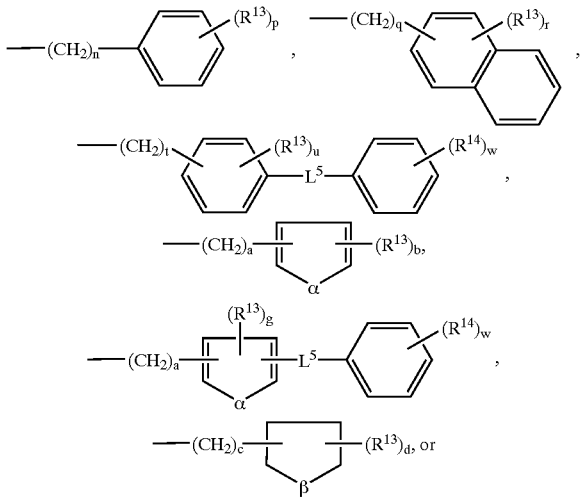

-continued

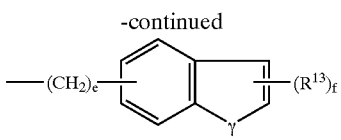

wherein a, c, e, n, q, and t are independently an integer from 0 to 2, $R^{13}$ and $R^{14}$ are independently selected from a halogen, C1 to C10 alkyl, C1 to C10 alkyloxy, C1 to C10 alkylthio, aryl, heteroaryl, and C1 to C10 haloalkyl, α is an oxygen atom or a sulfur atom, $L^5$ is —(CH$_2$)v—, —C=C—, —C≡C—, —O—, or —S—, v is an integer from 0 to 2, β is —CH$_2$— or —(CH$_2$)$_2$—, γ is an oxygen atom or a sulfur atom, b is an integer from 0 to 3, d is an integer from 0 to 4, f, p, and w are independently an integer from 0 to 5, g is an integer from 0 to 2, r is an integer from 0 to 7, and u is an integer from 0 to 4, or is (e) a member of (d) substituted with at least one substituent selected from the group consisting of C1 to C6 alkyl, C1 to C6 alkyloxy, C1 to C6 haloalkyloxy, C1 to C6 haloalkyl, aryl, and a halogen;

$R^8$ is C1 to C3 alkyl, C2 to C3 alkenyl, C3 to C4 cycloalkyl, C3 to C4 cycloalkenyl, C1 to C2 haloalkyl, C1 to C3 alkyloxy, or C1 to C3 alkylthio;

$R^9$ is —(L$^3$)—R$^{15}$ wherein $L^3$ is represented by the formula:

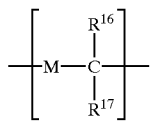

wherein M is —CH$_2$—, —O—, —N(R$^{24}$)—, or —S—, $R^{16}$ and $R^{17}$ are independently hydrogen atom, C1 to C10 alkyl, aryl, aralkyl, alkyloxy, haloalkyl, carboxy, or a halogen, and $R^{24}$ is hydrogen atom or C1 to C6 alkyl, and $R^{15}$ is represented by the formula:

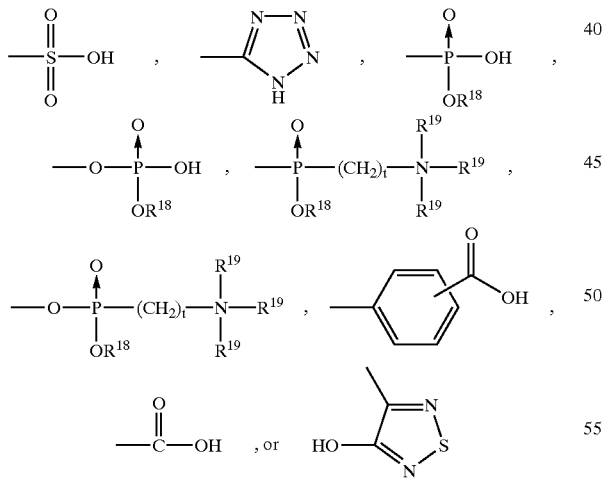

wherein $R^{18}$ is hydrogen atom, a metal, or C1 to C10 alkyl, $R^{19}$ is independently hydrogen atom, or C1 to C10 alkyl, and t is an integer from 1 to 8;

$R^{10}$ and $R^{11}$ are independently hydrogen atom or a non-interfering substituent selected from C1 to C8 alkyl, C2 to C8 alkenyl, C2 to C8 alkynyl, C7 to C12 aralkyl, C7 to C12 alkaryl, C3 to C8 cycloalkyl, C3 to C8 cycloalkenyl, phenyl, tolyl, xylyl, biphenylyl, C1 to C8 alkyloxy, C2 to C8 alkenyloxy, C2 to C8 alkynyloxy, C2 to C12 alkyloxyalkyl, C2 to C12 alkyloxyalkyloxy, C2 to C12 alkylcarbonyl, C2 to C12 alkylcarbonylamino, C2 to C12 alkyloxyamino, C2 to C12 alkyloxyaminocarbonyl, C1 to C12 alkylamino, C1 to C6 alkylthio, C2 to C12 alkylthiocarbonyl, C1 to C8 alkylsulfinyl, C1 to C8 alkylsulfonyl, C2 to C8 haloalkyloxy, C1 to C8 haloalkylsulfonyl, C2 to C8 haloalkyl, C1 to C8 hydroxyalkyl, —C(O)O(C1 to C8 alkyl), —(CH$_2$)$_z$—O—(C1 to C8 alkyl), benzyloxy, aryloxy, aryloxy C1 to C8 alkyl, arylthio, arylthio C1 to C8 alkyl, cyano C1 to C8 alkyl, —(CONHSO$_2$R$^{25}$), —CHO, amino, amidino, halogen, carbamyl, carboxyl, carbalkoxy, —(CH$_2$)$_z$—CO$_2$H, cyano, cyanoguanidinyl, guanidino, hydrazido, hydrazino, hydrazide, hydroxy, hydroxyamino, iodo, nitro, phosphono, —SO$_3$H, thioacetal, thiocarbonyl, or carbonyl, $R^{25}$ is C1 to C6 alkyl or aryl, z is an integer from 1 to 8; and $R^B$ is a group represented by the formula:

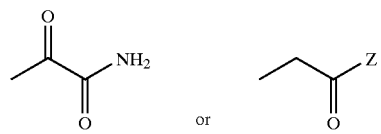

wherein Z is the same as defined above; the prodrugs thereof, or their pharmaceutically acceptable salts, or their solvates.

When the above b, d, f, p, r, u, and/or w are 2 or more, a plural number of $R^{13}$ or $R^{14}$ may be different from one another. When $R^{13}$ is a substituent on the naphthyl group, the substituent may be substituted at any arbitrary position on the naphthyl group.

iii) A compound, the prodrugs thereof, or their pharmaceutically acceptable salts, or their solvates as described in above i) or ii), wherein said $R^1$ and $R^7$ are independently represented by the formula:

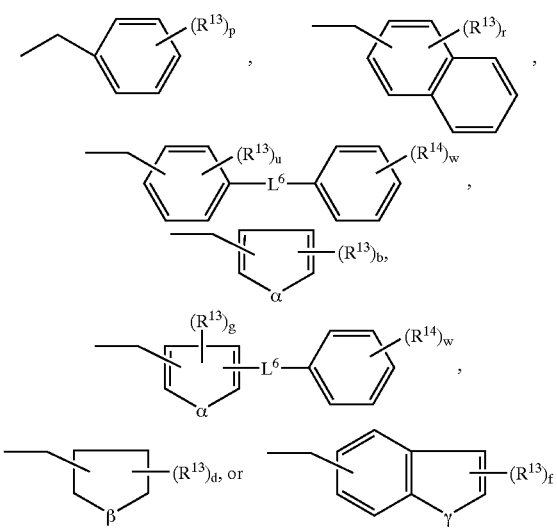

wherein $R^{13}$, $R^{14}$, b, d, f, g, p, r, u, w, α, β, and γ are the same as defined above, $L^6$ is a bond, —CH$_2$—, —C=C—, —C≡C—, —O—, or —S—.

When the above b, d, f, p, r, u, and/or w are 2 or more, a plural number of $R^{13}$ or $R^{14}$ may be different from one another. When $R^{13}$ is a substituent on the naphthyl group, the substituent may be substituted at any arbitrary position on the naphthyl group.

iv) A compound, the prodrugs thereof, or their pharmaceutically acceptable salts, or their solvates as described in any one of i) to iii), wherein $R^2$ and $R^8$ are C1 to C3 alkyl or C3 to C4 cycloalkyl.

v) A compound, the prodrugs thereof, or their pharmaceutically acceptable salts, or their solvates as described in any one of i) to iv), wherein the $L^2$ and $L^3$ are —O—CH$_2$—.

vi) A compound represented by the formula (III):

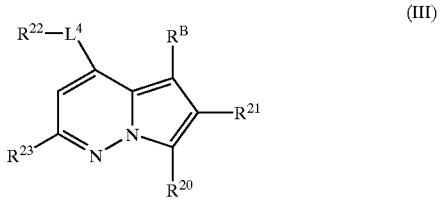

(III)

wherein $R^{20}$ is a group represented by the formula:

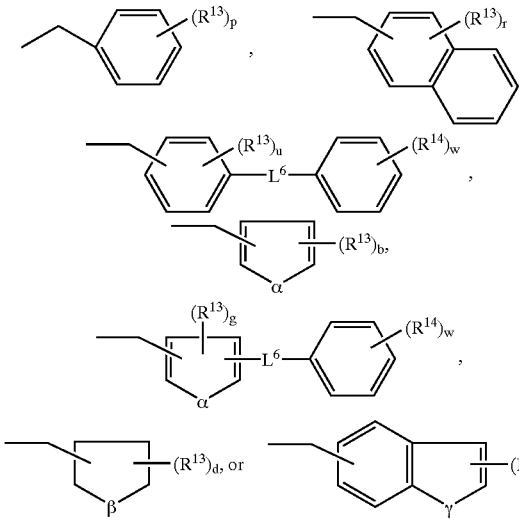

wherein $L^6$ is a bond, —CH$_2$—, —C═C—, —C≡C—, —O—, or —S—; $R^{13}$ and $R^{14}$ are independently selected from a halogen, C1 to C10 alkyl, C1 to C10 alkyloxy, C1 to C10 alkylthio, aryl, heteroaryl, and C1 to C10 haloalkyl; b is an integer from 0 to 3, d is an integer from 0 to 4, f, p, and w are independently an integer from 0 to 5, g is an integer from 0 to 2, r is an integer from 0 to 7, u is an integer from 0 to 4; α is an oxygen atom or a sulfur atom; β is —CH$_2$— or —(CH$_2$)$_2$—; and γ is an oxygen atom or a sulfur atom;

$R^{21}$ is C1 to C3 alkyl or C3 to C4 cycloalkyl;

$L^4$ is —O—CH$_2$—, —S—CH$_2$—, —N(R$^{24}$)—CH$_2$—, —CH$_2$—CH$_2$—, —O—CH(CH$_3$)—, or —O—CH((CH$_2$)$_2$Ph)— wherein $R^{24}$ is hydrogen atom or C1 to C6 alkyl and Ph is phenyl;

$R^{22}$ is —COOH, —SO$_3$H, or P(O)(OH)$_2$;

$R^{23}$ is hydrogen atom, C1 to C6 alkyl, C7 to C12 aralkyl, C1 to C6 alkyloxy, C1 to C6 alkylthio, C1 to C6 hydroxyalkyl, C2 to C6 haloalkyloxy, halogen, carboxy, C1 to C6 alkyloxycarbonyl, aryloxy, aryloxy C1 to C8 alkyl, arylthio, arylthio C1 to C8 alkyl, cyano C1 to C8 alkyl, a carbocyclic group, or a heterocyclic group; and $R^B$ is a group represented by the formula:

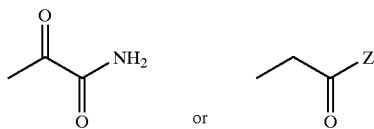

wherein Z is —NH$_2$ or —NHNH$_2$; the prodrugs thereof, or their pharmaceutically acceptable salts, or their solvates.

When the above b, d, f, p, r, u, and/or w are 2 or more, a plural number of $R^{13}$ or $R^{14}$ may be different from one another. When $R^{13}$ is a substituent on the naphthyl group, the substituent may be substituted at any arbitrary position on the naphthyl group.

vii) A compound represented by the formula (IV):

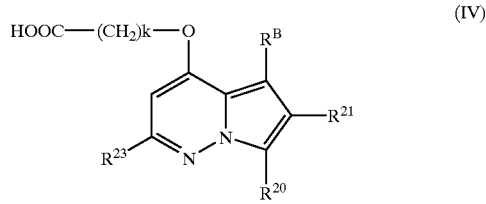

(IV)

wherein $R^{20}$ is a group represented by the formula:

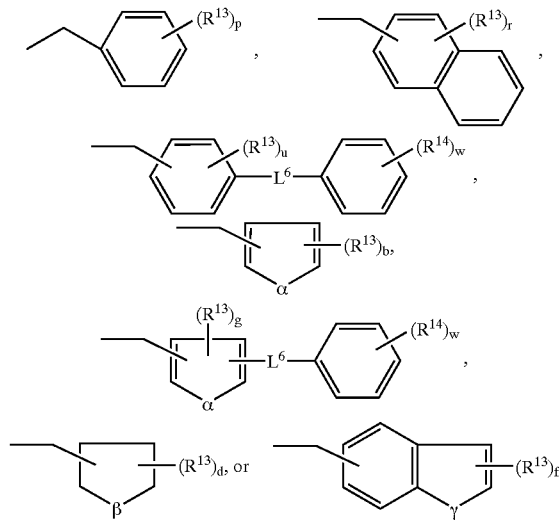

wherein $L^6$ is a bond, —CH$_2$—, —C═C—, —C≡C—, —O—, or —S—; $R^{13}$ and $R^{14}$ are independently selected from a halogen, C1 to C10 alkyl, C1 to C10 alkyloxy, C1 to C10 alkylthio, aryl, heteroaryl, and C1 to C10 haloalkyl; b is an integer from 0 to 3, d is an integer from 0 to 4, f, p, and w are independently an integer from 0 to 5, g is an integer from 0 to 2, r is an integer from 0 to 7, u is an integer from 0 to 4; α is an oxygen atom or a sulfur atom; β is —CH$_2$— or —(CH$_2$)$_2$—; and γ is an oxygen atom or a sulfur atom;

$R^{21}$ is C1 to C3 alkyl or C3 to C4 cycloalkyl;

$R^{23}$ is hydrogen atom, C1 to C6 alkyl, C7 to C12 aralkyl, C1 to C6 alkyloxy, C1 to C6 alkylthio, C1 to C6 hydroxyalkyl, C2 to C6 haloalkyloxy, halogen, carboxy, C1 to C6 alkyloxycarbonyl, aryloxy, aryloxy C1 to C8 alkyl, arylthio, arylthio C1 to C8 alkyl, cyano C1 to C8 alkyl, a carbocyclic group, or a heterocyclic group;

$R^B$ is a group represented by the formula:

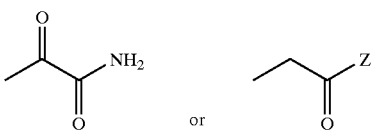

wherein Z is —NH$_2$ or —NHNH$_2$; and
k is an integer from 1 to 3; the prodrugs thereof, or their pharmaceutically acceptable salts, or their solvates.

viii) A compound, the prodrugs thereof, or their pharmaceutically acceptable salts, or their solvates as described in vi), wherein $L^4$ is —O—CH$_2$—.

ix) A compound, the prodrugs thereof, or their pharmaceutically acceptable salts, or their solvates as described in any one of i) to viii), wherein $R^A$ and $R^B$ are —COCONH$_2$—.

x) A compound, the prodrugs thereof, or their pharmaceutically acceptable salts, or their solvates as described in any one of i) to viii), wherein $R^A$ and $R^B$ are —CH$_2$CONH$_2$—.

xi) A compound, the prodrugs thereof, or their pharmaceutically acceptable salts, or their solvates as described in any one of i) to viii) wherein $R^A$ and $R^B$ are —CH$_2$CONHNH$_2$—.

xii) A prodrug as described in any one of i) to viii) which of an is ester type.

xiii) A pyrrolo[1,2-b]pyridazine compound selected from the group consisting of:
  Methyl (5-aminooxalyl-7-benzyl-6-ethylpyrrolo[1,2-b]pyridazine-4-yloxy)acetate,
  (5-aminooxalyl-7-benzyl-6-ethylpyrrolo[1,2-b]pyridazine-4-yloxy)acetic acid,
  Sodium (5-aminooxalyl-7-benzyl-6-ethylpyrrolo[1,2-b]pyridazine-4-yloxy)acetate,
  Methyl (5-aminooxalyl-7-benzyl-6-ethyl-2-methylpyrrolo[1,2-b]pyridazine-4-yloxy)acetate,
  (5-aminooxalyl-7-benzyl-6-ethyl-2-methylpyrrolo[1,2-b]pyridazine-4-yloxy)acetic acid,
  Methyl (5-aminooxalyl-7-benzyl-2,6-dimethylpyrrolo[1,2-b]pyridazine-4-yloxy) acetate,
  Ethyl (5-aminooxalyl-7-benzyl-2,6-dimethylpyrrolo[1,2-b]pyridazine-4-yloxy) acetate,
  2-(Morpholine4-yl)ethyl (5aminooxalyl-7-benzyl-2,6-dimethylpyrrolo[1,2-b]pyridazine-4-yloxy)acetate,
  (5-aminooxalyl-7-benzyl-2,6-dimethylpyrrolo[1,2-b]pyridazine-4-yloxy)acetic acid,
  Sodium (5-aminooxalyl-7-benzyl-2,6-dimethylpyrrolo[1,2-b]pyridazine-4-yloxy)acetate,
  Methyl (5-aminooxalyl-7-benzyl-6-methyl-2-phenylpyrrolo[1,2-b]pyridazine-4-yloxy)acetate,
  (5-aminooxalyl-7-benzyl-6-methyl-2-phenylpyrrolo[1,2-b]pyridazine-4-yloxy)acetic acid,
  Methyl (5-aminooxalyl-7-benzyl-6-ethyl-2-phenylpyrrolo[1,2-b]pyridazine-4-yloxy)acetate,
  (5-aminooxalyl-7-benzyl-6-ethyl-2-phenylpyrrolo[1,2-b]pyridazine-4-yloxy)acetic acid,
  Methyl [5-aminooxalyl-6-ethyl-7-(2-fluorobenzyl)-2-phenylpyrrolo[1,2-b]pyridazine-4-yloxy]acetate,
  [5-aminooxalyl-6-ethyl-7-(2-fluorobenzyl)-2-phenylpyrrolo[1,2-b]pyridazine-4-yloxy]acetic acid,
  Methyl [5-aminooxalyl-7-benzyl-6-ethyl-2-(4-fluorophenyl)pyrrolo[1,2-b]pyridazine-4-yloxy]acetate,
  [5-aminooxalyl-7-benzyl-6-ethyl-2-(4-fluorophenyl)pyrrolo[1,2-b]pyridazine-4-yloxy]acetic acid,
  Methyl (5-aminooxalyl-7-benzyl-6-ethyl-2-phenoxymethylpyrrolo[1,2-b]pyridazine-4-yloxy)acetate,
  (5-aminooxalyl-7-benzyl-6-ethyl-2-phenoxymethylpyrrolo[1,2-b]pyridazine4-yloxy)acetic acid,
  Methyl [5-aminooxalyl-7-benzyl-6-ethyl-2-(4-methoxyphenyl)pyrrolo[1,2-b]pyridazine-4-yloxy]acetate,
  [5-aminooxalyl-7-benzyl-6-ethyl-2-(4-methoxyphenyl)pyrrolo[1,2-b]pyridazine-4-yloxy]acetic acid,
  Methyl [5-aminooxalyl-6-ethyl-2-methyl-7-(2-phenylbenzyl)pyrrolo[1,2-b]pyridazine-4-yloxy]acetate,
  [5-aminooxalyl-6-ethyl-2-methyl-7-(2-phenylbenzyl)pyrrolo[1,2-b]pyridazine-4-yloxy]acetic acid,
  Methyl [5-aminooxalyl-6-ethyl-2-methyl-7-(3-phenoxybenzyl)pyrrolo[1,2-b]pyridazine-4-yloxy]acetate,
  [5-aminooxalyl-6-ethyl-2-methyl-7-(3 -phenoxybenzyl)pyrrolo[1,2-b]pyridazine-4-yloxy]acetic acid,
  Methyl (5-aminooxalyl-7-benzyl-6-methyl-2-propylpyrrolo[1,2-b]pyridazine-4-yloxy)acetate,
  (5-aminooxalyl-7-benzyl-6-methyl-2-propylpyrrolo[1,2-b]pyridazine-4-yloxy)acetic acid,
  Methyl (5-aminooxalyl-2,7-dibenzyl-6-methylpyrrolo[1,2-b]pyridazine-4-yloxy)acetate,
  (5-aminooxalyl-2,7-dibenzyl-6-methylpyrrolo[1,2-b]pyridazine-4-yloxy)acetic acid,
  Methyl [5-aminooxalyl-2,6-dimethyl-7-[2-(4-fluorophenyl)benzyl]pyrrolo[1,2-b]pyridazine-4-yloxy]acetate, and
  [5-aminooxalyl-2,6-dimethyl-7-[2-(4-fluorophenyl)benzyl]pyrrolo[1,2-b]pyridazine-4-yloxy]acetic acid,
and the prodrugs thereof; or their pharmaceutically acceptable salts; their parent acids; or their solvates.

xiv) A pyrrolo[1,2-b]pyridazine compound selected from the group consisting of:
  Methyl(5-aminooxalyl-7-benzyl-2,6-dimethylpyrrolo[1,2-b]pyridazine-4-yloxy)acetate,
  Ethyl (5-aminooxalyl-7-benzyl-2,6-dimethylpyrrolo[1,2-b]pyridazine4-yloxy)acetate,
  2-(Morpholine-4-yl)ethyl (5-aminooxalyl-7-benzyl-2,6-dimethylpyrrolo[1,2-b]pyridazine-4-yloxy)acetate,
  Sodium (5-aminooxalyl-7-benzyl-2,6-dimethylpyrrolo[1,2-b]pyridazine-4-yloxy)acetate,
  (5-aminooxalyl-7-benzyl-2,6-dimethylpyrrolo[1,2-b]pyridazine-4-yloxy)acetic acid,
  Methyl (5-aminooxalyl-7-benzyl-6-methyl-2-phenylpyrrolo[1,2-b]pyridazine-4-yloxy)acetate,
  Ethyl (5-aminooxalyl-7-benzyl-6-methyl-2-phenylpyrrolo[1,2-b]pyridazine-4-yloxy)acetate,
  2-(Morpholine-4-yl)ethyl (5-aminooxalyl-7-benzyl-6-methyl-2-phenylpyrrolo [1,2-b]pyridazine-4-yloxy)acetate,
  Sodium (5-aminooxalyl-7-benzyl-6-methyl-2-phenylpyrrolo[1,2-b]pyridazine-4-yloxy)acetate,
  (5-aminooxalyl-7-benzyl-6-methyl-2-phenylpyrrolo[1,2-b]pyridazine-4-yloxy)acetic acid,
  Methyl (5-aminooxalyl-7-benzyl-6-ethyl-2-phenoxymethylpyrrolo[1,2-b]pyridazine-4-yloxy) acetate, Ethyl (5-aminooxalyl-7-benzyl-6-ethyl-2-phenoxymethylpyrrolo[1,2-b]pyridazine-4-yloxy) acetate, 2-(Morpholine-4-yl)ethyl 5-aminooxalyl-7-benzyl-6-ethyl-2-phenoxymethylpyrrolo[1,2-b]pyridazine-4-yloxy)acetate, Sodium (5-aminooxalyl-7-benzyl-6-ethyl-2-phenoxymethylpyrrolo[1,2-b]pyridazine-4-yloxy) acetate, (5-aminooxalyl-7-benzyl-6-ethyl-2-phenoxymethylpyrrolo[1,2-b]pyridazine-4-yloxy) acetic acid, Methyl[5-aminooxalyl-6-ethyl-2-methyl-7-(2-phenylbenzyl)pyrrolo[1,2-b]pyridazine-4-yloxy] acetate, Ethyl [5-aminooxalyl-6-ethyl-2-methyl-7-(2-phenylbenzyl)pyrrolo[1,2-b]pyridazine-4-yloxy] acetate, 2-(Morpholine-4-yl)ethyl 5-aminooxalyl-6-ethyl-2-methyl-7-(2-phenylbenzyl)pyrrolo[1,2-b]pyridazine-4-yloxy)acetate, Sodium[5-aminooxalyl-6-ethyl-2-methyl-7-(2-phenylbenzyl)pyrrolo[1,2-b]pyridazine-4-yloxy] acetate, (5-aminooxalyl-6-ethyl-2-methyl-7-(2-phenylbenzyl) pyrrolo[1,2-b]pyridazine-4-yloxy)acetic acid, Methyl(5-aminooxalyl-7-benzyl-6-methyl-2-propylpyrrolo[1,2-b]pyridazine-4-yloxy)acetate, Ethyl(5-aminooxalyl-7-benzyl-6-methyl-2-propylpyrrolo[1,2-b]pyridazine-4-yloxy)acetate, 2-(Morpholine-4-yl)ethyl 5-aminooxalyl-7-benzyl-6-methyl-2-propylpyrrolo[1,2-b]pyridazine-4-yloxy) acetate, Sodium (5-aminooxalyl-7-benzyl-6-methyl-2-propylpyrrolo[1,2-b]pyridazine-4-yloxy)acetate, and (5-aminooxalyl-7-benzyl-6-methyl-2-propylpyrrolo [1,2-b]pyridazine-4-yloxy) acetic acid, and the prodrugs thereof; or their pharmaceutically acceptable salts; their parent acids; or their solvates.

xv) A pharmaceutical composition containing as active ingredient a compound as described in any one of i) to xiv).

xvi) A pharmaceutical composition as described in xv), which is for inhibiting sPLA$_2$.

xvii) A pharmaceutical composition as described in xv), which is for treatment or prevention of Inflammatory Diseases.

xviii) A method of inhibiting sPLA$_2$ mediated release of fatty acid which comprises contacting sPLA$_2$ with a therapeutically effective amount of a pyrrolo[1,2-b]pyridazine compound as described in i).

xix) A method of treating a mammal, including a human, to alleviate the pathological effects of Inflammatory Diseases; wherein the method comprises administration to said mammal of a pyrrolo[1,2-b]pyridazine compound as described in i).

xx) A compound as described in i) or a pharmaceutical formulation containing an effective amount of a pyrrolo[1,2-b]pyridazine compound as described in i) for use in treatment of Inflammatory Diseases.

xxi) A compound as described in i) or a pharmaceutical formulation containing an effective amount of a pyrrolo[1,2-b]pyridazine compound as described in i) for use as an inhibitor for inhibiting sPLA$_2$ mediated release of fatty acid.

xxii) A pyrrolo[1,2-b]pyridazine sPLA$_2$ inhibitor substantially as hereinbefore described with reference to any of the Examples.

xxiii) A compound represented by the formula (XII):

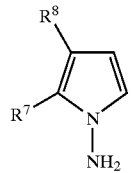

(XII)

wherein $R^7$ is —$(CH_2)m$—$R^{12}$ wherein m is an integer from 1 to 6, and $R^{12}$ is (d) a group represented by the formula:

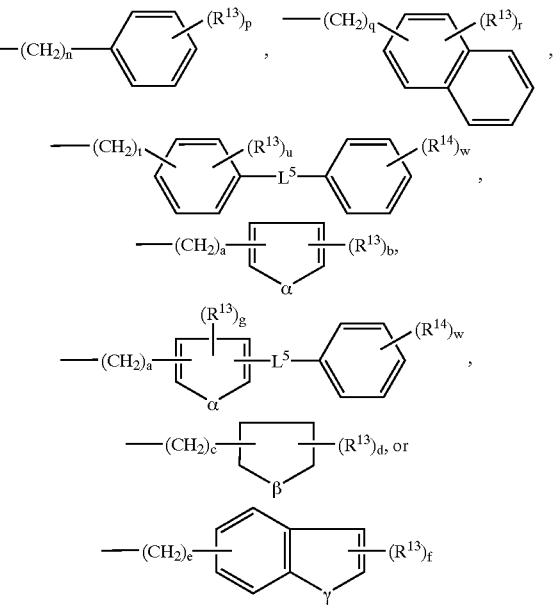

wherein a, c, e, n, q, and t are independently an integer from 0 to 2, $R^{13}$ and $R^{14}$ are independently selected from a halogen, C1 to C10 alkyl, C1 to C10 alkyloxy, C1 to C10 alkylthio, aryl, heteroaryl, and C1 to C10 haloalkyl, a is an oxygen atom or a sulfur atom, $L^5$ is —$(CH_2)v$—, —C=C—, —C≡C—, —O—, or —S—, v is an integer from 0 to 2, β is —$CH_2$— or —$(CH_2)_2$—, γ is an oxygen atom or a sulfur atom, b is an integer from 0 to 3, d is an integer from 0 to 4, f, p, and w are independently an integer from 0 to 5, g is an integer from 0 to 2, r is an integer from 0 to 7, and u is an integer from 0 to 4, or is (e) a member of (d) substituted with at least one substituent selected from the group consisting of C1 to C6 alkyl, C1 to C6 alkyloxy, C1 to C6 haloalkyloxy, C1 to C6 haloalkyl, aryl, and a halogen; and $R^1$ is C1 to C3 alkyl, C2 to C3 alkenyl, C3 to C4 cycloalkyl, C3 to C4 cycloalkenyl, C1 to C2 haloalkyl, C1 to C3 alkyloxy, or C1 to C3 alkylthio.

In the present specification, the term "alkyl" employed alone or in combination with other terms means a straight- or branched chain monovalent hydrocarbon group having a specified number of carbon atoms. An example of the alkyl includes methyl, ethyl, n-propyl, isopropyl, n-butyl, isobutyl, sec-butyl, tert-butyl, n-pentyl, n-hexyl, n-heptyl, n-octyl, n-nonyl, n-decanyl, n-undecanyl, n-dodecanyl, n-tridecanyl, n-tetradecanyl, n-pentadecanyl, n-hexadecanyl, n-heptadecanyl, n-octadecanyl, n-nonadecanyl, n-eicosanyl and the like.

The term "alkenyl" employed alone or in combination with other terms in the present specification means a straight- or branched chain monovalent hydrocarbon group having a specified number of carbon atoms and at least one double bond. An example of the alkenyl includes vinyl, allyl, propenyl, crotonyl, isopentenyl, a variety of butenyl isomers and the like.

The term "alkynyl" used in the present specification means a straight or branched chain monovalent hydrocarbon group having a specified number of carbon atoms and at least one triple bond. The alkynyl may contain (a) double bond(s). An example of the alkynyl includes ethynyl, propynyl, 6-heptynyl, 7-octynyl, 8-nonynyl and the like.

The term "carbocyclic group" used in the present specification means a group derived from a saturated or unsaturated, substituted or unsubstituted 5 to 14 membered, preferably 5 to 10 membered, and more preferably 5 to 7 membered organic nucleus whose ring forming atoms (other than hydrogen atoms) are solely carbon atoms. A group containing two to three of the carbocyclic group is also included in the above stated group. An example of typical carbocyclic groups includes (f) cycloalkyl (such as cyclopropyl, cyclobutyl, cyclopentyl, cyclohexyl, cycloheptyl, and cyclooctyl); cycloalkenyl (such as cyclobutylenyl, cyclopentenyl, cyclohexenyl, cycloheptenyl, and cyclooptenyl); phenyl, spiro[5,5]undecanyl, naphthyl, norbornyl, bicycloheptadienyl, tolyl, xylyl, indenyl, stilbenyl, terphenylyl, diphenylethylenyl, phenylcyclohexenyl, acenaphthyl, anthoryl, biphenylyl, bibenzylyl, and a phenylalkylphenyl derivative represented by the formula:

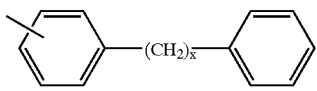
(V)

wherein x is an integer from 1 to 8.

The term "spiro[5,5]undecanyl" refers to the group represented by the formula:

Phenyl, cyclohexyl or the like is preferred as a carbocyclic groups in the $R^4$ and $R^5$.

The term "heterocyclic group" used in the present specification means a group derived from monocyclic or polycyclic, saturated or unsaturated, substituted or unsubstituted heterocyclic nucleus having 5 to 14 ring atoms and containing 1 to 3 hetero atoms selected from the group consisting of nitrogen atom, oxygen atom, and sulfur atom. An example of the heterocyclic group includes pyridyl, pyrrolyl, pyrrolidinyl, piperidinyl, furyl, benzofuryl, thienyl, benzothienyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, dibenzothiophenyl, indazolyl, imidazo[1,2-a]pyridinyl, benzotriazolyl, anthranilyl, 1,2-benzisoxazolyl, benzoxazolyl, benzothiazolyl, purinyl, puridinyl, dipyridinyl, phenylpyridinyl, benzylpyridinyl, pyrimidinyl, phenylpyrimidinyl, pyrazinyl, 1,3,5-triazinyl, quinolyl, phthalazinyl, quinazolinyl, quinoxalinyl, morpholino, thiomorpholino, homopiperazinyl, tetrahydrofuranyl, tetrahydropyranyl, oxacanyl, 1,3-dioxolanyl, 1,3-dioxanyl, 1,4-dioxanyl, 1,4-thioxanyl, azetidinyl, hexamethyleneiminium, heptamethyleneiminium, piperazinyl and the like.

Furyl, thienyl or the like is preferred as a heterocyclic group in the $R^4$ and $R^5$.

Preferred carbocyclic and heterocyclic groups in $R^1$ are (g) a group represented by the formula:

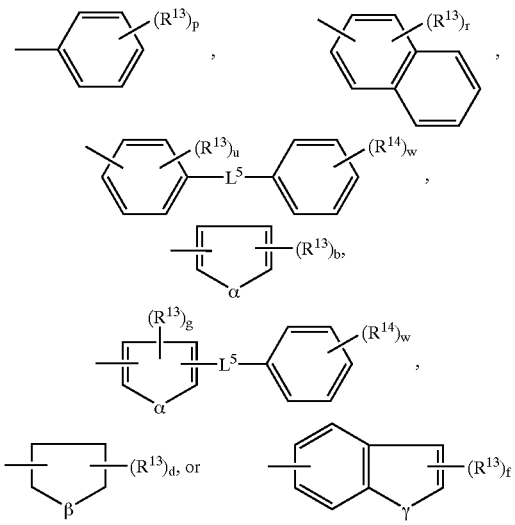

wherein $R^{13}$ and $R^{14}$ are independently selected from a halogen, C1 to C10 alkyl, C1 to C10 alkyloxy, C1 to C10 alkylthio, aryl, heteroaryl, and C1 to C10 haloalkyl, α is an oxygen atom or a sulfur atom, $L^5$ is —(CH$_2$)v—, —C=C—, —C≡C—, —O—, or —S—, v is an integer from 0 to 2; β is —CH$_2$— or —(CH$_2$)$_2$—; γ is an oxygen atom or a sulfur atom; b is an integer from 0 to 3, d is an integer from 0 to 4; f, p, and w are an integer from 0 to 5; r is an integer from 0 to 7, and u is an integer from 0 to 4. When the above b, d, f, p, r, u, and/or w are 2 or more, a plural number of $R^{13}$ or $R^{14}$ may be different from one another. When $R^{13}$ is a substituent on the naphthyl group, the substituent may be substituted at any arbitrary position on the naphthyl group. A more preferable example includes (h) a group represented by the formula:

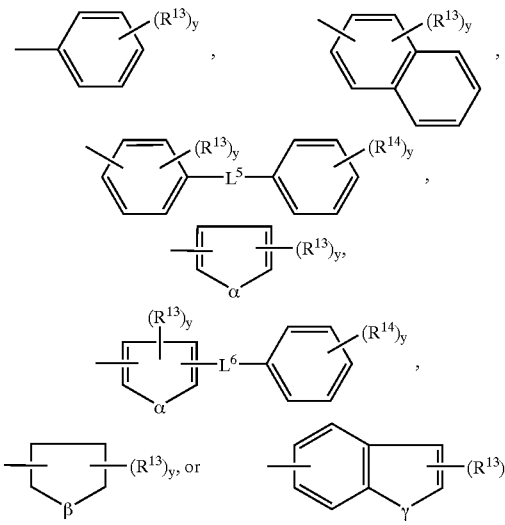

wherein $R^{13}$, $R^{14}$, α, β, and γ are the same as defined above, $L^6$ is —CH$_2$—, —C=C—, —C≡C—, —O—, or —S—, and y is 0 or 1. When $R^{13}$ is a substituent on the naphthyl group, the substituent may be substituted at any arbitrary position on the naphthyl group.

The "pyrrolo[1,2-b]pyridazine nucleus" is represented by the following structural formula together its numerical ring position for substituent placement:

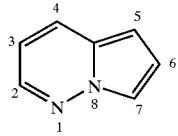

The term "non-interfering substituent" in the present specification means C1 to C8 alkyl, C2 to C8 alkenyl, C2 to C8 alkynyl, C7 to C12 aralkyl (such as benzyl and phenethyl), C7 to C12 alkaryl, C2 to C8 alkenyloxy, C2 to C8 alkynyloxy, C3 to C8 cycloalkyl, C3 to C8 cycloalkenyl, phenyl, tolyl, xylyl, biphenylyl, C1 to C8 alkyloxy, C2 to C12 alkyloxyalkyl (such as methyloxymethyl, ethyloxymethyl, methyloxyethyl, and ethyloxyethyl), C2 to C12 alkyloxyalkyloxy (such as methyloxymethyloxy and methyloxyethyloxy), C2 to C12 alkylcarbonyl (such as methycarbonyl and ethylcarbonyl), C2 to C12 alkycarbonylamino (such as methylcarbonylamino and ethylcarbonylamino), C2 to C12 alkyloxyamino (such as methyloxyamino and ethyloxyamino), C2 to C12 alkyloxyaminocarbonyl (such as methyloxyaminocarbonyl and ethyloxyaminocarbonyl), C1 to C12 alkylamino (such as methylamino, ethylamino, dimethylamino, and ethylmethylamino), C1 to C6 alkylthio, C2 to C12 alkylthiocarbonyl (such as methylthiocarbonyl and ethyltiocarbonyl), C1 to C8 alkylsulfinyl (such as methylsulfinyl and ethylsulfinyl), C1 to C8 alkylsulfonyl (such as methylsulfonyl and ethylsulfonyl), C2 to c8 haloalkyloxy (such as 2-chloroethyloxy and 2-bromoethyloxy), C1 to C8 haloalkysulfonyl (such as chloromethylsulfonyl and bromomethylsulfonyl), C2 to C8 haloalkyl, C1 to C8 hydroxyalkyl (such as hydroxymethyl and hydroxyethyl), —C(O)O(C1 to C8 alkyl) (such as methyloxycarbonyl and ethyloxycarbonyl, —($CH_2$)z—O—(C1 to C8 alkyl), benzyloxy, aryloxy (such as phenyloxy), arylthio (such as phenylthio), —(CONH$SO_2R^{25}$), —CHO, amino, amidino, halogen, carbamyl, carboxyl, carbalkyloxy, —($CH_2$)z—COOH (such as carboxymethyl, carboxyethyl, and carboxypropyl), cyano, cyanoguanidino, guanidino, hydrazido, hydroxy, hydroxyamino, nitro, phosphono, —$SO_3H$, carbocyclic groups, heterocyclic groups wherein z is an integer from 1 to 8 and $R^{25}$ is C1 to C6 alkyl or aryl. These groups may be substituted by at least one substituent selected from the group consisting of C1 to C6 alkyl, C1 to C6 alkyloxy, C2 to C6 haloalkyloxy, C1 to C6 haloalkyl, and halogens.

Preferable are halogens, C1 to C6 alkyl, C1 to C6 alkyloxy, C1 to C6 alkylthio, and C1 to C6 haloalkyl as the "non-interfering substituent" in the $R^1$. More preferable are halogens, C1 to C3 alkyl, C1 to C3 alkyloxy, C1 to C3 alkylthio, and C1 to C3 haloalkyl.

Preferable are (i) C1 to C6 alkyl, aralkyl, C1 to C6 alkyloxy, C1 to C6 alkylthio, C1 to C6 hydroxyalkyl, C2 to C6 haloalkyloxy, halogens, carboxy, C1 to C6 alkyloxycarbonyl, aryloxy, arylthio, carbocyclic groups, and heterocyclic groups as the "non-interfering substituents" in the $R^4$, $R^5$, $R^{10}$, and $R^{11}$. More preferable are (j) C1 to C6 alkyl, aralkyl, carboxy, C1 to C6 hydroxyalkyl, phenyl, and C1 to C6 alkyloxycarbonyl.

The term "halogen" in the present specification means fluorine, chlorine, bromine, and iodine.

The term "cycloalkyl" in the present specification means a monovalent cyclic hydrocarbon group having a specified number of carbon atoms. An example of the cycloalkyl includes cyclopropyl, cyclobutyl, cyclopentyl, cyclohexyl, cycloheptyl, cyclooctyl and the like.

The term "cycloalkenyl" in the present specification means a monovalent cyclic hydrocarbon group having a specified number of carbon atoms and at least one double bond(s). An example of the cycloalkenyl includes 1-cyclopropenyl, 2-cyclopropenyl, 1-cyclobutenyl, 2-cyclobutenyl and the like.

In the present specification, an example of "alkyloxy" includes methyloxy, ethyloxy, n-propyloxy, isopropyloxy, n-butyloxy, n-pentyloxy, n-hexyloxy and the like.

In the present specification, an example of "alkylthio" includes methylthio, ethylthio, n-propylthio, isopropylthio, n-butylthio, n-pentylthio, n-hexylthio and the like.

The term "acidic group" in the present specification means an organic group functioning as a proton donor capable of hydrogen bonding when attached to a pyrrolo[1,2-b]pyridazine nucleus through a suitable linking atom (hereinafter defined as "acid linker"). An example of the acidic group includes (k) a group represented by the formula:

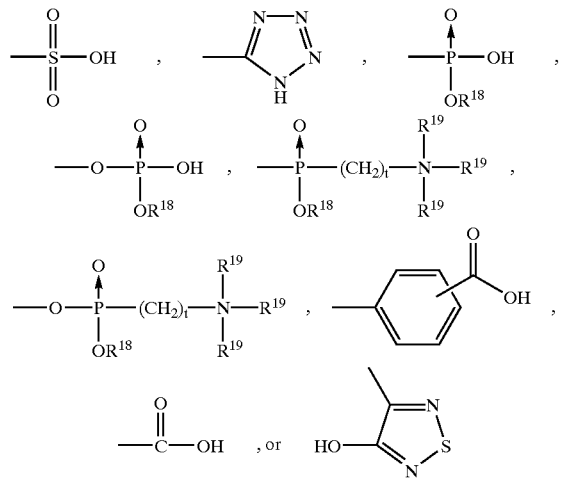

wherein $R^{18}$ is hydrogen atom, a metal, or C1 to C10 alkyl and each $R^{19}$ is independently hydrogen atom or C1 to C10 alkyl. Preferable is (1) —COOH, —$SO_3H$, or P(O)(OH)$_2$. More preferable is (m)—COOH.

The term "acid linker" in the present specification means a divalent linking group represented by a symbol —($L^2$)—, and it functions to join 4-position of pyrrolo[1,2-b]pyridazine nucleus to an "acidic group" in the general relationship. An example of it includes (n) a group represented by the formula:

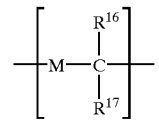

M is —$CH_2$—, —O—, —N($R^{24}$)—, or —S—, and $R^{16}$ and $R^{17}$ are independently hydrogen atom, C1 to C10 alkyl, aryl, aralkyl, carboxy, or halogens. Preferable are (o) —O—$CH_2$—, —S—$CH_2$—, —N($R^{24}$)—$CH_2$—, —$CH_2$—$CH_2$—, —O—CH($CH_3$)—, or —O—CH(($CH_2$)$_2$Ph)— wherein $R^{24}$ is hydrogen atom or C1 to C6 alkyl and Ph is phenyl. More preferable is (p) —O—$CH_2$— or —S—$CH_2$—.

In the present specification, the term "acid linker length" means the number of atoms (except for hydrogen atoms) in the shortest chain of a linking group —(L²)— which connects 4-position in pyrrolo[1,2-b]pyridazine nucleus with the "acidic group". The presence of a carbocyclic ring in (L² counts as the number of atoms approximately equivalent to the calculated diameter of the carbocyclic ring. Thus, a benzene and cyclohexane ring in the acid linker counts as two atoms in culculating the length of —(L²)—. preferable length is 2 to 3.

A symbol k in the formula (IV) is preferably 1.

The term "haloalkyl" in the present specification means the above described "alkyl" substituted with the above described "halogen" at arbitrary position(s). An example of the haloalkyl includes chloromethyl, trifluoromethyl, 2-chloromethyl, 2-bromomethyl and the like.

The term "hydroxyalkyl" in the present specification means the aforementioned "alkyl" substituted with hydroxy at arbitrary position(s). An example of the hydroxyalkyl includes hydroxymethyl, 2-hydroxyethyl, 3-hydroxypropyl and the like. In this case, hydroxymethyl is preferable.

In the present specification, the term "haloalkyl" in "haloalkyloxy" is the same as defined above. An example of it includes 2-chloroethyloxy, 2,2,2-trifluoroethyloxy, 2-chloroethyloxy and the like.

The term "aryl" in the present specification means a monocyclic or condensed cyclic aromatic hydrocarbon. An example of the aryl includes phenyl, 1-naphthyl, 2-naphthyl, anthryl and the like. Particularly, phenyl and 1-naphthyl are preferred. Such "aryl" is optionally substituted with C1 to C6 alkyl, hydroxy, C1 to C3 alkyloxy, halogen, nitro, substituted or unsubstituted amino, cyano, C1 to C3 haloalkyl, and the like at one or more position(s).

The term "aralkyl" in the present specification means a group wherein the aforementioned "alkl" is substituted with the above-mentioned "aryl". Such aryl may have a bond at any substitutable position. An example of it includes benzyl, phenethyl, phenylpropyl (such as 3-phenylpropyl), naphthylmethyl (such as 1-naphthylmethyl) and the like.

The term "group containing 1 to 4 non-hydrogen atoms" refers to relatively small groups which form substituents at the 6 position of the pyrrolo[1,2-b]pyridazine nucleus, said groups may contain non-hydrogen atoms alone, or non-hydrogen atoms plus hydrogen atoms as required to satisfy the unsubstituted valence of the non-hydrogen atoms, for example; (ii) groups absent hydrogen which contain no more than 4 non-hydrogen atoms such as —CF$_3$, —Cl, —Br, —NO$_2$, —CN, —SO$_3$; and (iii) groups having hydrogen atoms which contain less than 4 non-hydrogen atoms such as —CH$_3$, —C$_2$H$_5$, —CH=CH$_2$, —CH(CH$_3$)$_2$, and cyclopropyl.

An example of the "alkyloxycarbonyl" in the present specification includes methyloxycarbonyl, ethyloxycarbonyl, n-propyloxycarbonyl and the like.

The term "substituted amino" in the present specification includes amino substituted with C1 to C6 alkyl, aralkl, C1 to C6 alkylcarbonyl, C1 to C6 alkyloxycarbonyl, and the like at one or two position(s).

Preferred embodiments of the R$^7$ of the formula (XXII) are C5 to C8 cycloalkylmethyl and phenylmethyl which is optionally substituted with halogen, C1 to C6 alkyl, aryl, alkyloxy, or aryloxy.

Preferable is C1 to C6 alkyl as the R$^8$ of the formula (XXII).

A group of preferable substituents as the R$^1$ to R$^5$ and the R$^A$ of the compound represented by the formula (I) will be shown in items (A) to (W). Items (f) to (m) are the same group as described above.

As the R$^1$, (A): —(L$^1$)—R$^6$, (B): —(CH$_2$)$_{1-2}$-(f), (C): —(CH$_2$)$_{1-2}$-(g), and (D): —(CH$_2$)$_{1-2}$-(h) are preferred.

As the R$^2$, (E): hydrogen atom, halogen, C1 to C3 alkyl, C3 to C4 cycloalkyl, or C1 to C3 alkyloxy; and (F): C1 to C3 alkyl or C3 to C4 cycloalkyl are preferred.

As the R$^A$, (G): —C(=O)—C(=O)—NH$_2$, —CH$_2$C(=O)—NH$_2$, or —CH$_2$C(=O)—NHNH$_2$; and (H): —C(=O)—C(=O)—NH$_2$ are preferred.

As the R$^3$, (I): -(n)-(k), (J): -(n)-(l), (K): -(n)-(m), (L): -(o)-(k), (M): -(o)-(l), (N): -(o)-(m), (O): -(p)-(k), (P): -(p)-(l), and (Q): -(p)-(m) are preferred.

As the R$^4$, (R): hydrogen atom or non-interfering substituent, (S): hydrogen atom or (i), and (T): hydrogen atom or (j) are preferred.

As the R$^5$, (U): hydrogen atom or (i), (V): hydrogen atom or (j), and (W): hydrogen atom are preferred.

A preferred group of compounds represented by the formula (I) is shown below.

(R$^1$,R$^2$,R$^A$,R$^4$,R$^5$)=(A,E,G,R,U), (A,E,G,R,V), (A,E,G,R,W), (A,E,G,S,U), (A,E,G,S,V), (A,E,G,S,W), (A,E,G,T,U), (A,E,G,T,V), (A,E,G,T,W), (A,E,H,R,U), (A,E,H,R,V), (A,E,H,R,W), (A,E,H,S,U), (A,E,H,S,V), (A,E,H,S,W), (A,E,H,T,U), (A,E,H,T,V), (A,E,H,T,W), (A,F,G,R,U), (A,F,G,R,V), (A,F,G,R,W), (A,F,G,S,U), (A,F,G,S,V), (A,F,G,S,W), (A,F,G,T,U), (A,F,G,T,V), (A,F,G,T,W), (A,F,H,U), (A,F,H,R,V), (A,F,H,R,W), (A,F,H,S,U), (A,F,H,S,V), (A,F,H,S,W), (A,F,H,T,U), (A,F,H,T,V), (A,F,H,T,W), (B,E,G,R,U), (B,E,G,R,V), (B,E,G,R,W), (B,E,G,S,U), (B,E,G,S,V), (B,E,G,S,W), (B,E,G,T,U), (B,E,G,T,V), (B,E,G,T,W), (B,E,H,R,U), (B,E,H,R,V), (B,E,H,R,W), (B,E,H,S,U), (B,E,H,S,V), (B,E,H,S,W), (B,E,H,T,U), (B,E,H,T,V), (B,E,H,W), (B,F,G,R,U), (B,F,G,R,V), (B,F,G,R,W), (B,F,G,S,U), (B,F,G,S,V), (B,F,G,S,W), (B,F,G,T,U), (B,F,G,T,V), (B,F,G,T,W), (B,F,H,R,U), (B,F,H,R,V), (B,F,H,R,W), (B,F,KS,U), (B,F,H,S,V), (B,F,H,S,W), (B,F,H,T,U), (B,F,H,T,V), (B,F,H,T,W), (C,E,G,R,U), (C,E,G,R,V), (C,E,G,R,W), (C,E,G,S,U), (C,E,G,S,V), (C,E,G,S,W), (C,E,G,T,U), (C,E,G,T,V), (C,E,G,T,W), (C,E,H,R,U), (C,E,H,R,V), (C,E,H,R,W), (C,E,H,S,U), (C,E,H,S,V), (C,E,H,S,W), (C,E,H,T,U), (C,E,H,T,V), (C,E,H,T,W), (C,F,G,R,U), (C,F,G,R,V), (C,F,G,R,W), (C,F,G,S,U), (C,F,G,S,V), (C,F,G,S,W), (C,F,G,T,U), (C,F,G,T,V), (C,F,G,T,W), (C,F,H,R,U), (C,F,H,R,V), (C,F,H,R,W), (C,F,H,S,U), (C,F,H,S,V), (C,F,H,S,W), (C,F,H,T,U), (C,F,H,T,V), (C,F,H,T,W), (D,E,G,R,U), (D,E,G,R,V), (D,E,G,R,W), (D,E,G,S,U), (D,E,G,S,V), (D,E,G,S,W), (D,E,G,T,U), (D,E,G,T,V), (D,E,G,T,W), (D,E,H,R,U), (D,E,H,R,V), (D,E,H,R,W), (D,E,H,S,U), (D,E,H,S,V), (D,E,H,S,W), (D,E,H,T,U), (D,E,H,T,V), (D,E,H,T,W), (D,F,G,R,U), (D,F,G,R,V), (D,F,G,R,W), (D,F,G,S,U), (D,F,G,S,V), (D,F,G,S,W), (D,F,G,T,U), (D,F,G,T,V), (D,F,G,T,W), (D,F,H,R,U), (D,F,H,R,V), (D,F,H,R,W), (D,F,H,S,U), (D,F,H,S,V), (D,F,H,S,W), (D,F,H,T,U), (D,F,H,T,V), and (D,F,H,T,W).

Preferred embodiments of this invention are compounds wherein R$^3$ is any one of (I) to (Q) and (R$^1$,R$^2$,R$^A$,R$^4$,R$^5$) is any one of the above combinations.

The term, "Inflammatory Diseases" refers to diseases such as inflammatory bowel disease, sepsis, septic shock, adult respiratory distress syndrome, pancreatitis, trauma-induced shock, bronchial asthma, allergic rhinitis, rheumatoid arthritis, chronic rheumatism, arterial sclerosis, cereberal hemorrhage, cerebral infarction, cardiac failure, cardiac infarction, psoriasis, cystic fibrosis, stroke, acute bronchitis, chronic bronchitis, acute bronchiolitis, chronic bronchiolitis, osteoarthritis, gout, spondylarthropathris, ankylosing spondylitis, Reiter's syndrome, psoriatic arthropathy, enterapathric spondylitis, Juvenile arthropathy or juvenile ankylosing spondylitis, Reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury (typing), miscellaneous forms of arthritis, neuropathic joint disease (charco and joint), hemarthrosis (hemarthrosic), Henoch-Schonlein Purpura, hypertrophic osteoarthropathy, multicentric reticulohistiocytosis, arthritis associated with certain diseases, surcoilosis, hemochromatosis, sickle cell disease and other hemoglobinopathries, hyperlipoproteineimia, hypogammaglobulinemia, hyperparathyroidism, acromegaly, familial Mediterranean fever, Behat's Disease, systemic lupus erythrematosis, or relapsing polychondritis and related diseases which comprises administering to a mammal in need of such treatment a therapeutically effective amount of the compound of formula I in an amount sufficient to inhibit sPLA$_2$ mediated release of fatty acid and to thereby inhibit or prevent the arachidonic acid cascade and its deleterious products.

The terms, "mammal" and "mammalian" include human.

The term "solvate" includes, for example, solvates with organic solvents, hydrates, and the like.

BEST MODE FOR CARRYING OUT THE INVENTION

The compounds of the invention represented by the formula (I) can be synthesized in accordance with the following method A. The compound (XV) in the method A can be also synthesized in accordance with the following method B.

(Method A)

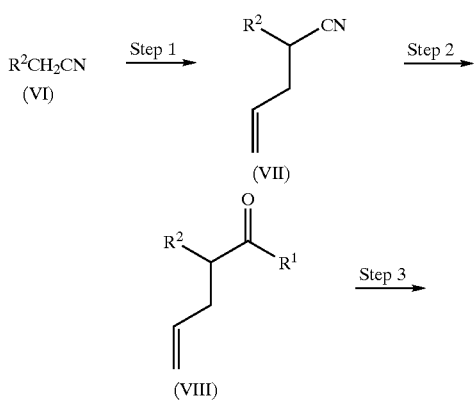

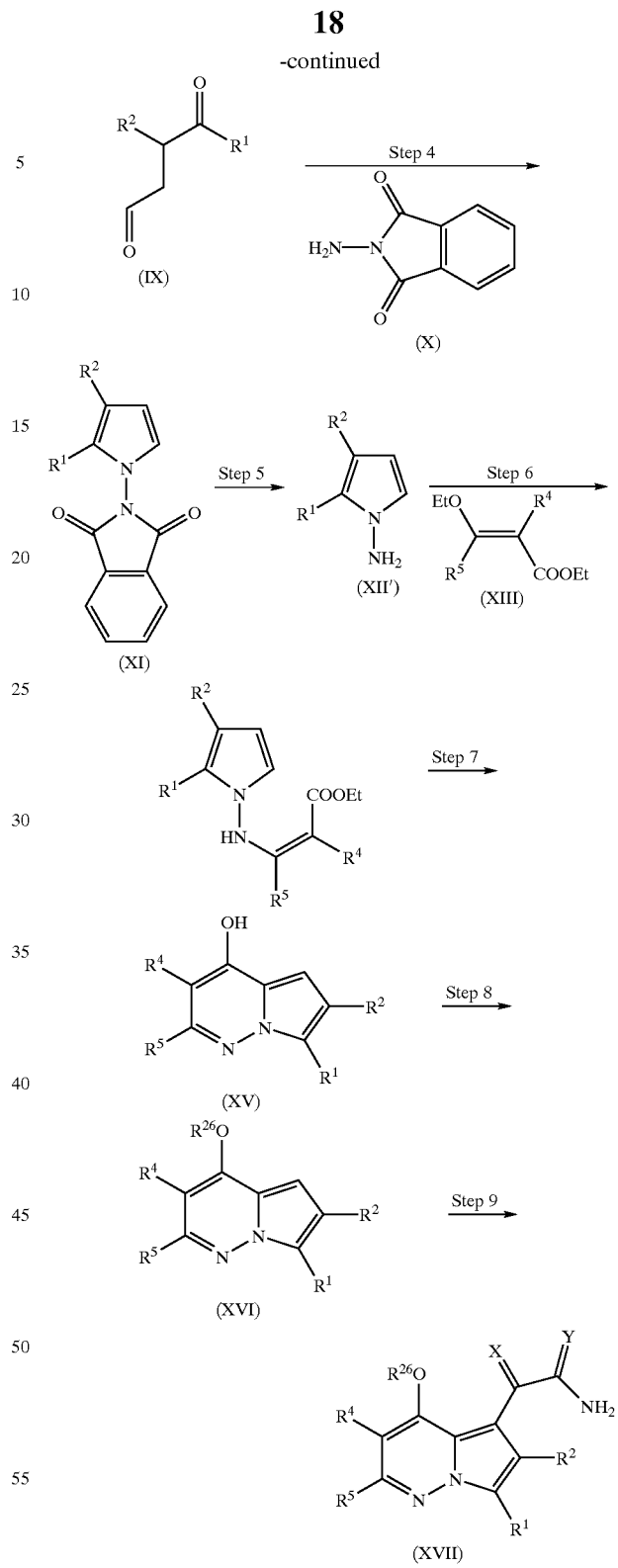

wherein $R^1$, $R^2$, $R^4$, $R^5$, X, and Y are as defined above; $R^{26}$ is an acidic group.

(Step 1)

To a solution of the compound (VI) which is commercially available or is synthesized in accordance with well-known method in a solvent such as tetrahydrofuran, diethyl ether, and ethylene glycol dimethyl ether is added a base such as lithium diisopropyl amide and n-butyllithium at −78° C., to −20° C., preferably −78° C. to −60° C. To the reaction mixture is added alkenyl halide such as allyl bromide and allyl chloride at the same temperature and the resulting mixture is stirred for 1 to 24 h, preferably 1 to 8 h. After the reaction mixture is subjected to a usual work-up, the compound (VII) can be obtained (see J. Chem. Soc. Parkin. Trans.1, 1987, 1986).

(Step 2)

To a solution of the compound (VII) in a solvent such as tetrahydrofuran, diethyl ether, and ethylene glycol dimethyl ether is added Grignard reagent ($R^1$MgHal: Hal is a halogen) at −20° C. to 0° C., preferably −15° C. to −10° C. and the resulting mixture is stirred for 1 to 15 h, preferably 1 to 8 h at −20° C. to 30° C., preferably 0° C. to 25° C. After the reaction mixture is subjected to a usual work-up, the compound (VIII) can be obtained (see Synthesis, 996, 1988).

(Step 3)

The present step includes ozone-oxidation of the double bond. A solution of the compound (VIII) in a solvent such as dichloromethane, ethyl acetate, and methanol is treated with ozone at −78° C. to 0° C., preferably −78° C. to −60° C. Without isolating the ozonide, the mixture is treated with a reducing agent such as dimethyl sulfide, triphenylphosphine, triethoxyphosphine, and zinc-acetic acid or hydrogen to give the aldehyde derivative (IX).

(Step 4)

To a solution of the compound (IX) in a solvent such as dioxane, tetrahydrofuran, and diethyl ether are added the compound (X) and an acid such as hydrochloric acid, sulfuric acid, and acetic acid. The resulting mixture is stirred for 0.5 to 3 h at 50° C. to 100° C. to give the pyrrole derivative (XI) which is protected by phthalimide at N-position (Chem. Ber., 102, 3268, 1969).

(Step 5)

The present step is the one for deprotecting the phthalimide group of the compound (XI). This step may be carried out in accordance with a usual deprotecting method as described in Protective Groups in Organic Synthesis, Theodora W Green (John Wiley & Sons). For example, to a solution of the compound (XI) in an alcohol solvent such as ethanol is added hydrazine and the resulting mixture is stirred for 0.5 to 3 h at 50° C. to 100° C. to give the amino derivative (XII).

(Step 6)

The present step is the one for alkylating the amino group. The compound (XII) and the compound (XIII) are reacted for 10 to 60 min at 100° C. to 150° C. to give the compound (XIV) (see J. Heterocyclic Chem., 31, 409, 1994).

(Step 7)

The present step is the one for constructing pyrrolo[1,2-b]pyridazine ring. The compound (XIV) is dissolved in a solvent such as Dowtherm-A and SAS-296 and the mixture is stirred for 1 to 8 h at 150° C. to 250° C. to give the pyrrolo[1,2-b]pyridazine derivative (XV) (see J. Heterocyclic Chem., 31, 409, 1994). The hydroxy group at 4-position is converted into halogen by the usual method, then the halogen is may be converted into a thiol group or the like.

(Step 8)

To a solution of the compound (XV) in a solution such as tetrahydrofuran and dimethylformamide are added a base such as potassium carbonate and sodium hydride and $R^{26}$-Hal (Hal is halogen) and the resulting mixture is stirred for 1 to 15 h at 0° C. to 100° C., preferably 20 to 40° C. to give the compound (XVI).

(Step 9)

The present step is the one for introducing a substituent to 5-position. The compound (XVI) is dissolved in a solvent such as 1,2-dichloroethane, tetrahydrofuran, and Hal-C(=X)—C(=X)-Hal (for example, oxalyl chloride) and a base such as N-methylmorpholine, triethylamine are added to the solution, and the mixture is stirred for 1 to 10 h, preferably 3 to 6 h at 30° C. to 70° C., preferably 40° C. to 60° C. The reaction mixture is poured into cold aqueous ammonia, and the resulting mixture is stirred for 5 to 30 minutes, preferably 10 to 20 minutes. After the reaction mixture is subjected to an ordinary work-up, the compound (XVII) can be obtained.

(Method B)

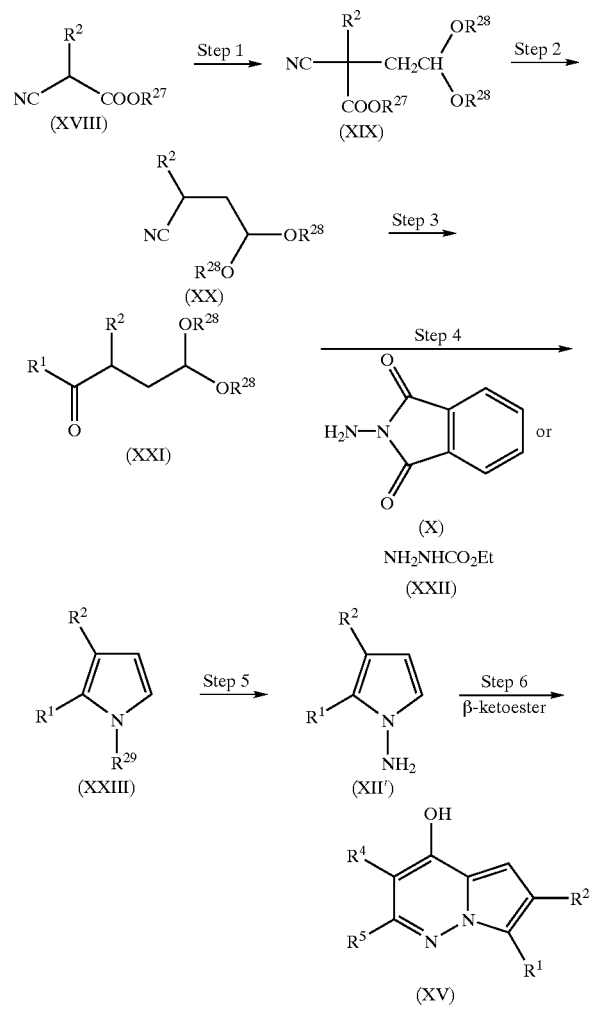

wherein $R^1$, $R^2$, $R^4$, and $R^5$ are as defined above, $R^{27}$ is C1 to C3 alkyl, $R^{28}$ is lower alkyl $R^{28}$ with the adjacent oxygen may form a 1,3-dioxolane ring, and $R^{29}$ is a phthalimido or NHCO$_2$Et.

(Step 1)

To a solution of the compound (XVIII) in a solvent such as dimethylformamide are added a halogenated alkyl derivative such as bromoacetaldehyde ethyleneacetal and a base such as potassium carbonate, potassium t-butoxide, and sodium hydride and the resulting mixture is stirred for 3 to 80 h, preferably 5 to 7 h at room temperature to 180° C., preferably 20 to 150° C. to give the compound (XIX).

(Step 2)

To a solution of the compound (XIX) in a solvent such as dimethylsulfoxide is added a reagent such as potassium acetate and sodium acetate and the resulting mixture is stirred for 1 to 20 h, preferably 3 to 15 h at 20° C. to 200° C., preferably 100° C. to 180° C. to give the compound (XX).

(Step 3)

To a solution of Grignard reagent (R$^1$MgHal, Hal is halogen) or R$^1$Li in a solvent such as ether, tetrahydrofuran, and dimethoxyethane is added a solution of the compound (XX) in ether, tetrahydrofuran, and dimethoxyethane and the resulting mixture is stirred for 1 to 48 h, preferably 2 to 24 h at 0° C. to 70° C., preferably 20 to 60° C. to give the compound (XXI).

(Step 4)

To a solution of the compound (XXI) in a solvent such as ethanol, methanol, dioxane, and tetrahydrofuran are added N-aminophthalimide (compound (X)) or ethyl carbazate (compound (XXII)) and an acid such as trifluoroacetic acid, hydrochloric acid, and sulfuric acid and the resulting mixture is stirred for 5 min to 2 h, preferably 10 min to 1 h at 20° C. to 120° C., preferably 50 to 100° C. to give the compound (XXIII).

(Step 5)

The present step may be carried out in accordance with the same procedure as that of the method A—step 5.

To a solution of the compound (XII') in a solvent such as chloroform, dichloroethane, tetrahydrofuran, and toluene are added β-ketoester such as acetoacetic acid methylester and an acid catalyst such as p-toluenesulfonic acid, methanesulfonic acid, hydrochloric acid, trifluoroacetic acid and the resulting mixture is stirred for 1 to 20 h, preferably 3 to 15 h to give the compound (XV). The generated water in situ is dehydrated by a Dean-Stark apparatus with molecular sieve 4A or the like.

(Method C)

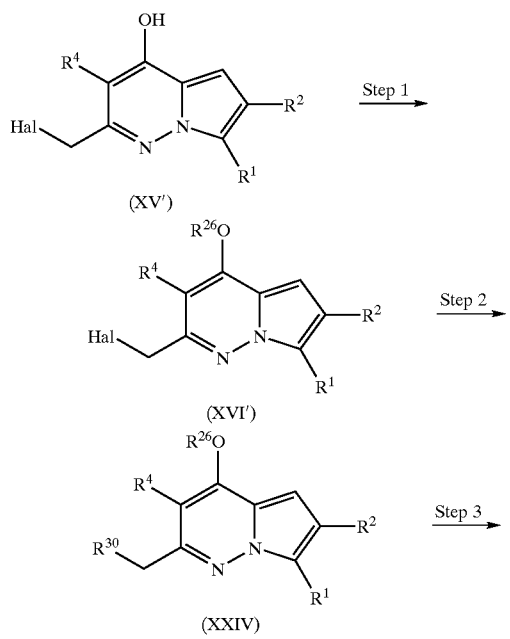

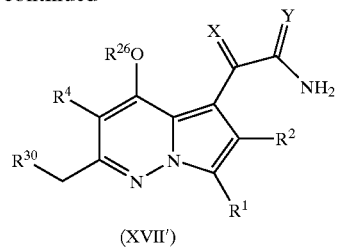

wherein R$^1$, R$^2$, R$^4$, R$^{26}$, X, and Y are as defined above, Hal is halogen, R$^{30}$ is —OR$^{31}$, —SR$^{31}$, —NHR$^{31}$, —N(R$^{31}$)$_2$, —CN, —N$_3$, or the like wherein R$^{31}$ is independently alkyl, aryl, or the like.

(Step 1)

The compound (XVI') is obtained in a manner similar to that described in the method A—step 8.

(Step 2)

The compound (XVI') is dissolved in a solvent such as dimethylformamide, acetonitrile, acetone, dimethylsulfoxide, methanol, ethanol, isopropanol and to the solution is added a base as a dehydrohalogenating agent such as potassium carbonate, sodium carbonate, sodium hydrogencarbonate, sodium acetate, sodium hydroxide, potassium hydroxide, sodium hydride, potassium t-butoxide. Then to the mixture is added a reagent such as R$^{31}$OH, R$^{31}$SH, R$^{31}$NH$_2$, (R$^{31}$)$_2$NH and the resulting mixture is stirred for 1 to 48 h preferably 1 to 24 h at −20° C. to 100° C., preferably 0° C. to 80° C. to give the compound (XXIV).

(Step 3)

The compound (XVII') is obtained in a manner similar to that described in the method A—step 9.

(Method D)

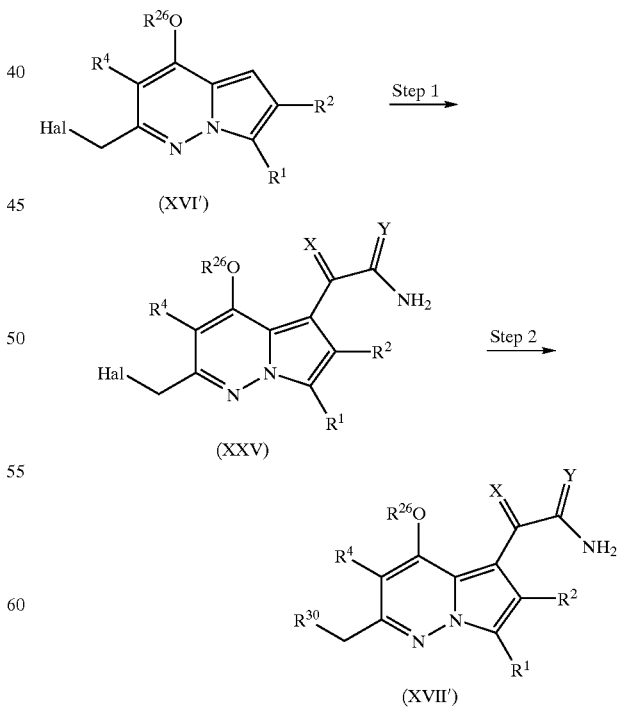

wherein R$^1$, R$^2$, R$^4$, R$^{26}$, R$^{30}$, X, Y, and Hal are as defined above.

(Step 1)

The compound (XXV) is obtained in a manner similar to that described in the method A—step 9.

The compound (XVII') is obtained in a manner similar to that described in the method C—step 2.

Where a compound of the present invention has an acidic or basic functional group, a variety of salts each having higher water solubility and more physiologically suitable properties than those of the original compound can be formed. An example of typical pharmaceutically acceptable salts includes salts with alkali metal and alkaline earth metal such as lithium, sodium, potassium, magnesium, aluminum and the like, but it is to be noted that such pharmaceutically acceptable salts are not limited thereto. A salt is easily manufactured from a free acid by either treating an acid in a solution with a base, or allowing an acid to be in contact with an ion exchange resin. Addition salts of the compounds according to the present invention with relatively non-toxic inorganic bases and organic bases, for example, amine cation, ammonium, and quaternary ammonium derived from nitrogenous bases having a basicity sufficient for forming a salt of the compounds of the present invention are included in the definition of "pharmaceutically acceptable salts". (e.g., S. M. Berge et al., "Pharmaceutical Salts," J. Phar. Sci., 66, 1–19 (1977)) Furthermore, basic groups of a compound according to the present invention are reacted with a suitable organic or inorganic acid to form salts such as acetates, benzenesulfonates, benzoates, bicarbonates, bisulfates, bitartarate, borates, bromides, camcyrates, carbonates, chlorides, clubranates, citrates, edetates, edicirates, estrates, ethylates, fluorides, fumarates, gluseptates, gluconates, glutamates, glycolialsanyrates, hexyliresorcinates, hydroxynaphthoates, iodides, isothionates, lactates, lactobionates, laurates, malates, malseates, manderates, mesylates, methylbromides, methylnitrates, methylsulfates, mucates, napcylates, nitrates, oleates, oxarates, palmitates, pantothenates, phosphates, polygalacturonates, salicirates, stearates, subacetates, sucinates, tanates, tartrates, tosylates, trifluoroacetates, trifluoromethanesulfonates, valerates and the like. In case of forming a hydrate, a questioned compound may be coordinated with a suitable number of water molecules.

In the case where a compound of the present invention has one or more of chiral center(s), it may exist as an optically active member. Likewise, in the case where a compound contains alkenyl or alkenylene, there is a possibility of cis- and trans-isomers. Mixtures of R- and S-isomers as well as of cis- and trans-isomers, and mixtures of R- and S-isomers containing racemic mixture are included in the scope of the present invention. Asymmetric carbon atom may exist also in a substituent such as alkyl group. All such isomers are included in the present invention together with these mixtures. In the case where a specified streoisomer is desired, either it is manufactured by applying a manner which has been well known by those skilled in the art wherein a starting material having an asymmetrical center which has been previously separated is subjected to stereospecific reaction to the starting material, or it is manufactured by preparing a mixture of stereoisomers, and thereafter separating the mixture in accordance with a well-known manner.

Prodrug is a derivative of the compound having a group which can be decomposed chemically or metabolically, and such prodrug is a compound according to the present invention which becomes pharmaceutically active by means of solvolysis or by placing the compound in vivo under a physiological condition. Although a derivative of the compounds according to the present invention exhibits activity in both forms of acid derivative and basic derivative, acid derivative is more advantageous in solubility, tissue affinity, and release control in mammal organism (Bungard, H., Design of Prodrugs, pp. 7–9, 21–24, Elsevier, Amsterdam, 1985). Ester prodrugs are well known (see, Silverman, Richard B, The Organic Chemistry of Drug Design and Drug Action, Chapter 8, New York, N.Y. Academic Press, ISBN 0-12-643730-0) and are a preferred prodrug form for the compounds of this invention and also for prodrugs used in the method of treating Inflammatory Disease as taught herein. For instance, prodrugs each containing an acid derivative such as an ester which is prepared by reacting a basal acid compound with a suitable alcohol, or an amide which is prepared by reacting a basal acid compound with a suitable amine are well known by those skilled in the art. Simple aliphatic or aromatic esters derived from acid groups contained in the compounds according to the present invention are preferable prodrugs. Particularly preferred esters as prodrugs are methyl ester, ethyl ester, n-propyl ester, iso-propyl ester, n-butyl ester, isobutyl ester, tert-butyl ester, morpholinoethyl ester, and N,N-diethylglycolamido ester.

Methyl ester prodrugs may be prepared by reaction of the sodium salt of a compound of Formula (I) (in a solvent such as dimethylformamide) with iodo methane (available from Aldrich Chemical Co., Milwaukee, Wis. USA; Item No. 28,956-6).

Ethyl ester prodrugs may be prepared by reaction of the sodium salt of a compound of Formula (I) (in a solvent such as dimethylformamide) with iodo ethane (available from Aldrich Chemical Co., Milwaukee, Wis. USA; Item No. I-778-0).

N,N-diethylglycolamido ester prodrugs may be prepared by reaction of the sodium salt of a compound of Formula (I) (in a medium such as dimethylformamide) with 2-chloro-N,N-diethylacetamide (available from Aldrich Chemical Co., Milwaukee, Wis. USA; Item No. 25,099-6).

Morpholinylethyl ester prodrugs may be prepared by reaction of the sodium salt of a compound of Formula (I) (in a medium such as dimethylformamide) with 4-(2-chloroethyl)morpholine hydrochloride (available from Aldrich Chemical Co., Milwaukee, Wis. USA, Item No. C4,220-3).

Double ester such as (acyloxy)alkyl ester or ((alkyloxycarbonyl)oxy)alkyl ester type prodrugs may be optionally manufactured.

The term "inhibit" means that release of fatty acid started by sPLA$_2$ decreases significantly by the compounds of the present invention from viewpoint of prevention and treatment of disease. The term "pharmaceutically acceptable" means that carriers, diluents, or additives are compatible with other ingredients in a formulation and are not harmful for recipients.

The compounds of the present invention exhibit sPLA$_2$ inhibiting activity as per the description of the experimental examples which will be described hereinafter. Accordingly, when a curatively effective amount of the compounds represented by the formulae (I), (II), (III), and (IV), the prodrug derivatives thereof, or their pharmaceutically acceptable salts, or their solvates is administered to any of mammals (including human being), it functions effectively as a curative medicine for diseases of septic shock, adult respiratory distress syndrome, pancreatitis, injury, bronchial asthma, allergic rhinitis, chronic rheumatism, arterial sclerosis, cerebral hemorrhage, cerebral infarction, inflammatory colitis, mange, cardiac failure, cardiac infarction.

The compounds of the present invention may be administered to a patient through a variety of routes including oral, aerosol, rectal, percutaneous, subcutaneous, intravenous, intramuscular, and nasal routes. A formulation according to the present invention may be manufactured by combining (for example, admixing) a curatively effective amount of a compound of the present invention with a pharmaceutically acceptable carrier or diluent. The formulation of the present invention may be manufactured with the use of well-known and easily available ingredients in accordance with a known method.

In case of manufacturing a composition according to the present invention, either active ingredients are admixed with a carrier, or they are diluted with a carrier, or they are contained in a carrier in the form of capsule, sacheier, paper, or another container. In case of functioning a carrier as a diluent, the carrier is a solid, semi-solid, or liquid material which functions as a medium. Accordingly, a formulation according to the present invention may be produced in the form of tablet, pill, powder medicine, intraoral medicine, elixir agent, suspending agent, emulsifier, dissolving agent, syrup agent, aerosol agent (solid in liquid medium), and ointment. Such a formulation may contain up to 10% of an active compound. It is preferred to prepare a compound according to the present invention prior to administration.

Any suitable carrier which has been well known by those skilled in the art may be used for the formulation. In such formulation, a carrier is in the form of solid, liquid, or a mixture of solid and liquid. For instance, a compound of the present invention is dissolved into 4% dextrose/0.5% sodium citrate aqueous solution so as to be 2 mg/ml concentration for intravenous injection. Solid formulation includes powder, tablet, and capsule. Solid carrier consists of one or more of material(s) for serving also as fragrant, lubricant, dissolving agent, suspension, binder, tablet disintegrator, capsule. A tablet for oral administration contains a suitable excipient such as calcium carbonate, sodium carbonate, lactose, calcium phosphate and the like together with a disintegrator such as corn starch, alginic acid and the like and/or a binder such as gelatin, acacia and the like, and a lubricant such as magnesium stearate, stearic acid, talc and the like.

In a powder medicine, a carrier is a finely pulverized solid which is blended with finely pulverized active ingredients. In a tablet, active ingredients are admixed with a carrier having required binding power in a suitable ratio, and it is solidified in a desired shape and size. Powder medicine and tablet contain about 1 to about 99% by weight of the active ingredients being novel compounds according to the present invention. An example of suitable solid carriers includes magnesium carbonate, magnesium stearate, talc, sugar, lactose, pectin, dextrin, starch, gelatin, tragacanth gum, methyl cellulose, sodium carboxymethylcellulose, low-melting wax, and cocoa butter.

An axenic liquid formulation contains suspending agent, emulsifier, syrup agent, and elixir agent. Active ingredients may be dissolved or suspended into a pharmaceutically acceptable carrier such as sterile water, a sterile organic solvent, a mixture thereof and the like. Active ingredients may be dissolved frequently into a suitable organic solvent such as propylene glycol aqueous solution. When finely pulverized active ingredients are dispersed into aqueous starch, sodium carboxylmethylcellulose solution, or suitable oil, the other compositions can be prepared.

A lyophilized preparation may be prepared by dissolving active ingredients in a solution such as water, if necessary, with a solubilizer such as citric acid, edetic acid, polyphosphoric acid and their salts and a stabilizer such as mannitol, xylitol, sorbitol, glucose, fructose, lactose and maltose and lyophilizing it.

The method of the invention for inhibiting $sPLA_2$ mediated release of fatty acids comprises contacting mammalian $sPLA_2$ with a therapeutically effective amount of a pyrrolo [1,2-b]pyridazine $sPLA_2$ inhibitors (and formulation containing such inhibitors) as taught, supra.

Preferably compounds of the invention (per Formula (I) or (II) or (III) or (IV) or pharmaceutical formulations containing these compounds) are in unit dosage form for administration to a mammal. The unit dosage form can be a capsule or tablet itself, or the appropriate number of any of these. The quantity of Active ingredient in a unit dose of composition may be varied or adjusted from about 0.1 to about 1 000 milligrams or more according to the particular treatment involved. It may be appreciated that it may be necessary to make routine variations to the dosage depending on the age and condition of the patient. The dosage will also depend on the route of administration.

The improved method of treatment for sepsis using the pyrrolo[1,2-b]pyridazine $sPLA_2$ inhibitors (and formulation containing such inhibitors) may be practiced as follows:

The inhibitors of this invention are given by injection, either subcutaneously or into muscle tissue or by injection into a vein. Intravenous injection is the preferred mode of delivery to the mammal being treated and offers the advantage of a quick effect and rapid access into the circulation system, particularly in emergency situations.

It may be appreciated that it may be necessary to make routine variations to the dosage depending on the age and condition of the patient. The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a non-toxic Compound (I) dosage level of from about 0.01 mg/kg to about 50 mg/kg of body weight of an Active ingredient of this invention.

This invention is a method of treating or preventing Inflammatory diseased, (e.g., sepsis, rheumatoid arthritis, osteoarthritis, asthma) by administering to a mammal in need thereof a therapeutically effective amount inhibitor. The administration to a septic patient may be either continuous or intermittent.

The decision to begin the therapy for sepsis will be based upon the appearance of the clinical manifestations of sepsis or laboratory tests which show initiation of the sepsis cascade (inclusive of renal complications or coagulation abnormalities or multiple organ failure). Typical clinical manifestations are fever, chills, tachycardia, tachypnea, altered mental state, hypothermia, hyperthermia, accelerated or repressed breathing or heart rates, increased or decreased white blood cell count, and hypotension. These and other symptoms are well known in the art as set out in standard references such as, Harrison's Principles of Internal Medicine (ISBN 0-07-032370-4) 1994, pages 511–515.

The decision to determine the length of therapy may be supported by standard clinical laboratory results from commercially available assays or instrumentation supporting the eradication of the symptoms defining sepsis. The method of the invention may be practiced by continuously or intermittently administering a therapeutically effective dose of the inhibitor. The administration can be conducted for up to a total of about 60 days with a preferred course of therapy lasting for up to 10 days.

The decision to end therapy by the method of the invention may be supported by standard clinical laboratory results from commercially available assays or instrumentation or the disappearance of clinical symptoms characteristic of sepsis. The therapy may be restarted upon the return of sepsis. Pediatric forms of sepsis are also successfully treated by the methods, compounds, and formulations of this invention.

When the compound of the present invention is a crystallized, it may show various crystal forms and crystal habits.

The present invention will be described in more detail in conjunction with examples and test examples hereinafter, but it is to be noted that the present invention is not limited thereto.

In the examples, the following abbreviations are used.

Me: methyl
Et: ethyl
Pr: propyl
Ph: phenyl
NPhth: phthaloylimide
(d) of the melting point: decomposition temperature
DBU: 1,8-diazabicyclo[5.4.0]-7-undecene

EXAMPLE

Example 1

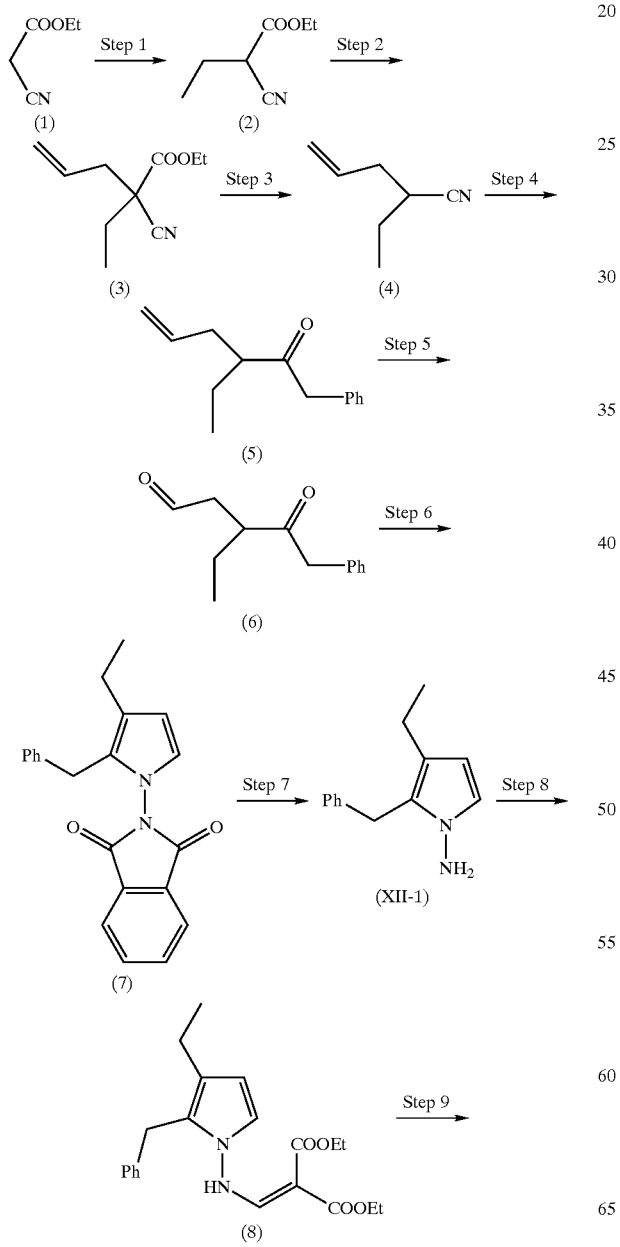

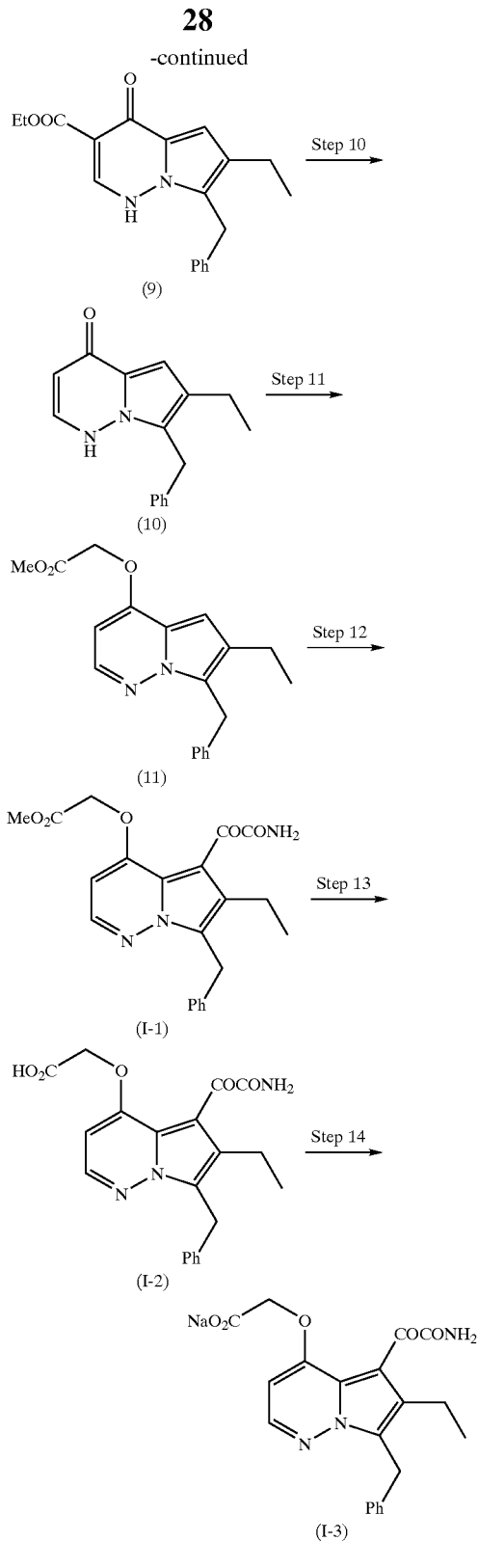

Example 1—Step 1

The compound (1) (18.2 g, 0.160 mol) and 90% acetaldehyde (9.43 g, 0.190 mol) were dissolved in 20 ml of acetic acid and to the mixture were added 10% Pd—C catalyst (300 mg) and acetic acid solution (10 ml) of piperidine (0.63 ml, 6.37 mmol). The resulting mixture was stirred for 3 h at room temperature under hydrogen at 1 to 2 atm. The reaction mixture was filtered for removing the catalyst, diluted with toluene, and washed with water. The mixture was distilled under reduced pressure to give the compound (2) (20.00g, 88%, boiling point 92 to 94° C. (13 mmHg)) as colorless liquid (see OS, III, 385, 1955. J. Am. Chem. Soc., 66, 886 (1944)). OS, III, 385, 1955. J. Am. Chem. Soc., 66, 886 (1944)).

Example 1—Step 2

To a solution of the compound (2) (19.2 g, 0.140 mol) in acetone (200 ml) were added allyl bromide (60.2 ml, 0.700 mol) and potassium carbonate (36.0 g, 0.260 mol) and the resulting mixture was heated under reflux for 5 h. The reaction mixture was filtered and the filtrate was distilled under reduced pressure to give the compound (3) (22.0 g, 89%, boiling point 107 to 109° C. (14 mmHg)) as colorless liquid (see Compt. Rend., 253. 1808 (1961)).

Example 1—Step 3

The compound (3) (16.8 g, 92.5 mmol) and potassium acetate (10.0 g, 102 mmol) were dissolved in 85 ml of dimethylsulfoxide and the resulting mixture was stirred for 5 h at 150° C. To the reaction mixture was added water, the mixture was extracted with ether, and the organic layer was washed with water, dried over magnesium sulfate, and distilled at atmospheric to give the compound (4) (8.00 g, 79%, boiling point 168 to 172° C.) (see Compt. Rend., 253, 1808 (1961) and Indian J. Chem., 25, 1249 (1986))

Also, the compound (4) may be synthesized in accordance with the method described in J. Chem. Soc. Perkin Trans. 1, 1837, 1986. described in J. Chem. Soc. Perkin Trans. 1, 1837, 1986.

Example 1—Step 4

To a solution of magnesium (3.03 g, 0.125 mol) and 1,2-dibromoethane (0.49 ml, 5.67 mmol) in 70 ml of ether was added a solution of benzyl bromide (21.3 g, 0.125 mmol) in 30 ml of ether under ice-cooling. The mixture was allowed to warm to the room temperature and stirred until magnesium was dissolved. A solution of the compound (4) (12.4 g, 0.113 mol) in 30 ml of ether was added dropwise to the resulting mixture and the reaction mixture was heated under reflux for 2 h. To the reaction mixture was added water under ice-cooling and the mixture was acidified with 50 ml of 2.5 N sulfuric acid. The resulting mixture was stirred for 100 min on a water bath (90° C.) while removing ether. The reaction mixture was extracted with ether and the organic layer was washed with brine, dried over magnesium sulfate, and concentrated in vacuo. The residue was chromatographed on silica gel using ethyl acetate-hexane (1:20) and appropriate fractions were distilled under reduced pressure to give the compound (5) (17.6 g, 77%, boiling point 90 to 91° C. (0.4 mmHg)) as colorless liquid (see Synthesis, 996, 1988).

$^1$H-NHR (CDCl$_3$): 0.81 (3H, t, J=7.4 Hz), 1.41–1.78 (2H, m), 2.09–2.41 (2H, 2.56–2.70 (1H, m), 3.71 (2H, s), 4.96–5.06 (2H, m), 5.56–5.77 (1H, m), 7.15–7.37 (5, m).

Example 1—Step 5

The compound (5) (13.4 g, 66.1 mmol) was dissolved in 150 ml of dichloromethane, ozone gas was introduced to the mixture at −78° C. until the starting material disappeared, and the excess amount of ozone gas was replaced by argon gas. To the resulting mixture was added a solution of triphenylphosphine (17.7 g, 67.4 mmol) in 50 ml of dichloromethane and the mixture was stirred for 30 min at room temperature. After the solvent was removed, precipitated crystals were filtered with washing with a mixed solvent of ethyl acetate and hexane and the filtrate was concentrated in vacuo. The resulting residue was subjected to silica gel column chromatography and using ethyl acetate and hexane (1:4) as an eluent to give the compound (6) (11.2 g, 83%) as colorless liquid.

$^1$H-NHR (CDCl$_3$): 0.87 (3H, t, J=7.5 Hz), 1.41–1.75 (2H, m), 2.50 (1H, dd, J=18.3, 3.9 Hz), 2.96 (1H, dd, J=18.3, 9.6 Hz), 3.06–3.15 (1H, m), 3.84 (1H, d, J=16.2 Hz), 3.91 (1H, d, J=16.2 Hz), 7.20–7.36 (5H, m), 9.70 (1H, s).

Example 1—Step 6

The compound (6) (11.2 g, 54.6 mmol) and N-aminophthalimide (8.85 g, 54.6 mmol) were suspended in 250 ml of dioxane, 5N hydrochloric acid (6 ml, 30.0 mmol) was added to the suspension, and the mixture was stirred for 30 min at 100° C. The half of the reaction mixture was concentrated, diluted with ether, washed with brine, dried over magnesium sulfate, and concentrated in vacuo. The residue was subjected to silica gel column chromatography and the fractions eluting with chloroform/hexane=2:1 were collected and recrystallized from hexane to give the compound (7) (14.8 g, 82%, melting point 153 to 154° C.) as colorless crystals (see Chem. Ber., 102, 3268(1969)).

Elemental Analysis C$_{21}$H$_{18}$N$_2$O$_2$; Calcd.: C, 76.34; H, 5.49; N, 8.48. Found.: C, 76.11; H, 5.47; N, 8.69. $^1$H-NHR (CDCl$_3$): 1.22 (3H, t, J=7.5 Hz), 2.52 (2H, q, J=7.5 Hz), 3.81 (2H, s), 6.24 (1H, d, J=3.3 Hz), 6.60 (1H, d, J=3.3 Hz), 6.91–7.03 (5H, m), 7.74–7.83 (4H, m).

Example 1—Step 7

The compound (7) (14.9 g, 45.2 mmol) was suspended in 300 ml of ethanol, hydrazine monohydrate (5.5 ml, 113 mmol) was added to the suspension, and the mixture was stirred for 30 min at 100° C. The precipitated crystals were filtered off and the filtrate was concentrated in vacuo. The residue was chromatographed on silica gel using chloroform to give the compound (XII-1) (9.00 g, 99%) as colorless oil.

$^1$H-NHR (CDCl$_3$): 1.16 (3H, t, J=7.5 Hz), 2.46 (2H, q, J=7.5 Hz), 3.99 (2H, s), 4.23 (1H, br s), 5.94 (1H, d, J=2.7 Hz), 6.64 (1H, d, J=2.7 Hz), 7.07–7.30 (5H, m).

Example 1—Step 8

Diethyl ethoxymethylenemalonate (7.57 g, 35.0 mmol) was added to the compound (XII-1) (6.38 g, 31.9 mmol) and the mixture was heated for 40 min at 125° C. with removing ethanol generated in situ. To the reaction mixture was added hexane and the precipitated crystals were filtered to give the compound (8) (7.67 g, 65%, melting point 60 to 61° C.) as colorless crystals. The filtrate was purified by chromatography on silica gel (elution with ethyl acetate/hexane=1/6) to give the compound (8) (3.54 g, 30%) as colorless crystals (see J. Heterocyclic Chem., 31, 409, 1994).

Elemental Analysis C$_{21}$H$_{26}$N$_2$O$_4$, Calcd: C, 68.09; H, 7.07; N, 7.56. Found: C, 67.69; H, 7.06; N, 7.68. $^1$H-NHR (CDCl$_3$): 1.20 (3H, t, J=7.2 Hz), 1.21 (3H, t, J=7.2 Hz), 1.33 (t, J=6.9 Hz), 2.51 (2H, q, J=6.9 Hz), 3.88 (2H, s), 4.08 (2H, q, J=7.2 Hz), 4.24 (2H, q, J=7.2 Hz), 6.07 (1H, d, J=3.3 Hz), 6.66 (1H, d, J=3.3 Hz), 7.00–7.28 (5H, m), 7.67 (1H, d, J=11.1 Hz), 10.32 (1H, d, J=11.1 Hz).

Example 1—Step 9

The compound (8) (11.9 g, 32.1 mmol) was dissolved in SAS-296 (phenylxylylethane) and the mixture was heated for 5 h at 200 to 210° C. under argon atmosphere. The reaction mixture was chromatographed on silica gel using toluene/hexane (=1/2) to give the compound (9) (6.85 g, 66%) as yellow crystals. The crystals were recrystallized from hexane (melting point 75 to 76° C.).

Elemental Analysis $C_{19}H_{20}N_2O_3$, Calcd.: C, 70.35; H, 6.21; N, 8.64. found.: C, 70.22; H, 6.28; N, 8.88. $^1$H-NHR (CDCl$_3$): 1.24 (3H, t, J=7.5 Hz), 2.66 (2H, q, J=7.5 Hz), 4.37 (2H, s), 6.88 (1H, s), 7.12–7.25 (5H, m), 8.28 (1H, s), 12.18 (1H, s).

Example 1—Step 10

The compound (9) (3.02 g, 9.30 mmol) was dissolved in 10 ml of dimethylsulfoxide. Sodium chloride (598 mg, 10.2 mmol) and water (519 mg, 28.8 mmol) were added to the solution and the mixture was stirred for 4 h at 150° C. The solvent was removed and the residue was purified by chromatography on silica gel (elution with ethyl acetate/hexane= 1/4) to give the compound (10) (1.32 g, 63%) as colorless crystals. This crystals were recrystallized from ether and hexane (melting point 113 to 114° C.).

Elemental Analysis $C_{16}H_{16}N_2O$, Calcd.: C, 76.16; H, 6.39; N, 11.10. Found: C, 75.93; H, 6.45; N, 11.27. $^1$H-NHR (CDCl$_3$): 1.24 (3H, t, J=7.5 Hz), 2.68 (2H, q, J=7.5 Hz), 4.39 (2H, s), 5.58 (1H, d, J=5.4 Hz), 6.53 (1H, s), 7.12–7.25 (5H, m), 7.80 (1H, d, J=5.4 Hz).

Example 1—Step 11

The compound (10) (1.03 g, 4.10 mmol) was dissolved in 8 ml of tetrahydrofuran. Potassium carbonate (680 mg, 4.92 mmol) and a solution of methyl bromoacetate (753 mg, 4.92 mmol) in 2 ml of tetrahydrofuran were added to the solution and the mixture was heated for 3 h at 50° C. The reaction mixture was diluted with chloroform and filtered. The filtrate was washed with brine, dried over magnesium sulfate, and concentrated in vacuo. The residue was subjected to silica gel column chromatography (eluting with toluene/ethyl acetate=1:50) to give the compound (11) (850 mg, 64%) as colorless crystals. This crystals were recrystallized from ether and methanol (melting point 94 to 95° C.).

Elemental Analysis $C_{19}H_{20}N_2O_3$, Calcd.: C, 70.35; H, 6.21; N, 8.64. Found: C, 70.32; H, 6.29; N, 8.88. $^1$H-NHR (CDCl$_3$): 1.24(3H, t, J=7.5 Hz), 2.69 (2H, q, J=7.5 Hz), 3.82 (3H, s), 4.39 (2H, s), 4.78 (2H, s), 5.72 (1H, d, J=5.4 Hz), 6.63 (1H, s), 7.10–7.25 (5H, m), 7.84 (1H, d, J=5.4Hz).

Example 1—Step 12

To a solution of oxalyl chloride (752 mg, 5.92 mmol) in 7 ml of dichloromethane were added a solution of the compound (11) (384 mg, 1.18 mmol) in 3 ml of dichloromethane and N-methylmorpholine (240 mg, 2.37 mmol) at −15° C. and the mixture was stirred for 2 h at 0° C. After the mixture was added to an ice-cold aqueous ammonia stirred for 10 min at room temperature, the mixture was extracted with chloroform. The organic layer was washed with brine, dried over magnesium sulfate, and concentrated in vacuo. The residue was recrystallized from methanol to give the compound (I-1) (416 mg, 89%, melting point 210 to 212° C.) as pale yellow crystals.

Elemental Analysis $C_{21}H_{21}N_3O_5$, Calcd.: C, 63.79; H, 5.35; N, 10.63. Found: C, 63.59; H, 5.39; N, 10.91. $^1$H-NHR (CDCl$_3$): 1.16 (3H, t, J=7.5 Hz), 2.86 (2H, q, J=7.5 Hz), 3.80 (3H, s), 4.37 (2H, s), 4.76 (2H, s), 5.56 (1H, br. s), 6.06 (1H, d, J=5.4 Hz), 6.70 (1H, br s), 7.13–7.25 (5H, m), 8.02(1H, d, J=5.4Hz).

Example 1—Step 13

The compound (I-1) (248 mg, 0.627 mmol) was suspended in 3 ml of methanol, 1 ml of 1N sodium hydroxide was added to the suspension at room temperature, and the mixture was stirred for 1 h. The mixture was acidified with 1 N hydrochloric acid under ice-cooling and precipitated crystals were filtered to give the compound (I-2) (162 mg, 86%, decomposition point 252 to 255° C.) as pale yellow crystals.

Elemental Analysis $C_{20}H_{19}N_3O_5$, Calcd.: C, 62.99; H, 5.02; N, 11.02. Found: C, 62.80; H, 5.06; N, 11.21. $^1$H-NHR (DMSO): 1.04 (3H, t, J=7.2 Hz), 2.79 (2H, q, J=7.2 Hz), 4.35 (2H, s), 4.88 (2H, s), 6.48 (1H, d, J=5.4 Hz), 7.12–7.29 (5H, m), 7.40 (1H, br s), 7.79 (1H, br. s), 8.23 (1H, d, J=5.4 Hz), 13.29 (1H, br s).

Example 1—Step 14

The compound (I-2) (51.4 mg, 0.134 mmol) was suspended in 2 ml of $H_2O$ and 0.1 N sodium hydroxide (1.34 ml, 0.134 mmol) was added to the mixture under ice-cooling. The mixture was filtered and lyophilized to give the compound (I-3) (50.1 mg, decomposition point 280° C.) as yellow powder.

Example 2

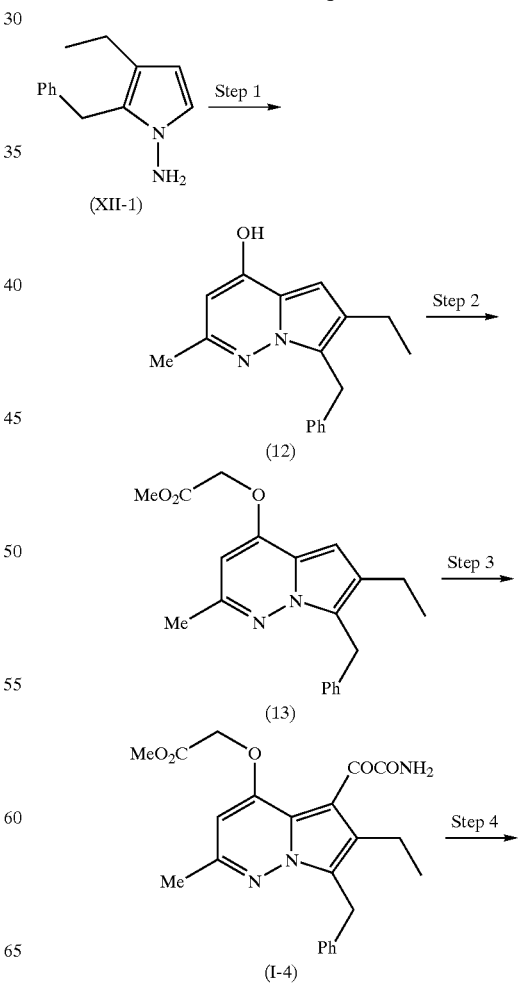

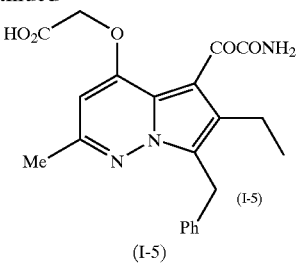

(I-5)

(Step 1)

A mixture of the compound (XII-1) (601 mg, 3 mmol), methyl acetoacetate (348 mg, 3 mmol), p-toluenesulfonic acid monohydrate (29 mg, 0.15 mmol) and 20 ml of chloroform was heated under reflux for 15 h with an oil-bath. Generated water was dehydrated by a Dean-Stark apparatus with molecular sieve 4A. To the reaction mixture were added water and 25 mg of sodium bicarbonate. The mixture was extracted with chloroform, dried over magnesium sulfate, and subjected to silica gel column chromatography (16 g of silica gel, eluting with 2.5% acetonitrile-chloroform) to give the compound (12) (800 mg, 100%) as brown oil. $^1$H-NMR (CDCl$_3$): 1.21(3H, t, J=7.4 Hz), 2.65 (2H, q, J=7.4 Hz), 4.36(2H, s), 5.79 (1H, s), 6.43(1H, s), 7.20(5H, m).

(Step 2)

A mixture of the compound (12) (799 mg, 3 mmol), methyl bromoacetate (0.37 ml, 3.9 mmol), potassium carbonate (539 mg, 3.9 mmol), and 10 ml of dimethylformamide was stirred for 1 h at room temperature and to the reaction mixture was added water. The mixture was extracted with toluene, washed with water, dried over magnesium sulfate, subjected to silica gel column chromatography (20 g of silica gel, eluting with toluene) to give 797 mg of the eluate. The eluate was recrystallized from acetone and isopropyl ether to give the compound (13) (739 mg, 72.5%, melting point 120 to 121° C.) as white crystals. $^1$H-NMR (CDCl$_3$): 1.22(3H, t, J=7.4 Hz), 2.38(3H, s), 2.65(2H, q, J=7.4 Hz), 3.83 (3H, s), 4.35(2H, s), 4.77(2H, s), 5.60(1H, s), 6.54(1H, s), 7.20(5H, s).

(Step 3)

The compound (13) (676 mg, 2 mmol) and N-methylmorpholine (0.44 ml, 4 mmol) were dissolved in 10 ml of dichloromethane. The mixture was added to a solution of oxaryl chloride (0.87 ml, 10 mmol) in 17 ml of dichloromethane, cooled to −10° C. in an ice-methanol bath, and the resulting mixture was stirred for 30 min at the same temperature. The reaction mixture was added to 10 ml of conc. aqueous ammonia and the insoluble material were filtered off. The filtrate was extracted with chloroform, washed with water, dried over magnesium sulfate, and subjected to silica gel column chromatography (30 g of silica gel, eluting with 50% of acetonitrile-chloroform). The eluate was recrystallized from acetone and ethyl acetate to give the compound (I-4) (774 mg, 94.5%, melting point 225 to 226° C.) as pale yellow crystals. $^1$H-NMR (d$_6$-DMSO): 1.02(3H, t, J=7.2 Hz), 2.41(3H, s), 2.76(2H, q, J=7.2 Hz), 3.72(2H, s), 4.32(2H, s), 4.95(2H, s), 6.50(1H, s), 7.15–7.30 (5H, m), 7.36(1H, br.s), 7.75(1H, br.s).

(Step 4)

The compound (I-5) was synthesized in a manner similar to that described in Example 1—Step 13. $^1$H-NMR (d$_6$-DMSO): 1.02(3H, t, J=7.5 Hz), 2.40(2H, s), 2.76(2H, q, J=7.5 Hz), 4.32(2H, s), 4.84(2H, s), 6.44(1H, s), 7.16–7.28 (5H, m), 7.36(1H, br.s), 7.75(1H, br.s).

Example 3

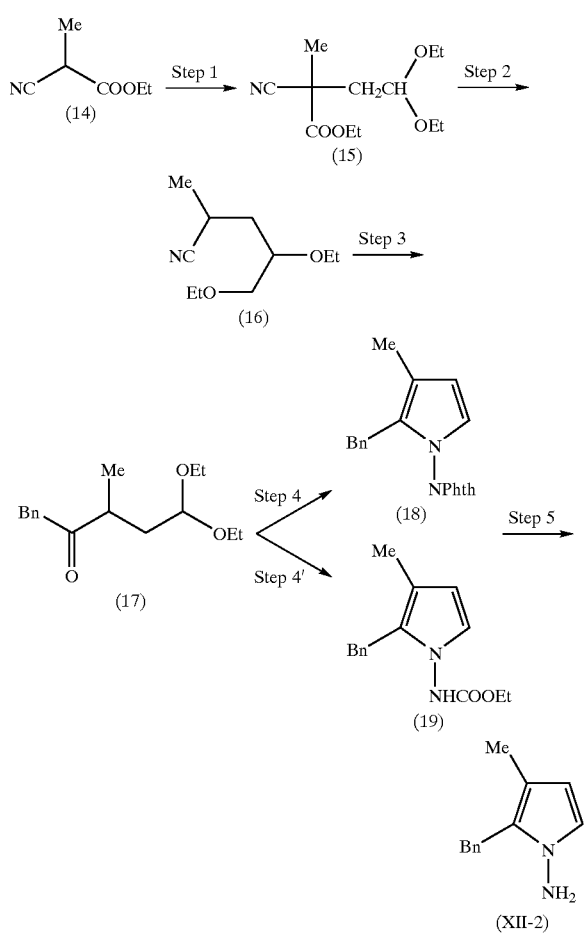

(Step 1)

A mixture of the compound (14) (25.8 g, 0.203 mol), bromoacetaldehyde diethylacetal (48.0 g, 0.244 mol), potassium carbonate (33.7 g, 0.244 mol), and 130 ml of dimethylformamide was heated for 24 h at 110° C. under nitrogen. Dimethylformamide was removed under reduced pressure and water was added to the residue. The mixture was extracted with toluene, washed with water, dried over magnesium sulfate, and toluene was removed under reduced pressure. The residue was distilled under reduced pressure to give the compound (15) (39.55 g, 80.1%, boiling point 99 to 102° C. (1 mmHg)) as colorless liquid. $^1$HNMR(CDCl$_3$): 1.38 (3H, t, J=7.0 Hz), 1.21 (3H, t, J=7.0 Hz), 1.62 (3H, s), 2.01(1H, m, J=14.2 Hz, J=4.2 Hz), 2.40 (1H, m, J=14.2 Hz, J=7.4 Hz), 3.49–3.75 (4H, m), 4.24(1H, q, J=7.0 Hz), 4.25 (1H, q, J=7.0 Hz), 4.75(1H, m, J=7.4 Hz, J=4.2 Hz).

(Step 2)

A mixture of the compound (15) (43.6 g, 0.179 mol), potassium acetate (19.3 g, 0.197 mol), and 87 ml of dimethylsulfoxide was heated for 14 h in the oil bath (160° C.) under nitrogen. After the mixture was cooled, water was added to the mixture, and the mixture was extracted with ether. The organic layer was washed with water, dried over magnesium sulfate, and concentrated in vacuo. The residue was distilled under reduced pressure to give the compound

(16) (29.48 g, 96.0%, boiling point 110–113° C. (23 mmHg)) as colorless liquid. $^1$H-NMR (CDCl$_3$) : 1.22(3H, t, J=7 Hz), 1.23(3H, t, J=7 Hz), 1.35(3H, d, J=7.6 Hz), 1.73–2.00(2H, m), 2.79(1H, m), 3.47–3.80(4H, m), 4.67(1H, m).

(Step 3)

To a Grignard reagent which was prepared by magnesium (1.53 g, 0.063 mol), 71 ml of ether, 1,2-dibromoethane (0.26 ml, 0.003 mol), and benzyl bromide (7.14 ml, 0.060 mol) was added a solution of the compound (16) (7.06 g, 0.05 mol) in 35 m of ether and the resulting mixture was stirred for 4 h at room temperature and heated for 5 h under reflux in an oil bath (60° C.). To the reaction mixture were added an aqueous ammonium chloride (5.35 g, 0.1 mol, 50 ml) under ice-cooling and 63 ml of 2N sulfuric acid and the mixture was stirred for 30 min. The reaction mixture was neutralized by adding sodium bicarbonate (3.36 g, 0.040 mol) and extracted with ether. The organic layer was dried over magnesium sulfate and concentrated in vacuo. The residue was dissolved in toluene and purified by chromatography on silica gel (90 g, eluting with 10% ethyl acetate-toluene) to give the compound (17) (9.13 g, 78%). $^1$H-NMR (CDCl$_3$): 1.11(3H, d, J=7 Hz), 1.58–2.24(2H, m), 2.90(1H, m), 3.77(2H, s), 3.78–3.90(4H, m), 4.87(1H, t, J=4.8 Hz), 7.14–7.37(5H, m).

(Step 4)

The compound (17) (35.9 g, 0.129 mol) and N-aminophthalimide (20.9 g, 0.129 mol) were suspended in 95% of ethanol (250 ml). To the suspension was added 1N-hydrochloric acid (13 ml, 0.013 mol) and the resulting mixture was heated for 30 min under reflux in an oil bath. After cooling, the precipitated crystals were filtered to give the compound (18) (35.96 g, 84.4%, melting point 151 to 152° C.) as pale yellow crystals. $^1$H-NMR (CDCl$_3$): 1.22 (3H, t, J=7.4 Hz), 2.52(2H, q, J=7.8 Hz), 3.81(2H, s), 6.24(1H, d, J=3 Hz), 6.60(1H, d, J=3 Hz), 6.92–7.03(5H, m), 7.79(4H, m).

(Step 4')

To a solution of the compound (17) (1.69 g, 8.6 mmol) and ethyl carbazate (0.90 g, 8.6 mmol) in 20 ml of dioxane was added 5N-hydrochloric acid (0.86 ml, 4.3 mmol) and the resulting mixture was heated for 30 min in an oil bath (100° C.). Dioxane was removed under reduced pressure and water was added to the residue. The mixture was alkalized with aq. sodium bicarbonate, extracted with toluene, dried over magnesium sulfate, subjected to silica gel column chromatography (50 g of silica gel, eluting with toluene) to give the compound (19) (0.734 g, 33.1%) as colorless oil. $^1$H-NMR(CDCl$_3$): 1.21(3H, br.t), 2.08(3H, s), 3.84(2H, s), 4.10(2H, br), 5.98(1H, d, J=3 Hz), 6.55(1H, d, J=3 Hz), 6.79(1H, br), 7.07–7.30(5H, m).

(Step 5)

Using the compound (18) or the compound (19) as a starting material, compound (XII-2) was synthesized in a manner similar to that described in Example 1 —Step 7.

The compound (XII-3) to the compound (XII-10) were synthesized by carrying out the same reactions as described above. The physical data of each compound are shown in Tables 1.

TABLE 1

| Compound No. | R$^1$ | R$^2$ | $^1$H-NMR(CDCl$_3$) |
|---|---|---|---|
| XII-2 | benzyl-CH$_2$ | Me | 2.08(3H, s), 3.98(2H, s), 5.88 (1H, s), 6.62(1H, br.s), 7.09–7.30 (5H, m) |
| XII-3 | 4-F-benzyl-CH$_2$ | Et | 1.15(3H, t, J=7.5Hz), 2.45(2H, q, J=7.5Hz), 3.96(2H, s), 5.94 (1H, s), 6.64(1H, br.s), 6.91–7.07 (4H, m) |
| XII-4 | 2-F-benzyl-CH$_2$ | Et | 1.13(3H, t, J=7.5Hz), 2.43(2H, q, J=7.5Hz), 4.00(2H, s), 5.94 (1H, s), 6.67(1H, br.s), 6.83–7.23 (4H, m) |
| XII-5 | 2-phenyl-benzyl-CH$_2$ | Et | 1.09(3H, t, J=7.2Hz), 2.34(2H; q, J=7.2Hz), 3.89(2H, s), 5.88(1H, s), 6.57(1H, br.s), 6.93(1H, m), 7.23–7.46(9H, m) |

TABLE 1-continued
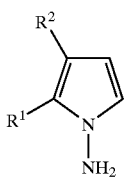
| Compound No. | R¹ | R² | ¹H-NMR(CDCl₃) |
|---|---|---|---|
| XII-6 | ![3-phenoxybenzyl] | Et | 1.13(3H, t, J=7.8Hz), 2.43(2H, q, J=7.8Hz), 3.97(2H, s), 5.92(1H, s), 6.63(1H, br.s), 6.81–7.37(10H, m) |
| XII-7 | Me | Me | 2.09(3H, s), 3.98(2H, s), 5.88(1H, s), 6.61(1H, br.s), 7.08–7.31(5H, m) |
| XII-8 | ![2-(4-fluorophenyl)benzyl] | Me | 1.96(3H, s), 3.86(2H, s), 5.83(1H, s), 6.91(1H, br.s), 7.07–7.34(8H, s) |
| XII-9 | ![4-biphenylmethyl] | Me | 2.10(3H, s), 4.03(2H, s), 5.90(1H, s), 6.70(1H, br.s), 7.15–7.57(9H, m) |
| XII-10 | ![2-(4-fluorophenyl)benzyl] | Et | 1.08(3H, t, J=7.5Hz), 2.32(2H, q, J=7.5Hz), 3.86(2H, s), 5.90(1H, s), 6.60(1H, br.s), 7.12–7.33(8H, m) |
Example 4
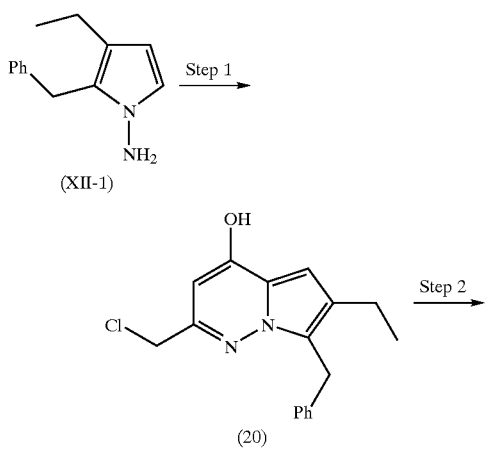
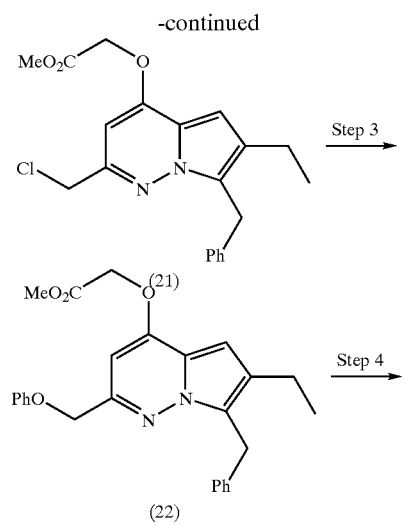

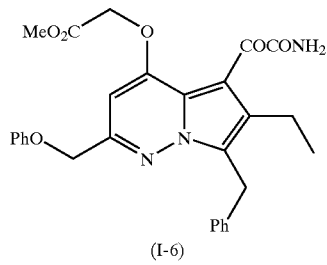

(I-6)

(Step 1)

A mixture of the compound (XII-1) (11.06 g, 54.5 mmol), ethyl 4-chloroacetoacetate (8.97 g, 54.5 mmol), p-toluenesulfonic acid monohydrate (518 mg, 2.73 mmol), and 180 ml of chloroform was heated for 4h under reflux. The generated water in situ was dehydrated by a Dean-Stark apparatus with molecular sieve 4A. To the reaction mixture were added water and sodium bicarbonate (250 mg) and the mixture was extracted with chloroform. The organic layer was dried over magnesium sulfate and concentrated in vacuo to give the compound (20) (15.17 g, 92.5%) as brown oil. $^1$H-NMR(CDCl$_3$): 1.23 (3H, t, J=7.5 Hz), 2.68(2H, q, J=7.5 Hz), 4.36 (2H, s), 4.53 (2H, s), 6.08 (1H, s), 6.51 (1H, s), 7.14–7.24 (5H, m).

(Step 2)

A mixture of the compound (20) (1.49 g, 4.95 mmol), methyl bromoacetate (0.61 ml, 6.44 mmol), potassium carbonate (684 mg, 4.95 mmol) and 15 ml of dimethylformamide was stirred for 1 h at room temperature. To the reaction mixture was added water and the mixture was extracted with toluene. The organic layer was washed with water, dried over magnesium sulfate, and concentrated in vacuo. The residue was subjected to silica gel (28 g) column chromatography, the fractions eluting with toluene were collected, and concentrated in vacuo. The residue (1.40 g) was recrystallized from ether and petroleum ether to give the compound (21) (1.19 g, 64.4%, melting point 73–73.5° C.) as white crystals. $^1$H-NMR(CDCl$_3$): 1.23 (3H, t, J=7.5 Hz), 2.67 (2H, q, J=7.5 Hz), 3.84 (3H, s), 4.35 (2H, s), 4.55 (2H, s), 4.82 (2H, s), 5.89 (1H, s), 6.62 (1H, s), 7.12–7.24 (5H, m).

(Step 3)

A mixture of the compound (21) (373 mg, 1 mmol), phenol (113 mg, 1.2 mmol), potassium carbonate (166 mg, 1.2 mmol) and 10 ml of acetone was heated for 22h under reflux in an oil bath. Acetone was removed, the residue was treated with toluene, the insoluble material was filtered off, and the solvent was removed. The residue was subjected to silica gel (13 g) column chromatography, the fractions eluting with 5% ethyl acetate-toluene were collected, and concentrated in vacuo to give the compound (22) (350 mg, 81.4%) as colorless oil. $^1$H-NMR(CDCl$_3$): 1.24 (3H, t, J=7.5 Hz), 2.69 (2H, q, J=7.5 Hz), 3.75 (3H, s), 4.3 (2H, s), 4.77(2H, s), 5.06 (2H, s), 5.96 (1H, s), 6.60 (1H, s), 6.93–7.25 (10H, m).

(Step 4)

The compound (22) (350 mg, 0.813 mmol) and N-methylmorpholine (0.18 ml, 1.63 mmol) were dissolved in 5 ml of dichloromethane. To the mixture was added a solution of oxalyl chloride (0.21 ml, 2.44 mmol) in 3 ml of dichloromethane which was cooled under ice-cooling and the resulting mixture was stirred for 2 h at the same temperature. The reaction mixture was poured into 2 ml of conc. aqueous ammonia under ice-cooling, the insoluble material was filtered off, and the filtrate was extracted with chloroform. The organic layer was washed with water, dried over magnesium sulfate, and concentrated in vacuo. The residue was subjected to silica gel (12 g) column chromatography, the fractions eluting with 50% acetonitrile-chloroform were collected, and concentrated in vacuo. The residue was recrystallized from acetone and ethyl acetate to give the compound (I-6) (375 mg, 91.9%, melting point 185–186° C.) as pale yellow crystals. $^1$H-NMR (d$_6$-DMSO): 1.04 (3H, t, J=7.2 Hz), 2.79 (2H, q, J=7.2 Hz), 3.67 (2H, s), 4.33 (2H, s), 4.99 (2H, s), 5.15 (2H, s), 6.68 (1H, s), 6.93–7.29 (10H, m), 7.40 (1H, br.s), 7.79 (1H, br.s).

Example 5

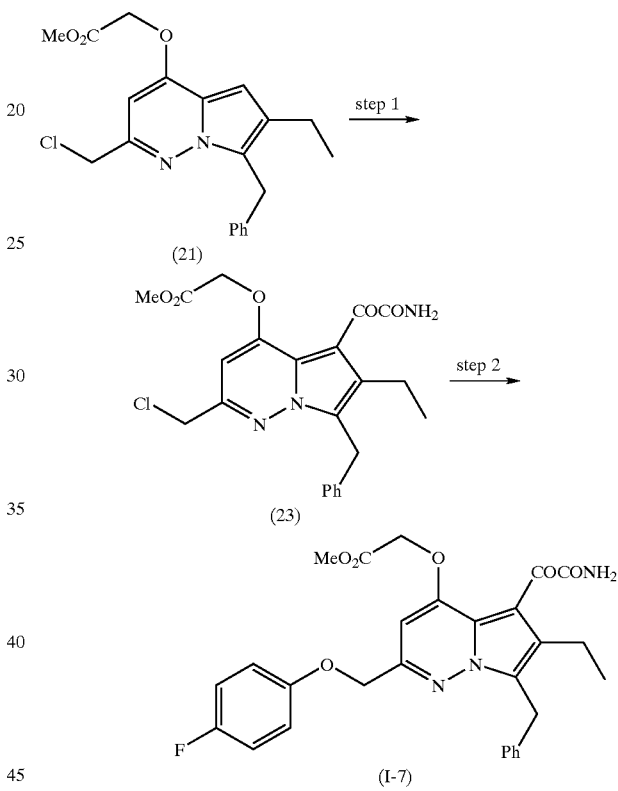

(Step 1)

The compound (21) (5.0 g, 13.4 mmol) and N, N-diisopropyl-N-ethylamine (3.5 ml, 20.1 mmol) were dissolved in 25 ml of dichloromethane. This solution was added to a solution of oxalyl chloride (3.5 ml, 40.2 mmol) in 35 ml of dichloromethane which was cooled in an ice-methanol bath (–10° C.) and the mixture was stirred for 2 h at the same temperature. The reaction mixture was poured into a mixed solution of conc. aqueous ammonia (10.7 ml) and chloroform (40 ml) under ice-cooling. The insoluble material was remove by filtration and the filtrate was extracted with chloroform. The organic layer was washed with water, dried over magnesium sulfate, and concentrated in vacuo. The residue was subjected to silica gel (42 g) column chromatography, the fractions eluting with 50% acetonitrile and chloroform were collected, and concentrated in vacuo. The residue was recrystallized from tetrahydrofuran-ethyl acetate to give the compound (23) (5.36 g, 90.0%, melting point 191–194° C.) as pale yellow crystals. $^1$H-NMR (d$_6$-DMSO): 1.03 (3H, t, J=7.5 Hz), 2.78 (2H, q, J=7.5 Hz), 3.72

(2H, s), 4.34 (2H, s), 4.76 (2H, s), 5.00 (2H, s), 6.71 (1H, s), 7.16–7.28 (5H, m), 7.42 (1H, br.s), 7.82 (1H, br.s).

(Step 2)

A mixture of the compound (23) (500 mg, 1.13 mmol), 4-fluorophenol (152 mg, 1.35 mmol), potassium carbonate (187 mg, 1.35 mmol), potassium iodide (38 mg, 0.226 mmol), and 20 ml of acetone was heated for 7 h under reflux in an oil bath. Acetone was removed, the residue was treated with toluene, the insoluble material was removed by filtration, and the filtrate was concentrated in vacuo. The residue was subjected to silica gel (9.4 g) column chromatography, the fractions eluting with 5% ethyl acetate-toluene were collected, and concentrated in vacuo. The residue was recrystallized from tetrahydrofuran and ethyl acetate to give the compound (I-7) (419 mg, 71.6%, melting point 178–179° C.) as white crystals. $^1$H-NMR (CDCl$_3$): 1.04 (3H, t, J=7.5 Hz), 2.79 (2H, q, J=7.5 Hz), 3.68 (3H, s), 4.33 (2H, s), 5.00 (2H, s), 5.13 (2H, s), 6.68 (1H, s), 7.00–7.24 (9H, m), 7.40 (1H, br.s), 7.80 (1H, br.s).

Example 6–Example 86

The compounds (I-8) to (I-84) represented by the following formula were synthesized by the same reactions described in the above Examples. The physical data were shown in Tables 2 to 11.

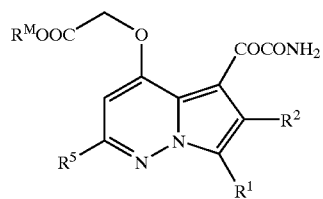

Provided that A in the Tables means a group represented by the following formula:

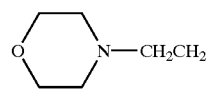

TABLE 2

| Compound No. | $R^1$ | $R^2$ | $R^5$ | $R^M$ | m.p (° C.) | $^1$H-NMR(d$_6$-DMSO) |
|---|---|---|---|---|---|---|
| I-8 | benzyl-CH$_2$ | Et | Et | Me | 183–185 | 1.16(3H, t, J=75Hz), 1.26(3H, t, J=7.5Hz), 2.73(2H, q, J=7.5 Hz), 2.85(2H, q, J=7.5Hz), 3.80(3H, s), 4.33(2H, s), 4.74 (2H, s), 5.54(1H, br), 5.94(1H, s), 6.67(1H, br), 7.14–7.28(5H, m) |
| I-9 | benzyl-CH$_2$ | Et | n-Pr | Me | 204–206 | 0.93(3H, t, J=7.2Hz), 1.16(3H, t, J=7.5Hz), 1.70(2H, m, J=7.2 Hz), 2.66(2H, t, J=7.2Hz), 2.85 (2H, q, J=7.5Hz), 3.79(3H, s), 4.33(2H, s), 4.74(2H, s), 5.56 (1H, br), 5.93(1H, s), 6.68(1H, br), 7.12–7.27(5H, m) |
| I-10 | benzyl-CH$_2$ | Et | i-Pr | Me | 174–175 | 1.17(3H, t, J=7.2Hz), 1.25(6H, d, J=7.2Hz), 2.87(2H, q, J=7.2 Hz), 2.96(1H, m, J=7.2Hz), 3.80(3H, s), 4.32(2H, s), 4.75 (2H, s), 5.53(1H, br.s), 5.96 (1H, s), 6.67(1H, br.s), 7.13–7.30(5H, m) |
| I-11 | benzyl-CH$_2$ | Et | Ph | Me | 236–239 | 1.09(3H, t, J=7.4Hz), 2.84(2H, q, J=7.4Hz), 3.72(3H, s), 4.42 (2H, s), 5.14(2H, s), 7.10–8.05 (10H, m), 7.42(1H, br.s), 7.82 (1H, br.s) |
| I-12 | 4-F-benzyl-CH$_2$ | Et | Me | Me | 252–254 | 1.02(3H, t, J=7.2Hz), 2.41(3H, s), 2.76(2H, q, J=7.2Hz), 3.72 (3H, s), 4.30(2H, s), 4.95(2H, s), 6.50(1H, s), 7.07(2H, t, J=8.7Hz), 7.23(2H, m), 7.35 (1H, br.s), 7.74(1H, br.s), 8.00–8.04(2H, m) |
| I-13 | 4-F-benzyl-CH$_2$ | Et | Ph | Me | 253–255 | 1.09(3H, t, J=7.5Hz), 2.84(2H, q, J=7.5Hz), 3.72(3H, s), 4.41 (2H, s), 5.14(2H, s), 7.09(1H, t, J=9.0Hz), 7.10(1H, s), 7.30 (2H, dd, J=9.0, 5.7Hz), 7.41 (1H, br.s), 7.50–7.58(3H, m), 7.81(1H, br.s), 8.00–8.04(2H, m) |

TABLE 3

| Compound No. | R¹ | R² | R⁵ | Rᴹ | m.p. (° C.) | ¹H-NMR(d₆-DMSO) |
|---|---|---|---|---|---|---|
| I-14 | 4-F-C₆H₄-CH₂ | Et | CF₃ | Me | 200–202 | 1.18(3H, t, J=7.5Hz), 2.88(2H, q, J=7.5Hz), 3.82(3H, s), 4.32 (2H, s), 4.81(2H, s), 5.58(1H, br.s) 6.29(1H, s), 6.77(1H, br.s), 6.93(2H, t, J=8.7Hz), 7.23(2H, dd, J=8.7, 5.4Hz) (by CDCl₃) |
| I-15 | 2-F-C₆H₄-CH₂ | Et | Ph | Me | 244–246 | 1.09(3H, t, J=7.5Hz), 2.83(2H, q, J=7.5Hz), 3.72(3H, s), 4.43 (2H, s), 5.14(2H, s), 7.03–7.28 (5H, m), 7.42(1H, br.s), 7.49–7.56(3H, m), 7.81(1H, br.s), 7.97–8.01(2H, m) |
| I-16 | C₆H₅-CH₂ | Me | Me | H | 271–272 (d) | 2.33(3H, s), 2.41(3H, s), 4.31 (2H, s), 4.84(2H, s), 6.45(1H, s), 7.12–7.30(5H, m), 7.39(1H, br.s), 7.75(1H, br.s) |
| I-17 | C₆H₅-CH₂ | Me | Ph | H | 253–254 (d) | 2.42(3H, s), 4.41(2H, s), 5.05 (2H, s), 7.05(1H, s), 7.16–8.07 (10H, m), 7.44(1H, s), 7.81(1H, s) |
| I-18 | C₆H₅-CH₂ | Et | Et | H | 223–225 (d) | 1.04(3H, t, J=7.2Hz), 1.21(3H, t, J=7.2Hz), 2.70(2H, q, J=7.5 Hz), 2.79(2H, q, J=7.5Hz), 4.31(2H, s), 4.84(2H, s), 6.45 (1H, s), 7.15–7.28(5H, m), 7.36 (1H, br.s), 7.75(1H, br.s) |
| I-19 | C₆H₅-CH₂ | Et | n-Pr | H | 231–233 (d) | 0.87(3H, t, J=7.2Hz), 1.04(3H, t, J=7.2Hz), 1.67(2H, m, J=7.5 Hz), 2.65(2H, q, J=7.2Hz), 2.79(2H, q, J=7.5Hz), 4.31 (2H, s), 4.86(2H, s), 6.46(1H, s), 7.13–7.25(5H, m), 7.36(1H, s), 7.75(1H, s) |
| I-20 | C₆H₅-CH₂ | Et | i-Pr | H | 234–236 (d) | 1.06(3H, t, J=7.2Hz), 1.23(6H, d, J=6.6Hz), 2.81(2H, q, J=7.5 Hz), 2.98(1H, m, J=6.6Hz), 4.30(2H, s), 4.87(2H, s), 6.48 (1H, s), 7.14–7.28(5H, m), 7.36 (1H, br.s), 7.75(1H, br.s) |
| I-21 | C₆H₅-CH₂ | Et | Ph | H | 244–246 (d) | 1.09(3H, t, J=7.2Hz), 2.85(2H, q, J=7.2Hz), 4.42(2H, s), 5.04 (2H, s), 7.04(1H, s), 7.14–8.03 (10H, m), 7.43(1H, br.s), 7.81 (1H, br.s) |

TABLE 4

| Compound No. | R¹ | R² | R⁵ | Rᴹ | m.p. (° C.) | ¹H-NMR(d₆-DMSO) |
|---|---|---|---|---|---|---|
| I-22 | 4-F-C₆H₄-CH₂ | Et | Me | H | 238–240 | 1.03(3H, t, J=7.5Hz), 2.40(3H, s), 2.76(2H, q, J=7.5Hz), 4.30 (2H, s), 4.84(2H, s), 6.45(1H, s), 7.07(2H, t, J=8.7Hz), 7.23 (2H, dd, J=8.7, 5.7Hz), 7.37(1H, br.s), 7.75(1H, br.s), 13.26(1H, br. s) |

TABLE 4-continued

| Compound No. | R¹ | R² | R⁵ | Rᴹ | m.p. (°C.) | ¹H-NMR(d₆-DMSO) |
|---|---|---|---|---|---|---|
| I-23 | 4-F-C₆H₄-CH₂ | Et | Ph | H | 250–252 | 1.09(3H, t, J=7.5Hz), 2.84(2H, q, J=7.5Hz), 4.41(2H, s), 5.04 (2H, s), 7.04(1H, s), 7.09(2H, t, J=8.7Hz), 7.31(2H, dd, J=8.7, 5.7Hz), 7.43(1H, br.s), 7.50–7.58(3H, m), 7.81(1H, br.s), 8.00–8.04(2H, m), 13.26(1H, br.s) |
| I-24 | 4-F-C₆H₄-CH₂ | Et | CF₃ | H | 248–250 | 1.06(3H, t, J=7.5Hz), 2.83(2H, q, J=7.5Hz), 4.35(2H, s), 5.04 (2H, s), 6.97(1H, s), 7.09(2H, t, J=8.7Hz), 7.26(2H, dd, J=8.7, 5.7Hz), 7.53(1H, br.s), 7.90 (1H, br.s), 13.40(1H, br.s) |
| I-25 | 2-F-C₆H₄-CH₂ | Et | Ph | H | 252–254 | 1.09(3H, t, J=7.5Hz), 2.83(2H, q, J=7.5Hz), 4.43(2H, s), 5.04 (2H, s), 7.03–7.28(5H, m), 7.44 (1H, br.s), 7.48–7.57(3H, m), 7.82(1H, br.s), 7.96–8.01(2H, m), 13.26(1H, br.s) |
| I-26 | C₆H₅-CH₂ | Me | Me | Me | 163–165 | 2.33(3H, s), 2.41(3H, s), 3.71 (3H, s), 4.31(2H, s), 3.95(2H, s), 6.49(1H, s), 7.13–7.30(5H, m), 7.37(1H, br.s), 7.77(1H, br.s) |
| I-27 | C₆H₅-CH₂ | Et | —CH₂SPh | Me | 189–192 | 0.99(3H, t, J=7.2Hz), 2.75(2H, q, J=7.2Hz), 3.70(3H, s), 4.25 (2H, s), 4.29(2H, s), 4.93(2H, s), 6.62(1H, s), 7.14–7.38(11H, m), 7.77(1H, br.s) |
| I-28 | C₆H₅-CH₂ | Et | —CH₂Cl | Bn | 172–173 | 1.14(3H, t, J=7.5Hz), 2.84(2H, q, J=7.5Hz), 2.34(2H, s), 4.50 (2H, s), 4.80(2H, s), 5.24(2H, s), 5.41(1H, br.s), 6.17(1H, s), 6.58(1H, br.s), 7.22(5H, m), 7.36(5H, s) |

TABLE 5

| Compound No. | R¹ | R² | R⁵ | Rᴹ | m.p. (°C.) | ¹H-NMR(d₆-DMSO) |
|---|---|---|---|---|---|---|
| I-29 | C₆H₅-CH₂ | Et | pyrrolidin-1-yl-CH₂ | Bn | 185–186 | 1.16(3H, t, J=7.2Hz), 1.76(4H, br.s), 2.48(4H, br.s), 2.85(2H, q, J=7.2Hz), 3.63(2H, s), 4.34 (2H, s), 4.81(2H, s), 5.22(2H, s), 5.36(1H, br.s), 6.33(1H, s), 6.54(1H, br.s), 7.22(5H, m), 7.36(5H, s) |
| I-30 | C₆H₅-CH₂ | Et | morpholin-4-yl-CH₂ | Bn | 183–184 | 1.17(3H, t, J=7.4Hz), 2.37(4H, m), 2.86(2H, q, J=7.4Hz), 3.47 (2H, s), 3.63(4H, m), 4.32(2H, s), 4.80(2H, s), 5.22(2H, s), 5.40(1H, br.s), 6.27(1H, s), 6.56(1H, br.s), 7.12–7.22(5H, m), 7.35(5H, s) |
| I-31 | C₆H₅-CH₂ | Et | 4-Me-piperazin-1-yl-CH₂ | Bn | 202–203 | 1.17(3H, t, J=7.2Hz), 2.29(3H, s), 2.43(8H, br.s), 2.86(2H, q, J=7.2Hz), 3.48(2H, s), 4.32 (2H, s), 4.79(2H, s), 5.22(2H, s), 5.39(1H, br.s), 6.28(1H, s), 6.55(1H, br.s), 7.16–7.24(5H, m), 7.35(5H, s) |

TABLE 5-continued

| Compound No. | R¹ | R² | R⁵ | R^M | m.p. (° C.) | ¹H-NMR(d₆-DMSO) |
|---|---|---|---|---|---|---|
| I-32 | 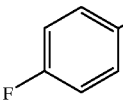 | Et | 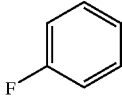 | Me | 274–276 (d) | 1.09(3H, t, J=7.2Hz), 2.84(2H, q, J=7.2Hz), 2.72(3H, s), 4.40 (2H, s), 5.13(2H, s), 7.06–7.42 (8H, m), 7.81(1H, br.s), 8.07–8.12(2H, m) |
| I-33 | 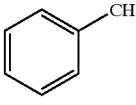 | Et | 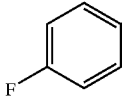 | Me | 249–253 (d) | 1.08(3H, t, J=7.2Hz), 2.84(2H, q, J=7.2Hz), 3.72(3H, s), 4.42 (2H, s), 5.13(2H, s), 7.10–7.41 (9H, m), 7.80(1H, br.s), 8.06–8.11(2H, m) |
| I-34 | 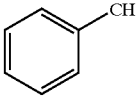 | Et | 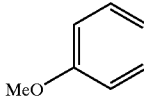 | Me | 215–217 (d) | 1.09(3H, t, J=7.5Hz), 2.84(2H, q, J=7.5Hz), 2.72(3H, s), 3.83 (3H, s), 4.40(2H, s), 5.13(2H, s), 7.04–7.28(8H, m), 7.40(1H, br.s), 7.79(1H, br.s), 7.99(2H, d, J=8.7Hz) |
| I-35 | 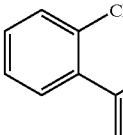 | Et | Me | Me | 187–189 | 0.89(3H, t, J=7.2Hz), 2.34(3H, s), 2.55(2H, q, J=7.2Hz), 3.72 (3H, s), 4.25(2H, s), 4.93(2H, s), 6.45(1H, s), 6.85–7.48(10H, m), 7.72(1H, br.s) |
| I-36 | 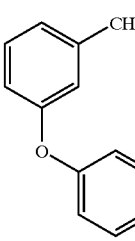 | Et | Me | Me | 201–202 | 1.01(3H, t, J=7.4Hz), 2.34(3H, s), 2.76(2H, J=7.4Hz), 3.72 (3H, s), 4.28(2H, s), 4.94(2H, s), 6.48(1H, s), 6.79–7.41(10H, m), 7.74(1H, br.s) |

TABLE 6

| Compound No. | R¹ | R² | R⁵ | R^M | m.p. (° C.) | ¹H-NMR(d₆-DMSO) |
|---|---|---|---|---|---|---|
| I-37 | 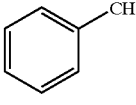 | Et | 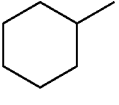 | Me | 207–209 (d) | 1.04(3H, t, J=7.5Hz), 1.20–1.90 (10H, m), 2.59–2.70(1H, m), 2.79(2H, q, J=7.5Hz), 3.71 (3H, s), 4.30(2H, s), 4.97(2H, s), 6.54(1H, s), 7.12–7.26(5H, m), 7.34(1H, br.s), 7.74(1H, br.s) |
| I-38 | 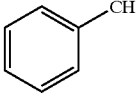 | Et | 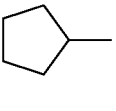 | Me | 160–162 (d) | 1.06(3H, t, J=7.5Hz), 1.56–2.01 (8H, m), 2.80(2H, q, J=7.5Hz), 3.08–3.18(1H, m), 3.71(3H, s), 4.29(2H, s), 4.98(2H, s), 6.49 (1H, s), 7.13–7.27(5H, m), 7.35 (1H, br.s), 7.74(1H, br.s) |
| I-39 | 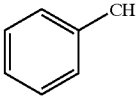 | Et | 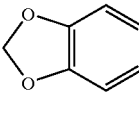 | Me | 245–247 (d) | 1.09(3H, t, J=7.5Hz), 2.84 (2H, q, J=7.5Hz), 3.72(3H, s), 4.40(2H, s), 5.12(2H, s), 6.11 (2H, s), 7.04(1H, s), 7.07(1H, d), 7.13–7.28(5H, m), 7.41(1H, br.s), 7.56–7.61(2H, m), 7.80 (1H, br.s) |
| I-40 | 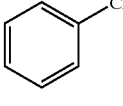 | Me | Et | Me | 194–196 | 1.23(3H, t, J=7.4Hz), 2.35(3H, s), 2.72(2H, q, J=7.4Hz), 3.71 (3H, s), 4.30(2H, s), 4.96(2H, s), 6.51(1H, s), 7.20–7.25(5H, m), 7.36(1H, br.s), 7.74(1H, br.s) |

TABLE 6-continued

| Compound No. | R¹ | R² | R⁵ | R^M | m.p. (°C.) | ¹H-NMR(d₆-DMSO) |
|---|---|---|---|---|---|---|
| I-41 | PhCH₂ | Me | n-Pr | Me | 210–211 | 0.89(3H, t, J=7.4Hz), 1.69(2H, m, J=7.4Hz), 2.35(3H, s), 2.67 (2H, t, J=7.4Hz), 3.71(3H, s), 4.30(2H, s), 4.96(2H, s), 6.51 (1H, s), 7.12–7.23(5H, m), 7.36 (1H, br.s), 7.75(1H, br.s) |
| I-42 | PhCH₂ | Me | PhCH₂ | Me | 204–206 | 2.37(3H, s), 3.65(3H, s), 4.02 (2H, s), 4.28(2H, s), 4.92(2H, s), 6.52(1H, s), 7.21(5H, m), 7.26(5H, m), 7.35(1H, br.s), 7.74(1H, br.s) |
| I-43 | PhCH₂ | Me | MeSCH₂— | Me | 210–211 | 1.80(3H, s), 2.36(3H, s), 3.70 (5H, s), 4.30(2H, s), 4.96(2H, s), 6.58(1H, s), 7.10–7.26(5H, m), 7.39(1H, br.s), 7.77(1H, br.s) |
| I-44 | PhCH₂ | Me | MeOCH₂— | Me | 228–229 (d) | 2.35(3H, s), 3.29(3H, s), 3.71 (3H, s), 4.32(2H, s), 4.46(2H, s), 5.00(2H, s), 6.55(1H, s), 7.13–7.30(5H, m), 7.39(1H, br.s), 7.77(1H, br.s) |

TABLE 7

| Compound No. | R¹ | R² | R⁵ | R^M | m.p. (°C.) | ¹H-NMR(d₆-DMSO) |
|---|---|---|---|---|---|---|
| I-45 | PhCH₂ | Me | Ph | Me | 251–252 | 2.42(3H, s), 3.71(3H, s), 4.41 (2H, s), 5.14(2H, s), 3.10(1H, s), 7.16–8.06(10H, m), 7.46(1H, br.s), 7.81(1H, br.s) |
| I-46 | PhCH₂ | Et | 4-MeO-C₆H₄-OCH₂ | Me | 167–168 | 1.04(3H, t, J=7.5Hz), 2.79(2H, q, J=7.5Hz), 3.68(3H, s), 4.33 (2H, s), 4.99(2H, s), 5.08(2H, s), 6.66(1H, s), 6.80(2H, d, J=9 Hz), 6.92(2H, d, J=9Hz), 7.17–7.28(5H, m), 7.40(1H, s), 7.79 (1H, br.s) |
| I-47 | PhCH₂ | Et | 3,4-(MeO)₂-C₆H₃-OCH₂ | Me | 176–179 | 1.03(3H, t, J=7.4Hz), 2.79(2H, q, J=7.4Hz), 3.67(3H, s), 3.68 (3H, s), 3.71(3H, s), 4.34(2H, s), 5.00(2H, s), 5.09(2H, s), 6.45–7.28(8H, m), 7.41(1H, br.s), 7.80(1H, br.s) |
| I-48 | PhCH₂ | Et | 4-Me-C₆H₄-OCH₂ | Me | 191–192 | 1.04(3H, t, J=7.2Hz), 2.21(3H, s), 2.79(2H, q, J=7.2Hz), 3.67 (3H, s), 4.33(2H, s), 4.99(2H, s), 5.11(2H, s), 6.66(1H, s), 6.88(2H, d, J=9Hz), 7.05(2H, d, J=9Hz), 7.16–7.28(5H, m), 7.39(1H, br.s), 7.79(1H, br.s) |
| I-49 | PhCH₂ | Et | (succinimido)CH₂ | Me | 188–189 | 1.04(3H, t, J=7.0Hz), 2.60(4H, s), 2.78(2H, J=7.0Hz), 3.73 (3H, s), 4.22(2H, s), 4.66(2H, s), 4.97(2H, s), 6.54(1H, s), 7.20–7.28(5H, m), 7.40(1H, br.s), 7.79(1H, br.s) |

TABLE 7-continued

| Compound No. | R¹ | R² | R⁵ | R^M | m.p. (° C.) | ¹H-NMR(d₆-DMSO) |
|---|---|---|---|---|---|---|
| I-50 | benzyl (PhCH₂) | Et | N₃CH₂— | Bn | 178–179 | 1.03(3H, t, J=7.4Hz), 2.79(2H, q, J=7.4Hz), 4.35(2H, s), 4.49 (2H, s), 5.07(2H, s), 5.21(2H, s), 6.63(1H, s), 7.12–7.36(10H, m), 7.41(1H, br.s), 7.81(1H, br.s) |
| I-51 | Me | Me | 3-methylbenzyl | Me | 199–201 | 2.29(3H, s), 2.43(3H, s), 3.63 (3H, s), 4.04(2H, s), 4.92(2H, s), 6.46(1H, s), 7.21–7.32(6H, m), 7.71(1H, br.s) |
| I-52 | 2-(4-fluorophenyl)benzyl | Me | Me | Me | 194–196 | 2.18(3H, s), 2.37(3H, s), 3.79 (3H, s), 4.24(2H, s), 4.74(2H, s), 5.91(1H, s), 5.94(1H, br.s), 6.71(1H, br.s), 6.98–7.38(8H, m) |

TABLE 8

| Compound No. | R¹ | R² | R⁵ | R^M | m.p. (° C.) | ¹H-NMR(d₆-DMSO) |
|---|---|---|---|---|---|---|
| I-53 | 4-phenylbenzyl | Me | Me | Me | 234–236 | 2.44(3H, s), 2.46(3H, s), 3.80 (3H, s), 4.37(2H, s), 4.75(2H, s), 5.45(1H, br.s), 5.96(1H, s), 6.67(1H, br.s), 7.29–7.56(9H, m) |
| I-54 | 2-(4-fluorophenyl)benzyl | Et | Me | Me | 190–192 | 0.96(3H, t, J=7.2Hz), 2.37(3H, s), 2.60(2H, q, J=7.2 Hz), 3.81 (3H, s), 4.25(2H, s), 4.73(2H, s), 5.43(1H, br.s), 5.90(1H, s), 6.60(1H, br.s), 6.95–7.37(8H, m) |
| I-55 | benzyl | Me | Me | Et | 197–199 | 1.21(3H, t, J=7.2Hz), 2.32(3H, s), 2.41(3H, s), 4.18(2H, q, J=7.2Hz), 4.31(2H, s), 4.93 (2H, s), 6.47(1H, s), 7.16–7.28 (5H, m), 7.35(1H, br.s), 7.72 (1H, br.s) |
| I-56 | benzyl | Me | Me | A | 160–161 | 2.41(3H, s), 2.44(3H, s), 2.50 (4H, br.s), 2.65(2H, br.s), 3.71 (4H, m), 4.33(4H, s), 4.75(2H, s), 5.94(1H, br), 5.98(1H, s), 6.94(1H, br), 7.15–7.24(5H, m) |
| I-57 | benzyl | Et | phenoxymethyl (OCH₂-Ph) | H | 218–220 (d) | 1.04(3H, t, J=7.5Hz), 2.80(2H, q, J=7.5Hz), 4.34(2H, s), 4.88 (2H, s), 5.14(2H, s), 6.66(1H, s), 6.93–7.30(10H, m), 7.41(1H, br.s), 7.80(1H, br.s) |
| I-58 | benzyl | Et | phenylthiomethyl (SCH₂-Ph) | H | 226–228 (d) | 0.99(3H, t, J=7.2Hz), 2.74(2H, q, J=7.2Hz), 4.25(2H, s), 4.28 (2H, s), 4.83(2H, s), 6.60(1H, s), 7.14–7.39(11H, m), 7.78(1H, br.s), 13.33(1H, br) |

TABLE 8-continued

| Compound No. | R¹ | R² | R⁵ | Rᴹ | m.p. (° C.) | ¹H-NMR(d₆-DMSO) |
|---|---|---|---|---|---|---|
| I-59 | 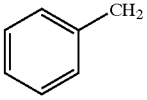 | Et | 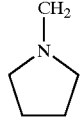 | H | 228–231 (d) | 1.05(3H, t, J=7.4Hz), 1.77(4H, br.s), 2.80(2H, q, J=7.4Hz), 2.86(4H, br.s), 4.09(2H, s), 4.34(2H, s), 4.66(2H, s), 6.65 (1H, s), 7.16–7.28(5H, m) |
| I-60 | 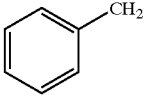 | Et | 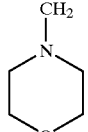 | H | 167–168 | 1.06(3H, t, J=7.2Hz), 2.35(4H, m), 2.80(2H, q, J=7.2Hz), 3.53 (4H, m), 4.31(2H, s), 4.87(2H, s), 6.50(1H, s), 7.12–7.24(5H, m), 7.39(1H, br.s), 7.78(1H, br.s) |

TABLE 9

| Compound No. | R¹ | R² | R⁵ | Rᴹ | m.p. (° C.) | ¹H-NMR(d₆-DMSO) |
|---|---|---|---|---|---|---|
| I-61 | 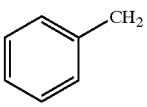 | Et | 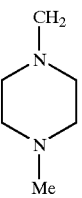 | H | 249–250 (d) | 1.05(3H, t, J=7.2Hz), 2.32(3H, s), 2.44(4H, br.s), 2.55(4H, br.s), 2.79(2H, q, J=7.2Hz), 3.52(2H, s), 4.31(2H, s), 4.67 (2H, s), 6.39(1H, s), 7.10–7.25 (5H, m), 7.37(1H, br.s), 7.79 (1H, br.s) |
| I-62 | 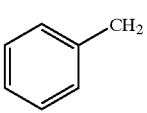 | Et | 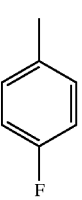 | H | 245–248 (d) | 1.09(3H t, J=7.5Hz), 2.84(2H, q, J=7.5Hz), 4.40(2H, s), 5.04 (2H, s), 7.05–7.43(8H, m), 7.82 (1H, br.s), 8.06–8.12(2H, m) |
| I-63 | 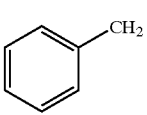 | Et | 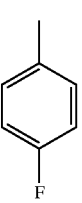 | H | 250–253 (d) | 1.09(3H, t, J=7.5Hz), 2.84(2H, q, J=7.5Hz), 4.41(2H, s), 5.04 (2H, s), 7.05(1H, s), 7.13–7.43 (8H, m), 7.82(1H, br.s), 8.05– 8.11(2H, m) |
| I-64 | 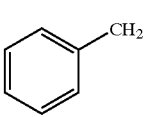 | Et | 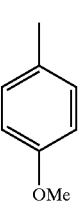 | H | 248–250 (d) | 1.09(3H, t, J=7.5Hz), 2.84(2H, q, J=7.5Hz), 3.82(3H, s), 4.40 (2H, s), 4.99(2H, s), 6.96(1H, s), 7.06(2H, d, J=8.7Hz), 7.14–7.27(5H, m), 7.41(1H, br.s), 7.80(1H, br.s), 7.96(2H, d, J=8.7Hz) |
| I-65 | 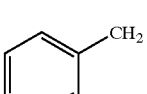 | Et | Me | H | 218–219 (d) | 0.90(3H, t, J=7.2Hz), 2.33(3H, s), 2.55(2H, q, J=7.2Hz), 4.24 (2H, s), 4.83(2H, s), 6.39(1H, s), 6.85–7.47(9H, m), 7.73(1H, br.s) |

TABLE 9-continued

| Compound No. | R¹ | R² | R⁵ | R^M | m.p. (° C.) | ¹H-NMR(d₆-DMSO) |
|---|---|---|---|---|---|---|
| I-66 | 3-phenoxybenzyl (PhO-C₆H₄-CH₂-) | Et | Me | H | 188–190 | 1.02(3H, t, J=7.0Hz), 2.34(3H, s), 2.76(2H, q, J=7.0Hz), 4.28 (2H, s), 4.84(2H, s), 6.44(1H, s), 6.80–7.41(10H, m), 7.75(1H, br.s) |
| I-67 | benzyl (PhCH₂) | Et | cyclohexylmethyl | H | 272–275 (d) | 1.04(3H, t, J=7.5Hz), 1.20–1.90 (10H, m), 2.50–2.70(1H, 2.79(2H, q, J=7.5Hz), 4.30 (2H, s), 4.86(2H, s), 6.48(1H, s), 7.12–7.26(5H, m), 7.36(1H, br.s), 7.75(1H, br.s), 13.24(1H, br.s) |
| I-68 | benzyl (PhCH₂) | Et | cyclopentylmethyl | H | 250–252 (d) | 1.06(3H, t, J=7.2Hz), 1.55–2.01 (8H, m), 2.80(2H, q, J=7.2Hz), 3.06–3.18(1H, m), 4.29(2H, s), 4.87(2H, s), 6.44(1H, s), 7.12–7.27(5H, m), 7.37(1H, br.s), 7.75(1H, br.s), 13.30(1H, br.s) |

TABLE 10

| Compound No. | R¹ | R² | R⁵ | R^M | m.p. (° C.) | ¹H-NMR(d₆-DMSO) |
|---|---|---|---|---|---|---|
| I-69 | benzyl (PhCH₂) | Et | 3,4-methylenedioxybenzyl | H | 240–243 (d) | 1.09(3H, t, J=7.5Hz), 2.84(2H, q, J=7.5Hz), 4.40(2H, s), 5.01 (2H, s), 6.11(2H, s), 6.98(1H, s), 7.06(1H, d, J=8.1Hz), 7.13–7.30(5H, m), 7.42(1H, br.s), 7.55–7.59(2H, m), 7.81(1H, br.s), 13.25(1H, br.s) |
| I-70 | benzyl (PhCH₂) | Me | Et | H | 200–201 | 1.22(3H, t, J=7.6Hz), 2.35(2H, s), 2.71(2H, q, J=7.6Hz), 4.30 (2H, s), 4.86(2H, s), 6.46(1H, s), 7.23(5H, m), 7.38(1H, br.s), 7.74(1H, br.s) |
| I-71 | benzyl (PhCH₂) | Me | n-Pr | H | 204–205 | 0.88(3H, t, J=7.0Hz), 1.68(2H, m), 2.35(3H, s), 2.66(2H, t, J=7.0Hz), 4.30(2H, s), 4.85 (2H, s), 6.46(1H, s), 7.22(5H, m), 7.34(1H, br.s), 7.74(1H, br.s) |
| I-72 | benzyl (PhCH₂) | Me | benzyl (PhCH₂) | H | 245–247 (d) | 2.37(3H, s), 4.01(2H, s), 4.28 (2H, s), 4.82(2H, s), 6.52(1H, s), 7.20(5H, m), 7.25(5H, m), 7.37(1H, br.s), 7.74(1H, br.s) |
| I-73 | benzyl (PhCH₂) | Me | MeSCH₂— | H | 228–229 (d) | 1.89(3H, s), 2.36(3H, s), 3.71 (2H, s), 4.30(2H, s), 4.85(2H, s), 6.54(1H, s), 7.22(5H, m), 7.40(1H, br.s), 7.78(1H, br.s) |
| I-74 | benzyl (PhCH₂) | Me | MeOCH₂— | H | 197–198 | 2.35(3H, s), 3.29(3H, s), 4.32 (2H, s), 4.44(2H, s), 4.89(2H, s), 6.49(1H, s), 7.22(5H, m), 7.41(1H, br.s), 7.78(1H, br.s), 13.28(1H, br) |

TABLE 10-continued

| Compound No. | R¹ | R² | R⁵ | R^M | m.p. (° C.) | ¹H-NMR(d₆-DMSO) |
|---|---|---|---|---|---|---|
| I-75 | PhCH₂ | Et | 4-F-C₆H₄-OCH₂ | H | 215–216 | 1.04(3H, t, J=7.2Hz), 2.79(2H, q, J=7.2Hz), 4.32(2H, s), 4.89 (2H, s), 5.13(2H, s), 6.65(1H, s), 6.97–7.25(9H, m), 7.41(1H, br.s), 7.79(1H, br.s), 13.30(1H, br.s) |
| I-76 | PhCH₂ | Et | 4-OMe-C₆H₄-OCH₂ | H | 218–219 | 1.04(3H, t, 7.4Hz), 2.79(2H, q, J=7.4Hz), 3.68(3H, s), 4.33 (2H, s), 4.88(2H, s), 5.07(2H, s), 6.63(1H, s), 6.79(2H, d, J=9.2Hz), 6.93(2H, d, J=9.2 Hz), 7.15–7.23(5H, m), 7.40 (1H, br.s), 7.79(1H, br.s), 13.2 (1H, br) |

TABLE 11

| Compound No. | R¹ | R² | R⁵ | R^M | m.p. (° C.) | ¹H-NMR(d₆-DMSO) |
|---|---|---|---|---|---|---|
| I-77 | PhCH₂ | Et | 3,4-diOMe-C₆H₃-OCH₂ | H | 204–206 | 1.03(3H, t, J=7.4Hz), 2.78(2H, q, J=7.4Hz), 3.67(3H, s), 3.71 (3H, s), 4.33(2H, s), 4.88(2H, s), 5.07(2H, s), 6.49(1H, d of d, J=8.8Hz, J=2.8Hz), 6.64(1H, s), 6.67(1H, d, J=2.8Hz), 6.77 (1H, d, J=8.8Hz), 7.20(5H, m), 7.40(1H, br.s), 7.80(1H, br.s) |
| I-78 | PhCH₂ | Et | 4-OMe-C₆H₄-OCH₂ | H | 219–221 | 1.04(3H, t, J=7.0Hz), 2.21(3H, s), 2.79(2H, q, J=7.0Hz), 4.33 (2H, s), 4.87(2H, s), 5.10(2H, s), 6.63(1H, s), 6.88(2H, d, J=8.8Hz), 7.04(2H, d, J=8.8 Hz), 7.21(5H, m), 7.41(1H, br.s), 7.79(1H, br.s), 13.3(1H, br) |
| I-79 | PhCH₂ | Et | succinimido-CH₂ | H | 210–212 (d) | 1.03(3H, m), 2.39–2.46(4H, m), 2.77(2H, q, J=7.0Hz), 4.30 (2H, s) 4.33(2H, s), 4.81(2H, s), 6.38(1H, s), 7.23(5H, m), 7.38(1H, br.s), 7.76(1H, br.s) |
| I-80 | PhCH₂ | Et | N₃CH₂— | H | 199–200 (d) | 1.03(3H, t, J=7.4Hz), 2.79(2H, q, J=7.4Hz), 4.35(2H, s), 4.51 (2H, s), 4.87(2H, s), 6.59(1H, s), 7.23(5H, m), 7.42(1H, br.s), 7.80(1H, br.s), 13.3(1H, br) |
| I-81 | Me | Me | PhCH₂ | H | 232–233 (d) | 2.30(3H, s), 2.42(3H, s), 4.04 (2H, s), 4.81(2H, s), 6.47(1H, s), 7.20–7.32(6H, m), 7.71(1H, br.s), 13.27(1H, br.s), |
| I-82 | 2-(4-F-C₆H₄)-C₆H₄-CH₂ | Me | Me | H | 242–244 (d) | 2.15(3H, s), 2.30(3H, s), 4.22 (2H, s), 4.65(2H, s), 6.29(1H, s), 6.86–6.89(1H, m), 7.18–7.52 (8H, m), 7.81(1H, br.s), |

TABLE 11-continued

| Compound No. | R¹ | R² | R⁵ | Rᴹ | m.p. (° C.) | ¹H-NMR(d₆-DMSO) |
|---|---|---|---|---|---|---|
| I-83 | 4-phenylbenzyl (biphenyl-CH₂) | Me | Me | H | 271–276 (d) | 2.36(3H, s), 2.41(3H, s), 4.35 (2H, s), 4.79(2H, s), 6.42(1H, s), 7.27–7.61(10H, m), 7.77(1H, br.s) |
| I-84 | (4'-fluorobiphenyl-2-yl)methyl | Et | Me | H | 214–216 (d) | 0.88(3H, t, J=7.2Hz), 2.31(3H, s), 2.54(2H, q, J=7.2Hz), 4.23 (2H, s); 4.75(2H, s), 6.35(1H, s), 6.87–7.42(9H, m), 7.76(1H, br.s) |

The compounds shown in the following Tables 12 to 17 can be synthesized in accordance with the same method describe in the above Examples. The abbreviations used in Tables 12 to 17: AA, AB, AC, AD, AE, AF, AG, AH, AI, AJ, AK, AL, AM, AN, AO, AP, AQ AR, AS, AT, AU, AV, AW, AX, AY, BA, BB, BC, BD, BE, BF, BG, BH and BI show the substituents described as follows.

AA — 2-methylbiphenyl

AB — 2-methyl-4'-methylbiphenyl

AC — 2-methyl-4'-methoxybiphenyl

AD — 2-methyl-4'-trifluoromethylbiphenyl

AE — 2-(2-methylphenyl)thiophene

AF — 2-methyl-3-phenylthiophene

AG — 2-methyl-3-(4-fluorophenyl)thiophene

AH — 2-methyl-3-(4-methylphenyl)thiophene

AI — 2-methyl-3-(4-methoxyphenyl)thiophene

AJ — 3-(2-methylphenyl)thiophene

AK — 2-methyl-5-phenylthiophene

AL — 2-methyl-5-(4-fluorophenyl)thiophene

AM — 2-methyl-5-(4-methylphenyl)thiophene

AN — 2-methyl-5-(4-methoxyphenyl)thiophene

-continued
| | |
|---|---|
| AO | 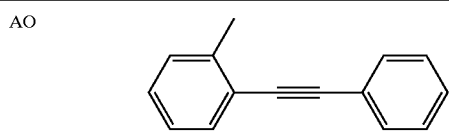 |
| AP | |
| AQ | |
| AR | |
| AS |  |
| AT | |
| AU | |
| AV | |
| AW | |
| AX | |
| AY | |
-continued
| | |
|---|---|
| AZ | 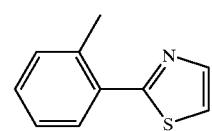 |
| BA | 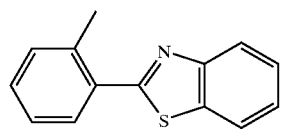 |
| BB | 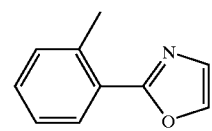 |
| BC | 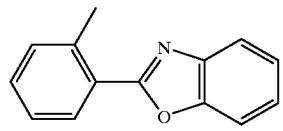 |
| BD | 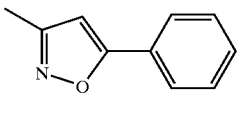 |
| BE | 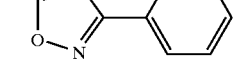 |
| BF | 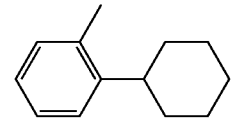 |
| BG | 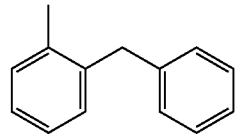 |
| BH | 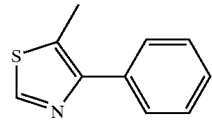 |
| BI | |

TABLE 12

Structure: Pyrrolopyridazine with HO2C-CH2-O- at 4-position, C(O)C(O)NH2 at 7-position, R37 at 2-position, R38 at 8-CH2, R39 at 6-position.

| Compound No. | R37 | R38 | R39 |
|---|---|---|---|
| II-1 | Me | AA | Me |
| II-2 | Me | AB | Me |
| II-3 | Me | AC | Me |
| II-4 | Me | AD | Me |
| II-5 | Me | AE | Me |
| II-6 | Me | AF | Me |
| II-7 | Me | AG | Me |
| II-8 | Me | AH | Me |
| II-9 | Me | AI | Me |
| II-10 | Me | AJ | Me |
| II-11 | Me | AK | Me |
| II-12 | Me | AL | Me |
| II-13 | Me | AM | Me |
| II-14 | Me | AN | Me |
| II-15 | Me | AO | Me |
| II-16 | Me | AP | Me |
| II-17 | Me | AQ | Me |
| II-18 | Me | AR | Me |
| II-19 | Me | AS | Me |
| II-20 | Me | AT | Me |
| II-21 | Me | AU | Me |
| II-22 | Me | AV | Me |
| II-23 | Me | AW | Me |
| II-24 | Me | AX | Me |
| II-25 | Me | AY | Me |
| II-26 | Me | AZ | Me |
| II-27 | Me | BA | Me |
| II-28 | Me | BB | Me |
| II-29 | Me | BC | Me |
| II-30 | Me | BD | Me |
| II-31 | Me | BE | Me |
| II-32 | Me | BF | Me |
| II-33 | Me | BG | Me |
| II-34 | Me | BH | Me |
| II-35 | Me | BI | Me |
| II-36 | Et | AA | Me |
| II-37 | Et | AB | Me |
| II-38 | Et | AC | Me |
| II-39 | Et | AD | Me |
| II-40 | Et | AE | Me |
| II-41 | Et | AF | Me |
| II-42 | Et | AG | Me |
| II-43 | Et | AH | Me |
| II-44 | Et | AI | Me |
| II-45 | Et | AJ | Me |
| II-46 | Et | AK | Me |
| II-47 | Et | AL | Me |
| II-48 | Et | AM | Me |
| II-49 | Et | AN | Me |
| II-50 | Et | AO | Me |
| II-51 | Et | AP | Me |
| II-52 | Et | AQ | Me |
| II-53 | Et | AR | Me |
| II-54 | Et | AS | Me |
| II-55 | Et | AT | Me |
| II-56 | Et | AU | Me |
| II-57 | Et | AV | Me |
| II-58 | Et | AW | Me |
| II-59 | Et | AX | Me |
| II-60 | Et | AY | Me |
| II-61 | Et | AZ | Me |
| II-62 | Et | BA | Me |
| II-63 | Et | BB | Me |
| II-64 | Et | BC | Me |
| II-65 | Et | BD | Me |
| II-66 | Et | BE | Me |
| II-67 | Et | BF | Me |
| II-68 | Et | BG | Me |
| II-69 | Et | BH | Me |
| II-70 | Et | BI | Me |
| II-71 | Ph | AA | Me |
| II-72 | Ph | AB | Me |
| II-73 | Ph | AC | Me |
| II-74 | Ph | AD | Me |
| II-75 | Ph | AE | Me |
| II-76 | Ph | AF | Me |
| II-77 | Ph | AG | Me |
| II-78 | Ph | AH | Me |
| II-79 | Ph | AI | Me |
| II-80 | Ph | AJ | Me |
| II-81 | Ph | AK | Me |
| II-82 | Ph | AL | Me |
| II-83 | Ph | AM | Me |
| II-84 | Ph | AN | Me |
| II-85 | Ph | AO | Me |
| II-86 | Ph | AP | Me |
| II-87 | Ph | AQ | Me |
| II-88 | Ph | AR | Me |
| II-89 | Ph | AS | Me |
| II-90 | Ph | AT | Me |
| II-91 | Ph | AU | Me |
| II-92 | Ph | AV | Me |
| II-93 | Ph | AW | Me |
| II-94 | Ph | AX | Me |
| II-95 | Ph | AY | Me |
| II-96 | Ph | AZ | Me |
| II-97 | Ph | BA | Me |
| II-98 | Ph | BB | Me |
| II-99 | Ph | BC | Me |
| II-100 | Ph | BD | Me |
| II-101 | Ph | BE | Me |
| II-102 | Ph | BF | Me |
| II-103 | Ph | BG | Me |
| II-104 | Ph | BH | Me |
| II-105 | Ph | BI | Me |

TABLE 13

Structure: Pyrrolopyridazine with HO2C-CH2-O- at 4-position, C(O)C(O)NH2 at 7-position, R37 at 2-position, R38 at 8-CH2, R39 at 6-position.

| Compound No. | R37 | R38 | R39 |
|---|---|---|---|
| II-106 | Me | AA | Et |
| II-107 | Me | AB | Et |
| II-108 | Me | AC | Et |
| II-109 | Me | AD | Et |
| II-110 | Me | AE | Et |
| II-111 | Me | AF | Et |
| II-112 | Me | AG | Et |
| II-113 | Me | AH | Et |
| II-114 | Me | AI | Et |
| II-115 | Me | AJ | Et |
| II-116 | Me | AK | Et |
| II-117 | Me | AL | Et |
| II-118 | Me | AM | Et |
| II-119 | Me | AN | Et |

TABLE 13-continued

| | | | |
|---|---|---|---|
| II-120 | Me | AO | Et |
| II-121 | Me | AP | Et |
| II-122 | Me | AQ | Et |
| II-123 | Me | AR | Et |
| II-124 | Me | AS | Et |
| II-125 | Me | AT | Et |
| II-126 | Me | AU | Et |
| II-127 | Me | AV | Et |
| II-128 | Me | AW | Et |
| II-129 | Me | AX | Et |
| II-130 | Me | AY | Et |
| II-131 | Me | AZ | Et |
| II-132 | Me | BA | Et |
| II-133 | Me | BB | Et |
| II-134 | Me | BC | Et |
| II-135 | Me | BD | Et |
| II-136 | Me | BE | Et |
| II-137 | Me | BF | Et |
| II-138 | Me | BG | Et |
| II-139 | Me | BH | Et |
| II-140 | Me | BI | Et |
| II-141 | Et | BA | Et |
| II-142 | Et | BB | Et |
| II-143 | Et | BC | Et |
| II-144 | Et | BD | Et |
| II-145 | Et | BE | Et |
| II-146 | Et | BF | Et |
| II-147 | Et | BG | Et |
| II-148 | Et | BH | Et |
| II-149 | Et | BI | Et |
| II-150 | Et | BJ | Et |
| II-151 | Et | BK | Et |
| II-152 | Et | BL | Et |
| II-153 | Et | BM | Et |
| II-154 | Et | BN | Et |
| II-155 | Et | BO | Et |
| II-156 | Et | BP | Et |
| II-157 | Et | BQ | Et |
| II-158 | Et | BR | Et |
| II-159 | Et | BS | Et |
| II-160 | Et | BT | Et |
| II-161 | Et | BU | Et |
| II-162 | Et | BV | Et |
| II-163 | Et | BW | Et |
| II-164 | Et | BX | Et |
| II-165 | Et | BY | Et |
| II-166 | Et | BZ | Et |
| II-167 | Et | CA | Et |
| II-168 | Et | CB | Et |
| II-169 | Et | CC | Et |
| II-170 | Et | CD | Et |
| II-171 | Et | CE | Et |
| II-172 | Et | CF | Et |
| II-173 | Et | CG | Et |
| II-174 | Et | CH | Et |
| II-175 | Et | CI | Et |
| II-176 | Ph | BA | Et |
| II-177 | Ph | BB | Et |
| II-178 | Ph | BC | Et |
| II-179 | Ph | BD | Et |
| II-180 | Ph | BE | Et |
| II-181 | Ph | BF | Et |
| II-182 | Ph | BG | Et |
| II-183 | Ph | BH | Et |
| II-184 | Ph | BI | Et |
| II-185 | Ph | BJ | Et |
| II-186 | Ph | BK | Et |
| II-187 | Ph | BL | Et |
| II-188 | Ph | BM | Et |
| II-189 | Ph | BN | Et |
| II-190 | Ph | BO | Et |
| II-191 | Ph | BP | Et |
| II-192 | Ph | BQ | Et |
| II-193 | Ph | BR | Et |
| II-194 | Ph | BS | Et |
| II-195 | Ph | BT | Et |
| II-196 | Ph | BU | Et |
| II-197 | Ph | BV | Et |
| II-198 | Ph | BW | Et |
| II-199 | Ph | BX | Et |
| II-200 | Ph | BY | Et |
| II-201 | Ph | BZ | Et |
| II-202 | Ph | CA | Et |
| II-203 | Ph | CB | Et |
| II-204 | Ph | CC | Et |
| II-205 | Ph | CD | Et |
| II-206 | Ph | CE | Et |
| II-207 | Ph | CF | Et |
| II-208 | Ph | CG | Et |
| II-209 | Ph | CH | Et |
| II-210 | Ph | CI | Et |

TABLE 14

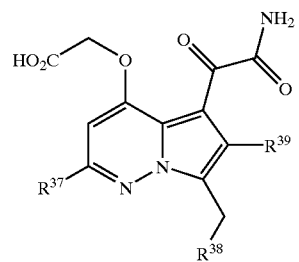

| Compound No. | $R^{37}$ | $R^{38}$ | $R^{39}$ |
|---|---|---|---|
| II-211 | Me | AA | Me |
| II-212 | Me | AB | Me |
| II-213 | Me | AC | Me |
| II-214 | Me | AD | Me |
| II-215 | Me | AE | Me |
| II-216 | Me | AF | Me |
| II-217 | Me | AG | Me |
| II-218 | Me | AH | Me |
| II-219 | Me | AI | Me |
| II-220 | Me | AJ | Me |
| II-221 | Me | AK | Me |
| II-222 | Me | AL | Me |
| II-223 | Me | AM | Me |
| II-224 | Me | AN | Me |
| II-225 | Me | AO | Me |
| II-226 | Me | AP | Me |
| II-227 | Me | AQ | Me |
| II-228 | Me | AR | Me |
| II-229 | Me | AS | Me |
| II-230 | Me | AT | Me |
| II-231 | Me | AU | Me |
| II-232 | Me | AV | Me |
| II-233 | Me | AW | Me |
| II-234 | Me | AX | Me |
| II-235 | Me | AY | Me |
| II-236 | Me | AZ | Me |
| II-237 | Me | BA | Me |
| II-238 | Me | BB | Me |
| II-239 | Me | BC | Me |
| II-240 | Me | BD | Me |
| II-241 | Me | BE | Me |
| II-242 | Me | BF | Me |
| II-243 | Me | BG | Me |
| II-244 | Me | BH | Me |
| II-245 | Me | BI | Me |
| II-246 | Et | AA | Me |
| II-247 | Et | AB | Me |
| II-248 | Et | AC | Me |
| II-249 | Et | AD | Me |
| II-250 | Et | AE | Me |
| II-251 | Et | AF | Me |
| II-252 | Et | AG | Me |
| II-253 | Et | AH | Me |
| II-254 | Et | AI | Me |
| II-255 | Et | AJ | Me |

TABLE 14-continued

| | | | |
|---|---|---|---|
| II-256 | Et | AK | Me |
| II-257 | Et | AL | Me |
| II-258 | Et | AM | Me |
| II-259 | Et | AN | Me |
| II-260 | Et | AO | Me |
| II-261 | Et | AP | Me |
| II-262 | Et | AQ | Me |
| II-263 | Et | AR | Me |
| II-264 | Et | AS | Me |
| II-265 | Et | AT | Me |
| II-266 | Et | AU | Me |
| II-267 | Et | AV | Me |
| II-268 | Et | AW | Me |
| II-269 | Et | AX | Me |
| II-270 | Et | AY | Me |
| II-271 | Et | AZ | Me |
| II-272 | Et | BA | Me |
| II-273 | Et | BB | Me |
| II-274 | Et | BC | Me |
| II-275 | Et | BD | Me |
| II-276 | Et | BE | Me |
| II-277 | Et | BF | Me |
| II-278 | Et | BG | Me |
| II-279 | Et | BH | Me |
| II-280 | Et | BI | Me |
| II-281 | Ph | AA | Me |
| II-282 | Ph | AB | Me |
| II-283 | Ph | AC | Me |
| II-284 | Ph | AD | Me |
| II-285 | Ph | AE | Me |
| II-286 | Ph | AF | Me |
| II-287 | Ph | AG | Me |
| II-288 | Ph | AH | Me |
| II-289 | Ph | AI | Me |
| II-290 | Ph | AJ | Me |
| II-291 | Ph | AK | Me |
| II-292 | Ph | AL | Me |
| II-293 | Ph | AM | Me |
| II-294 | Ph | AN | Me |
| II-295 | Ph | AO | Me |
| II-296 | Ph | AP | Me |
| II-297 | Ph | AQ | Me |
| II-298 | Ph | AR | Me |
| II-299 | Ph | AS | Me |
| II-300 | Ph | AT | Me |
| II-301 | Ph | AU | Me |
| II-302 | Ph | AV | Me |
| II-303 | Ph | AW | Me |
| II-304 | Ph | AX | Me |
| II-305 | Ph | AY | Me |
| II-306 | Ph | AZ | Me |
| II-307 | Ph | BA | Me |
| II-308 | Ph | BB | Me |
| II-309 | Ph | BC | Me |
| II-310 | Ph | BD | Me |
| II-311 | Ph | BE | Me |
| II-312 | Ph | BF | Me |
| II-313 | Ph | BG | Me |
| II-314 | Ph | BH | Me |
| II-315 | Ph | BI | Me |

TABLE 15

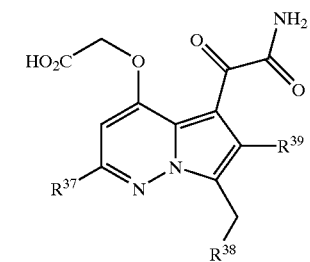

| Compound No. | $R^{37}$ | $R^{38}$ | $R^{39}$ |
|---|---|---|---|
| II-316 | Me | AA | Et |
| II-317 | Me | AB | Et |
| II-318 | Me | AC | Et |
| II-319 | Me | AD | Et |
| II-320 | Me | AE | Et |
| II-321 | Me | AF | Et |
| II-322 | Me | AG | Et |
| II-323 | Me | AH | Et |
| II-324 | Me | AI | Et |
| II-325 | Me | AJ | Et |
| II-326 | Me | AK | Et |
| II-327 | Me | AL | Et |
| II-328 | Me | AM | Et |
| II-329 | Me | AN | Et |
| II-330 | Me | AO | Et |
| II-331 | Me | AP | Et |
| II-332 | Me | AQ | Et |
| II-333 | Me | AR | Et |
| II-334 | Me | AS | Et |
| II-335 | Me | AT | Et |
| II-336 | Me | AU | Et |
| II-337 | Me | AV | Et |
| II-338 | Me | AW | Et |
| II-339 | Me | AX | Et |
| II-340 | Me | AY | Et |
| II-341 | Me | AZ | Et |
| II-342 | Me | BA | Et |
| II-343 | Me | BB | Et |
| II-344 | Me | BC | Et |
| II-345 | Me | BD | Et |
| II-346 | Me | BE | Et |
| II-347 | Me | BF | Et |
| II-348 | Me | BG | Et |
| II-349 | Me | BH | Et |
| II-350 | Me | BI | Et |
| II-351 | Et | AA | Et |
| II-352 | Et | AB | Et |
| II-353 | Et | AC | Et |
| II-354 | Et | AD | Et |
| II-355 | Et | AE | Et |
| II-356 | Et | AF | Et |
| II-357 | Et | AG | Et |
| II-358 | Et | AH | Et |
| II-359 | Et | AI | Et |
| II-360 | Et | AJ | Et |
| II-361 | Et | AK | Et |
| II-362 | Et | AL | Et |
| II-363 | Et | AM | Et |
| II-364 | Et | AN | Et |
| II-365 | Et | AO | Et |
| II-366 | Et | AP | Et |
| II-367 | Et | AQ | Et |
| II-368 | Et | AR | Et |
| II-369 | Et | AS | Et |
| II-370 | Et | AT | Et |
| II-371 | Et | AU | Et |
| II-372 | Et | AV | Et |
| II-373 | Et | AW | Et |
| II-374 | Et | AX | Et |
| II-375 | Et | AY | Et |
| II-376 | Et | AZ | Et |
| II-377 | Et | BA | Et |

TABLE 15-continued

| | | | |
|---|---|---|---|
| II-378 | Et | BB | Et |
| II-379 | Et | BC | Et |
| II-380 | Et | BD | Et |
| II-381 | Et | BE | Et |
| II-382 | Et | BF | Et |
| II-383 | Et | BG | Et |
| II-384 | Et | BH | Et |
| II-385 | Et | BI | Et |
| II-386 | Ph | AA | Et |
| II-387 | Ph | AB | Et |
| II-388 | Ph | AC | Et |
| II-389 | Ph | AD | Et |
| II-390 | Ph | AE | Et |
| II-391 | Ph | AF | Et |
| II-392 | Ph | AG | Et |
| II-393 | Ph | AH | Et |
| II-394 | Ph | AI | Et |
| II-395 | Ph | AJ | Et |
| II-396 | Ph | AK | Et |
| II-397 | Ph | AL | Et |
| II-398 | Ph | AM | Et |
| II-399 | Ph | AN | Et |
| II-400 | Ph | AO | Et |
| II-401 | Ph | AP | Et |
| II-402 | Ph | AQ | Et |
| II-403 | Ph | AR | Et |
| II-404 | Ph | AS | Et |
| II-405 | Ph | AT | Et |
| II-406 | Ph | AU | Et |
| II-407 | Ph | AV | Et |
| II-408 | Ph | AW | Et |
| II-409 | Ph | AX | Et |
| II-410 | Ph | AY | Et |
| II-411 | Ph | AZ | Et |
| II-412 | Ph | BA | Et |
| II-413 | Ph | BB | Et |
| II-414 | Ph | BC | Et |
| II-415 | Ph | BD | Et |
| II-416 | Ph | BE | Et |
| II-417 | Ph | BF | Et |
| II-418 | Ph | BG | Et |
| II-419 | Ph | BH | Et |
| II-420 | Ph | BI | Et |

TABLE 16

| Compound No. | $R^{37}$ | $R^{38}$ | $R^{39}$ |
|---|---|---|---|
| II-421 | Me | AA | Me |
| II-422 | Me | AB | Me |
| II-423 | Me | AC | Me |
| II-424 | Me | AD | Me |
| II-425 | Me | AE | Me |
| II-426 | Me | AF | Me |
| II-427 | Me | AG | Me |
| II-428 | Me | AH | Me |
| II-429 | Me | AI | Me |
| II-430 | Me | AJ | Me |
| II-431 | Me | AK | Me |
| II-432 | Me | AL | Me |
| II-433 | Me | AM | Me |
| II-434 | Me | AN | Me |

TABLE 16-continued

| | | | |
|---|---|---|---|
| II-435 | Me | AO | Me |
| II-436 | Me | AP | Me |
| II-437 | Me | AQ | Me |
| II-438 | Me | AR | Me |
| II-439 | Me | AS | Me |
| II-440 | Me | AT | Me |
| II-441 | Me | AU | Me |
| II-442 | Me | AV | Me |
| II-443 | Me | AW | Me |
| II-444 | Me | AX | Me |
| II-445 | Me | AY | Me |
| II-446 | Me | AZ | Me |
| II-447 | Me | BA | Me |
| II-448 | Me | BB | Me |
| II-449 | Me | BC | Me |
| II-450 | Me | BD | Me |
| II-451 | Me | BE | Me |
| II-452 | Me | BF | Me |
| II-453 | Me | BG | Me |
| II-454 | Me | BH | Me |
| II-455 | Me | BI | Me |
| II-456 | Et | AA | Me |
| II-457 | Et | AB | Me |
| II-458 | Et | AC | Me |
| II-459 | Et | AD | Me |
| II-460 | Et | AE | Me |
| II-461 | Et | AF | Me |
| II-462 | Et | AG | Me |
| II-463 | Et | AH | Me |
| II-464 | Et | AI | Me |
| II-465 | Et | AJ | Me |
| II-466 | Et | AK | Me |
| II-467 | Et | AL | Me |
| II-468 | Et | AM | Me |
| II-469 | Et | AN | Me |
| II-470 | Et | AO | Me |
| II-471 | Et | AP | Me |
| II-472 | Et | AQ | Me |
| II-473 | Et | AR | Me |
| II-474 | Et | AS | Me |
| II-475 | Et | AT | Me |
| II-476 | Et | AU | Me |
| II-477 | Et | AV | Me |
| II-478 | Et | AW | Me |
| II-479 | Et | AX | Me |
| II-480 | Et | AY | Me |
| II-481 | Et | AZ | Me |
| II-482 | Et | BA | Me |
| II-483 | Et | BB | Me |
| II-484 | Et | BC | Me |
| II-485 | Et | BD | Me |
| II-486 | Et | BE | Me |
| II-487 | Et | BF | Me |
| II-488 | Et | BG | Me |
| II-489 | Et | BH | Me |
| II-490 | Et | BI | Me |
| II-491 | Ph | AA | Me |
| II-492 | Ph | AB | Me |
| II-493 | Ph | AC | Me |
| II-494 | Ph | AD | Me |
| II-495 | Ph | AE | Me |
| II-496 | Ph | AF | Me |
| II-497 | Ph | AG | Me |
| II-498 | Ph | AH | Me |
| II-499 | Ph | AI | Me |
| II-500 | Ph | AJ | Me |
| II-501 | Ph | AK | Me |
| II-502 | Ph | AL | Me |
| II-503 | Ph | AM | Me |
| II-504 | Ph | AN | Me |
| II-505 | Ph | AO | Me |
| II-506 | Ph | AP | Me |
| II-507 | Ph | AQ | Me |
| II-508 | Ph | AR | Me |
| II-509 | Ph | AS | Me |
| II-510 | Ph | AT | Me |
| II-511 | Ph | AU | Me |
| II-512 | Ph | AV | Me |
| II-513 | Ph | AW | Me |

TABLE 16-continued

| | | | |
|---|---|---|---|
| II-514 | Ph | AX | Me |
| II-515 | Ph | AY | Me |
| II-516 | Ph | AZ | Me |
| II-517 | Ph | BA | Me |
| II-518 | Ph | BB | Me |
| II-519 | Ph | BC | Me |
| II-520 | Ph | BD | Me |
| II-521 | Ph | BE | Me |
| II-522 | Ph | BF | Me |
| II-523 | Ph | BG | Me |
| II-524 | Ph | BH | Me |
| II-525 | Ph | BI | Me |

TABLE 17

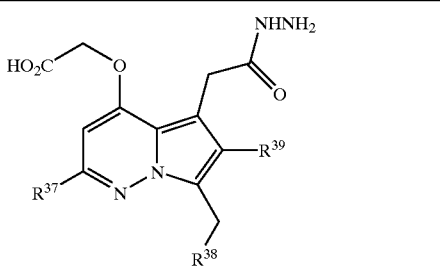

| Compound No. | $R^{37}$ | $R^{38}$ | $R^{39}$ |
|---|---|---|---|
| II-526 | Me | AA | Et |
| II-527 | Me | AB | Et |
| II-528 | Me | AC | Et |
| II-529 | Me | AD | Et |
| II-530 | Me | AE | Et |
| II-531 | Me | AF | Et |
| II-532 | Me | AG | Et |
| II-533 | Me | AH | Et |
| II-534 | Me | AI | Et |
| II-535 | Me | AJ | Et |
| II-536 | Me | AK | Et |
| II-537 | Me | AL | Et |
| II-538 | Me | AM | Et |
| II-539 | Me | AN | Et |
| II-540 | Me | AO | Et |
| II-541 | Me | AP | Et |
| II-542 | Me | AQ | Et |
| II-543 | Me | AR | Et |
| II-544 | Me | AS | Et |
| II-545 | Me | AT | Et |
| II-546 | Me | AU | Et |
| II-547 | Me | AV | Et |
| II-548 | Me | AW | Et |
| II-549 | Me | AX | Et |
| II-550 | Me | AY | Et |
| II-551 | Me | AZ | Et |
| II-552 | Me | BA | Et |
| II-553 | Me | BB | Et |
| II-554 | Me | BC | Et |
| II-555 | Me | BD | Et |
| II-556 | Me | BE | Et |
| II-557 | Me | BF | Et |
| II-558 | Me | BG | Et |
| II-559 | Me | BH | Et |
| II-560 | Me | BI | Et |
| II-561 | Et | AA | Et |
| II-562 | Et | AB | Et |
| II-563 | Et | AC | Et |
| II-564 | Et | AD | Et |
| II-565 | Et | AE | Et |
| II-566 | Et | AF | Et |
| II-567 | Et | AG | Et |
| II-568 | Et | AH | Et |
| II-569 | Et | AI | Et |
| II-570 | Et | AJ | Et |

TABLE 17-continued

| | | | |
|---|---|---|---|
| II-571 | Et | AK | Et |
| II-572 | Et | AL | Et |
| II-573 | Et | AM | Et |
| II-574 | Et | AN | Et |
| II-575 | Et | AO | Et |
| II-576 | Et | AP | Et |
| II-577 | Et | AQ | Et |
| II-578 | Et | AR | Et |
| II-579 | Et | AS | Et |
| II-580 | Et | AT | Et |
| II-581 | Et | AU | Et |
| II-582 | Et | AV | Et |
| II-583 | Et | AW | Et |
| II-584 | Et | AX | Et |
| II-585 | Et | AY | Et |
| II-586 | Et | AZ | Et |
| II-587 | Et | BA | Et |
| II-588 | Et | BB | Et |
| II-589 | Et | BC | Et |
| II-590 | Et | BD | Et |
| II-591 | Et | BE | Et |
| II-592 | Et | BF | Et |
| II-593 | Et | BG | Et |
| II-594 | Et | BH | Et |
| II-595 | Et | BI | Et |
| II-596 | Ph | AA | Et |
| II-597 | Ph | AB | Et |
| II-598 | Ph | AC | Et |
| II-599 | Ph | AD | Et |
| II-600 | Ph | AE | Et |
| II-601 | Ph | AF | Et |
| II-602 | Ph | AG | Et |
| II-603 | Ph | AH | Et |
| II-604 | Ph | AI | Et |
| II-605 | Ph | AJ | Et |
| II-606 | Ph | AK | Et |
| II-607 | Ph | AL | Et |
| II-608 | Ph | AM | Et |
| II-609 | Ph | AN | Et |
| II-610 | Ph | AO | Et |
| II-611 | Ph | AP | Et |
| II-612 | Ph | AQ | Et |
| II-613 | Ph | AR | Et |
| II-614 | Ph | AS | Et |
| II-615 | Ph | AT | Et |
| II-616 | Ph | AU | Et |
| II-617 | Ph | AV | Et |
| II-618 | Ph | AW | Et |
| II-619 | Ph | AX | Et |
| II-620 | Ph | AY | Et |
| II-621 | Ph | AZ | Et |
| II-622 | Ph | BA | Et |
| II-623 | Ph | BB | Et |
| II-624 | Ph | BC | Et |
| II-625 | Ph | BD | Et |
| II-626 | Ph | BE | Et |
| II-627 | Ph | BF | Et |
| II-628 | Ph | BG | Et |
| II-629 | Ph | BH | Et |
| II-630 | Ph | BI | Et |

Test Example

Inhibition Test of Human Secretory Phospholipase $A_2$

Analytical Experiment

In order to identify and evaluate an inhibitor of recombinant human secretory phospholipase $A_2$, the following chromogenic assay is utilized. The assay herein has been applied for high volume screening wherein 96 well microtiterplate is used. A general explanation for such assay is described in "Analysis of Human Synovial Fluid Phospholipase $A_2$ on Short Chain Phosphatidylcholine-Mixed Micelles: Development of a Spectrophotometric Assay Suitable for a Micortiterplate Reader" (Analytical Biochemistry, 204, pp 190–197, 1992 by Laure. J. Reynolds. Lori L. Hughes and Edward A. Dennis: the disclosure of which is incorporated herein for reference.

Reagents:

Reaction Buffer $CaCl_2.6H_2O$ (2.19 g/L)

KCl (7.455 gL)

Bovine Serum Albumin (fatty acid free) (1 g/L) (Sigma A-7030)

Tris-HCl (3.94 g/L)

pH 7.5 (adjusted with NaOH)

Enzyme Buffer 0.05 M-AcONa 0.2 M-NaCl pH 4.5 (adjusted with acetic acid)

Enzyme Solution 1 mg of $sPLA_2$ is dissolved in 1 ml of an enzyme buffer. Thereafter, the solution is maintained at 4° C.

In the assay, 5 µl of the solution is diluted with 1995 µl of the reaction buffer to be used.

DTNB 198 mg of 5,5'-dithiobis-2-benzoic acid (manufactured by Wako Pure Chemicals) is dissolved in 100 ml of $H_2O$ pH 7.5 (adjusted with NaOH)

Substrate Solution 100 mg of racemic 1,2-bis(heptanoylthio)-1,2-dideoxy-sn-glycero-3-phospholylcholine is dissolved in 1 ml of chloroform.

Triton-X 100

624.9 mg of Triton-X 100 is dissolved in the reaction buffer.

Enzyme Reaction: for 1 plate of Microtiterplate 1) 0.106 ml of the substrate solution is put in a centrifugal tube, and nitrogen gas is jetted to remove the solvent. 0.54 ml of Triton-X 100 is added thereto, the mixture is stirred, thereafter it is sonified in a bath type sonification to dissolve. To the resulting product are added 17.8 ml1 of the reaction buffer and 0.46 ml of DTNB, and 0.18 ml each of the admixture is poured to wells of the 96 well microtiterplate.
2) 10 µl of a test compound (or solvent blank) are added in accordance with alignment of plates which has been previously set.
3) Incubation is effected at 40° C. for 15 minutes.
4) 20 µl of an enzyme solution ($sPLA_2$) which has been previously diluted (50 ng/well) are added to start reaction (40° C., 30 minutes).
5) Changes in absorbancy for 30 minutes are measured by a plate reader, and inhibition activity was calculated (OD: 405 nm).
6) $IC_{50}$ was determined by plotting log concentration with respect to inhibition values within 10% to 90% inhibiting range.

Results of the human secretory phospholipase $A_2$ inhibition test are shown in the following Table 18.

TABLE 18

| Compound No. | $IC_{50}$ (µM) |
| --- | --- |
| I-1 | 0.248 |
| I-2 | 0.009 |
| I-3 | 0.013 |

TABLE 18-continued

| Compound No. | $IC_{50}$ (µM) |
| --- | --- |
| I-4 | 0.150 |
| I-5 | 0.011 |
| I-6 | 0.238 |
| I-7 | 0.223 |
| I-8 | 0.184 |
| I-9 | 0.165 |
| I-10 | 0.296 |
| I-11 | 0.067 |
| I-12 | 0.745 |
| I-13 | 0.238 |
| I-14 | 0.883 |
| I-15 | 0.097 |
| I-16 | 0.012 |
| I-17 | 0.007 |
| I-18 | 0.010 |
| I-19 | 0.010 |
| I-20 | 0.019 |
| I-21 | 0.006 |
| I-22 | 0.022 |
| I-23 | 0.007 |
| I-24 | 0.021 |
| I-25 | 0.006 |
| I-26 | 0.177 |
| I-27 | 0.126 |
| I-28 | |
| I-29 | 1.517 |
| I-30 | 4.521 |
| I-31 | 15.630 |
| I-32 | 0.239 |
| I-33 | 0.072 |
| I-34 | 0.058 |
| I-35 | 0.111 |
| I-36 | 0.102 |
| I-37 | 0.212 |
| I-38 | 0.227 |
| I-39 | 0.079 |
| I-40 | 0.099 |
| I-41 | 0.064 |
| I-42 | 0.026 |
| I-43 | 0.154 |
| I-44 | 0.315 |
| I-45 | 0.030 |
| I-46 | 0.268 |
| I-47 | 0.618 |
| I-48 | 0.211 |
| I-49 | 7.811 |
| I-50 | 0.526 |
| I-51 | 25.589 |
| I-52 | 0.093 |
| I-53 | 3.741 |
| I-54 | 0.148 |
| I-55 | 0.056 |
| I-56 | 0.052 |
| I-57 | 0.007 |
| I-58 | 0.009 |
| I-59 | 1.078 |
| I-60 | 0.365 |
| I-61 | 2.610 |
| I-62 | 0.012 |
| I-63 | 0.006 |
| I-64 | 0.007 |
| I-65 | 0.007 |
| I-66 | 0.006 |
| I-67 | 0.016 |
| I-68 | 0.025 |
| I-69 | 0.008 |
| I-70 | 0.009 |
| I-71 | 0.008 |
| I-72 | 0.009 |
| I-73 | 0.019 |
| I-74 | 0.015 |
| I-75 | 0.009 |
| I-76 | 0.006 |
| I-77 | 0.010 |
| I-78 | 0.005 |
| I-79 | 0.464 |

TABLE 18-continued

| Compound No. | IC$_{50}$ ($\mu$M) |
|---|---|
| I-80 | 0.013 |
| I-81 | 8.186 |
| I-82 | 0.093 |
| I-83 | 0.083 |
| I-84 | 0.008 |

Formulation Example

It is to be noted that the following Formulation Examples 1 to 8 are mere illustration, but not intended to limit the scope of the invention. The term "active ingredient" means the compounds represented by the formula (I), the prodrugs thereof, their pharmaceutical acceptable salts, or their solvates.

Formulation Example 1

Hard gelatin capsules are prepared using of the following ingredients:

| | Dose (mg/capsule) |
|---|---|
| Active ingredient | 250 |
| Starch, dried | 200 |
| Magnesium stearate | 10 |
| Total | 460 mg |

Formulation Example 2

A tablet is prepared using of the following ingredients:

| | Dose (mg/tablet) |
|---|---|
| Active ingredient | 250 |
| Cellulose, microcrystals | 400 |
| Silicon dioxide, fumed | 10 |
| Stearic acid | 5 |
| Total | 665 mg |

The components are blended and compressed to form tablets each weighing 665 mg.

Formulation Example 3

An aerosol solution is prepared containing the following components:

| | Weight |
|---|---|
| Active ingredient | 0.25 |
| Ethanol | 25.75 |
| Propellant 22 (chlorodifluoromethane) | 74.00 |
| Total | 100.00 |

The active compound is mixed with ethanol and the admixture added to a portion of the propellant 22, cooled to −30° C. and transferred to filling device. The required amount is then fed to stainless steel container and diluted with the reminder of the propellant. The valve units are then fitted to the container.

Formulation Example 4

Tablets, each containing 60 mg of active ingredient, are made as follows.

| Active ingredient | 60 mg |
|---|---|
| Starch | 45 mg |
| Microcrystals cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly. The aqueous solution containing polyvinylpyrrolidone is mixed with the resultant powder, and the admixture then is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are then added to the granules which, after mixing, are compressed on a tablet machine to yield tablets each weighing 150 mg.

Formulation Example 5

| Active ingredient | 80 mg |
|---|---|
| Starch | 59 mg |
| Microcrystals cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation Example 6

| Active ingredient | 225 mg |
|---|---|
| Saturated fatty acid glycerides | 2000 mg |
| Total | 2225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation Example 7

Suspensions, each containing 50 mg of active ingredient per 5 ml dose, are made as follows:

| | |
|---|---|
| Active ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 U.S. sieve, and mixed with the sodium carboxymethyl cellulose and syrup to form a smooth paste. The benzoic acid solution, flavor and color are diluted with a portion of the water and added, with stirring. Sufficient water is then added to produce the required volume.

Formulation Example 8

| An intravenous formulation may be prepared as follows: | |
|---|---|
| Active ingredient | 100 mg |
| Isotonic saline | 1000 ml |

The solution of the above ingredients generally is administered intravenously to a subject at a rate of 1 ml per minute.

Formulation Example 9

Composition of lyophilized preparations (in 1 vial) is made as follows:

| | |
|---|---|
| Active ingredient | 127 mg |
| Trisodium citrate dihydrate | 36 mg |
| Mannitol | 180 mg |

The above materials are dissolved in water for injection such that the concentration of Active ingredient is 10 mg/g. The primary freezing step is done for 3 hours at −40° C., the heat treating step for 10 hours at −10° C., and the re-freezing step for 3 hours at −40° C. Then, the primary drying step is performed for 60 hours at 0° C., 10 Pa and the secondary drying step for 5 hours at 60° C., 4 Pa. Thus the lyophilized preparation is obtained.

Industrial Applicability

The compounds according to the present invention have sPLA$_2$ inhibiting activity, so that the compounds of the invention inhibits sPLA$_2$-mediated fatty acid (such as arachidonic acid) release, whereby it is effective for treating septic shock and the like.

What is claimed is:
1. A compound represented by the formula (I):

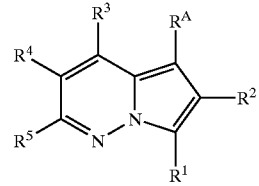

wherein R$^1$ is methyl or a group represented by the formula:

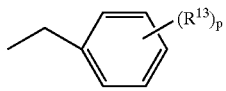

or

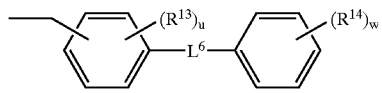

wherein L$^6$ is a bond or —O—; R$^{13}$ and R$^{14}$ are independently selected from the group consisting of halogen, C1 to C10 alkyl, C1 to C10 alkoxy, C1 to C10 alkylthio, aryl, thienyl, benzothienyl, thiazolyl, benzothiazolyl, oxazolyl, benzoxazolyl, and C1 to C10 haloalkyl; p and w aye independently an integer from 0 to 5, u is an integer from 0 to 4;

R$^2$ is C1 to C4 alkyl;

R$^3$ is —O—(CH$_2$)$_k$—COOH, wherein k is an integer from 1 to 3;

R$^4$ is a hydrogen atom;

R$^5$ is selected from the group consisting of hydrogen atom, C1 to C6 alkyl, C7 to C12 aralkyl, C1 to C6 alkyloxy, C1 to C6 alkylthio, C1 to C6 hydroxyalkyl, C2 to C6 haloalkyloxy, halogen, carboxy, C1 to C6 alkyloxycarbonyl, axyloxy, aryloxy C1 to C8 alkyl, arylthio, arylthio C1 to C8 alkyl, cyano C1 to C8 alkyl, phenyl, cyclohexyl, 4-fluorophenyloxymethyl, trifluoromethyl, cblorometbyl, pyrrolidin-1-ylmethyl, morpholinomethyl, 4methylpiperazin-1-ylmethyl, 4-fluorophenyl, 4-methyloxyphenyl, cyclopentyl, benzodioxol-5-yl, methylthiomethyl, methyloxymethyl, 4-methyloxyphenyloxymethyl, 3,4-dimethyloxyphenyloxymethyl, 4-methylphenyloxymethyl, and 2,5-dioxopyrrolidin-1-ylmethyl; and R$^A$ is a group represented by the formula:

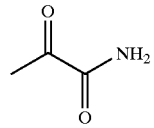 or 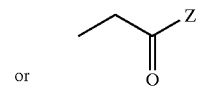

wherein Z is —NH$_2$ or —NHNH$_2$, or a pharmaceutically acceptable salt, hydrate or ester thereof.

2. A pyrrolo[1,2-b]pyridazine compound selected from the group consisting of:
Methyl (5-aminooxalyl-7-benzyl-6-ethylpyrrolo[1,2-b]pyridazine-4-yloxy)acetate,
(5-aminooxalyl-7-benzyl-6-ethylpyrrolo[1,2-b]pyridazine-4-yloxy)acetic acid,
Sodium (5-aminooxalyl-7-benzyl-6-ethylpyrrolo[1,2-b]pyridazine-4-yloxy)acetate, Methyl (5-aminooxalyl-7-benzyl-6-ethyl-2-methylpyrrolo[1,2-b]pyridazine-4-yloxy)acetate,
(5-aminooxalyl-7-benzyl-6-ethyl-2-methylpyrrolo[1,2-b]pyridazine-4-yloxy)acetic acid,
Methyl (5-aminooxalyl-7-benzyl-2,6-dimethylpyrrolo[1,2-b]pyridazine-4-yloxy)acetate,
Ethyl (5-aminooxalyl-7-benzyl-2,6-dimethylpyrrolo[1,2-b]pyridazine-4-yloxy)acetate,
2-(Morpholine-4-yl)ethyl (5-aminooxalyl-7-benzyl-2,6-dimethylpyrrolo[1,2-b]pyridazine-4-yloxy)acetate,
(5-aminooxalyl-7-benzyl-2,6-dimethylpyrrolo[1,2-b]pyridazine-4-yloxy)acetic acid,
Sodium (5-aminooxalyl-7-benzyl-2,6-dimethylpyrrolo[1,2-b]pyridazine-4-yloxy)acetate,
Methyl (5-aminooxalyl-7-benzyl-6-methyl-2-phenylpyrrolo[1,2-b]pyridazine-4-yloxy)acetate,
(5-aminooxalyl-7-benzyl-6-methyl-2-phenylpyrrolo[1,2-b]pyridazine-4-yloxy)acetic acid,
Methyl [5-aminooxalyl-7-benzyl-6-ethyl-2-phenylpyrrolo[1,2-b]pyridazine-4-yloxy]acetate,
[5-aminooxalyl-6-ehtyl-7-(2-flourobenzyl)-2-phenylpyrrolo[1,2-b]pyridazine-4-yloxy]acetic acid
Methyl [5-aminooxalyl-7-benxyl-6-ethyl-2-(4-fluorobenzyl)pyrrolo[1,2-b]pyridazine-4-yloxy]acetate,
[5-aminooxalyl-6-ethyl-7-(2-fluorobenzyl)-2-phenylpyrrolo[1,2-b]pyridazine-4-yloxy]acetic acid,
Methyl [5-aminooxalyl-7-benzyl-6-ethyl-2-(4-fluorophenyl)pyrrolo[1,2-b]pyridazine-4-yloxy]acetate,
[5-aminooxalyl-7-benzyl-6-ethyl-2-(4-fluorophenyl)pyrrolo[1,2-b]pyridazine-4-yloxy]acetic acid,
Methyl (5-aminooxalyl-7-benzyl-6-ethyl-2-phenoxymethylpyrrolo[1,2-b]pyridazine-4-yloxy)acetate,
(5-aminooxalyl-7-benzyl-6-ethyl-2-phenoxymethylpyrrolo[1,2-b]pyridazine-4-yloxy)acetic acid,
Methyl [5-aminooxalyl-7-benzyl-6-ethyl-2-(4-methoxyphenyl)pyrrolo[1,2-b]pyridazine-4-yloxy]acetate,
[5-aminooxalyl-7-benzyl-6-ethyl-2-(4-methoxyphenyl)pyrrolo[1,2-b]pyridazine-4-yloxy]acetic acid,
Methyl [5-aminooxalyl-6-ethyl-2-methyl-7-(2-phenylbenzyl)pyrrolo[1,2-b]pyridazine-4-yloxy]acetate,
[5-aminooxalyl-6-ethyl-2-methyl-7-(2-phenylbenzyl)pyrrolo[1,2-b]pyridazine-4-yloxy]acetic acid,
Methyl [5-aminooxalyl-6-ethyl-2-methyl-7-(3-phenoxybenzyl)pyrrolo[1,2-b]pyridazine-4-yloxy]acetate,
[5-aminooxalyl-6-ethyl-2-methyl-7-(3-phenoxybenzyl)pyrrolo[1,2-b]pyridazine-4-yloxy]acetic acid,
Methyl (5-aminooxalyl-7-benzyl-6-methyl-2-propylpyrrolo[1,2-b]pyridazine-4-yloxy)acetate,
(5-aminooxalyl-7-benzyl-6-methyl-2-propylpyrrolo[1,2-b]pyridazine-4-yloxy)acetic acid,
Methyl (5-aminooxalyl-2,7-dibenzyl-6-methylpyrrolo[1,2-b]pyridazine-4-yloxy)acetate,
(5-aminooxalyl-2,7-dibenzyl-6-methylpyrrolo[1,2-b]pyridazine-4-yloxy)acetic acid,
Methyl[5-aminooxalyl-2,6-dimethyl-7-[2-(4-fluorophenyl)benzyl]pyrrolo[1,2-b]pyridazine-4-yloxy]acetate, and
[5-aminooxalyl-2,6-dimethyl-7-[2-(4-fluorophenyl)benzyl]pyrrolo[1,2-b]pyridazine-4-yloxy]acetic acid;
or a pharmaceutically acceptable salt, hydrate or ester thereof.

3. A pyrrolo[1,2-b]pyridazine compound selected from the group consisting of

Methyl(5-aminooxalyl-7-benzyl-2,6-dimethylpyrrolo[1,2-b]pyridazine-4-yloxy)acetate,
Ethyl (5-aminooxalyl-7-benzyl-2,6-dimethylpyrrolo[1,2-b]pyridazine-4-yloxy)acetate,
2-(Morpholine-4-yl)ethyl (5-aminooxalyl-7-benzyl-2,6-dimethylpyrrolo[1,2-b]pyridazine-4-yloxy)acetate,
Sodium (5-aminooxalyl-7-benzyl-2,6-dimethylpyrrolo[1,2-b]pyridazine-4-yloxy)acetate,
(5-aminooxalyl-7-benzyl-2,6-dimethylpyrrolo[1,2-b]pyridazine-4-yloxy)acetic acid,
Methyl (5-aminooxalyl-7-benzyl-6-methyl-2-phenylpyrrolo[1,2-b]pyridazine-4-yloxy)acetate,
Ethyl (5-aminooxalyl-7-benzyl-6-methyl-2-phenylpyrrolo[1,2-b]pyridazine-4-yloxy)acetate,
2-(Morpholine-4-yl)ethyl (5-aminooxalyl-7-benzyl-6-methyl-2-phenylpyrrolo[1,2-b]pyridazine-4-yloxy)acetate,
Sodium (5-aminooxalyl-7-benzyl-6-methyl-2-phenylpyrrolo[1,2-b]pyridazine-4-yloxy)acetate,
(5-aminooxalyl-7-benzyl-6-methyl-2-phenylpyrrolo[1,2-b]pyridazine-4-yloxy)acetic acid,
Methyl (5-aminooxalyl-7-benzyl-6-ethyl-2-phenoxymethylpyrrolo[1,2-b]pyridazine-4-yloxy)acetate,
Ethyl (5-aminooxalyl-7-benzyl-6-ethyl-2-phenoxymethylpyrrolo[1,2-b]pyridazine-4-yloxy)acetate,
2-(Morpholine-4-yl)ethyl 5-aminooxalyl-7-benzyl-6-ethyl-2-phenoxymethylpyrrolo[1,2-b]pyridazine-4-yloxy)acetate,
Sodium (5-aminooxalyl-7-benzyl-6-ethyl-2-phenoxymethylpyrrolo[1,2-b]pyridazine-4-yloxy)acetate,
(5-aminooxalyl-7-benzyl-6-ethyl-2-phenoxymethylpyrrolo[1,2-b]pyridazine-4-yloxy)acetic acid,
Methyl [5-aminooxalyl-6-ethyl-2-methyl-7-(2-phenylbenzyl)pyrrolo[1,2-b]pyridazine-4-yloxy]acetate,
Ethyl [5-aminooxalyl-6-ethyl-2-methyl-7-(2-phenylbenzyl)pyrrolo[1,2-b]pyridazine-4-yloxy]acetate,
2-(Morpholine-4-yl)ethyl 5-aminooxalyl-6-ethyl-2-methyl-7-(2-phenylbenzyl)pyrrolo[1,2-b]pyridazine-4-yloxy)acetate,
Sodium [5-aminooxalyl-6-ethyl-2-methyl-7-(2-phenylbenzyl)pyrrolo[1,2-b]pyridazine-4-yloxy]acetate,
(5-aminooxalyl-6-ethyl-2-methyl-7-(2-phenylbenzyl)pyrrolo[1,2-b]pyridazine-4-yloxy)acetic acid,
Methyl (5 -aminooxalyl-7-benzyl-6-methyl-2-propylpyrrolo[1,2-b]pyridazine-4-yloxy)acetate,
Ethyl (5-aminooxalyl-7-benzyl-6-methyl-2-propylpyrrolo[1,2-b]pyridazine-4-yloxy)acetate,
2-(Morpholine-4-yl)ethyl 5-aminooxalyl-7-benzyl-6-methyl-2-propylpyrrolo[1,2-b]pyridazine-4-yloxy)acetate, Sodium (5-aminooxalyl-7-benzyl-6-methyl-2-propylpyrrolo[1,2-b]pyridazine-4-yloxy)acetate, and (5-aminooxalyl-7-benzyl-6-methyl-2-propylpyrrolo[1,2-b]pyridazine-4-yloxy)acetic acid, or a pharmaceutically acceptable salt, hydrate or ester thereof.

4. A compound represented by the formula (IV):

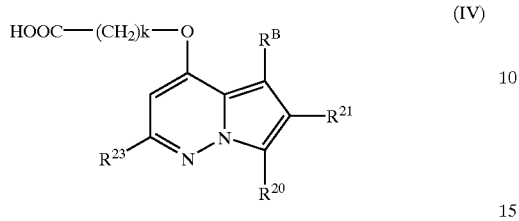

(IV)

wherein $R^{20}$ is methyl or a group represented by the formula:

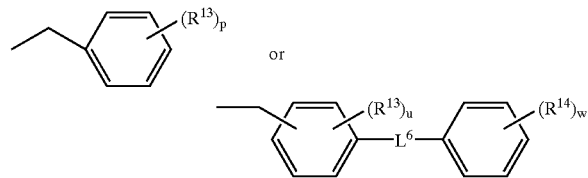

wherein $L^6$ is a bond or —O—; $R^{13}$ and $R^{14}$ are independently selected from a halogen, C1 to C10 alkyl, C1 to C10 alkyloxy, C1 to C10 alkylthio, aryl, thienyl, benzothienyl, thiazolyl, benzothiazolyl, oxazolyl, benzoxazolyl, and C1 to C10 haloalkyl; p and w are independently an integer from 0 to 5, u is an integer from 0 to 4;

$R^{21}$ is C1 to C3 alkyl;

$R^{23}$ is hydrogen atom, C1 to C6 alkyl, C7 to C12 aralkyl, C1 to C6 alkyloxy, C1 to C6 alkylthio, C1 to C6 hydroxyalkyl, C2 to C6 haloalkyloxy, halogen, carboxy, C1 to C6 alkyloxycarbonyl, aryloxy, aryloxy C1 to C8 alkyl, arylthio, arylthio C1 to C8 alkyl, cyano C1 to C8 alkyl, phenyl, cyclohexyl;

$R^B$ is a group represented by the formula:

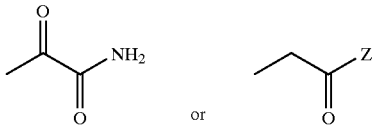

wherein Z is —NH$_2$ or —NHNH$_2$; and k is an integer from 1 to 3; or a pharmaceutically acceptable salt, hydrate or ester thereof.

5. A pharmaceutical composition for sepsis or septic shock containing a compound as claimed in claim 1 as an active ingredient in combination with a pharmaceutically acceptable carrier.

6. A method of treating a human or non-human mammal, to alleviate the pathological effects of sepsis and septic shock; wherein the method comprises administration to said mammal of a pyrrolo[1,2-b]pyridazine compound as claimed in claim 1 in a pharmaceutically effective amount.

7. A method of treating a mammal, to alleviate the pathological effects of sepsis or septic shock; wherein the method comprises administration to said mammal of a pyrrolo[1,2-b]pyridazine compound as claimed in claim 1 in a pharmaceutically effective amount.

* * * * *